(12) United States Patent
Khatri et al.

(10) Patent No.: US 10,920,275 B2
(45) Date of Patent: Feb. 16, 2021

(54) METHODS FOR DIAGNOSIS OF TUBERCULOSIS

(71) Applicant: The Board of Trustees of the Leland Stanford Junior University, Stanford, CA (US)

(72) Inventors: Purvesh Khatri, Menlo Park, CA (US); Timothy E. Sweeney, San Francisco, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 300 days.

(21) Appl. No.: 15/766,357

(22) PCT Filed: Oct. 14, 2016

(86) PCT No.: PCT/US2016/057145
§ 371 (c)(1),
(2) Date: Apr. 5, 2018

(87) PCT Pub. No.: WO2017/066641
PCT Pub. Date: Apr. 20, 2017

(65) Prior Publication Data
US 2018/0291452 A1    Oct. 11, 2018

Related U.S. Application Data

(60) Provisional application No. 62/241,506, filed on Oct. 14, 2015.

(51) Int. Cl.
| | | |
|---|---|---|
| C12Q 1/68 | (2018.01) | |
| G01N 33/53 | (2006.01) | |
| C12Q 1/6883 | (2018.01) | |
| A61P 31/06 | (2006.01) | |
| A61K 31/56 | (2006.01) | |
| C12Q 1/689 | (2018.01) | |

(52) U.S. Cl.
CPC ............ *C12Q 1/6883* (2013.01); *A61K 31/56* (2013.01); *A61P 31/06* (2018.01); *C12Q 1/689* (2013.01); *A61K 2300/00* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 2006/0019256 A1* | 1/2006 | Clarke | .................. | C12N 5/0695 435/6.14 |
| 2014/0080732 A1* | 3/2014 | Banchereau | ......... | C12Q 1/6883 506/9 |
| 2015/0197806 A1 | 7/2015 | Ball | | |

FOREIGN PATENT DOCUMENTS

| | | |
|---|---|---|
| WO | WO 2014/019977 A1 | 2/2014 |
| WO | WO 2014/093872 | 6/2014 |

OTHER PUBLICATIONS

Anderson et al., "Diagnosis of Childhood Tuberculosis and Host RNA Expression in Africa", N Engl J Med., 2014, 370(18): 1712-1723.
Berry et al., "An Interferon-Inducible Neutrophil-Driven Blood Transcriptional Signature in Human Tuberculosis", Nature, 2010, 466(7309): 973-977.
Bloom et al., "Transcriptional Blood Signatures Distinguish Pulmonary Tuberculosis, Pulmonary Sarcoidosis, Pneumonias and Lung Cancers", PLOS ONE, 2013, 8(8): e70630, pp. 1-17.
Bloom et al., "Detectable Changes in the Blood Transcriptome Are Present after Two Weeks of Antituberculosis Therapy", PLOS ONE, 2012, 7(10): e46191, pp. 1-13.
Cai et al., "Increased Complement C1q Level Marks Active Disease in Human Tuberculosis", PLOS ONE, 2014, 9(3): e92340, pp. 1-11.
Cliff et al., "Distinct Phases of Blood Gene Expression Pattern Through Tuberculosis Treatment Reflect Modulation of the Humoral Immune Response", The Journal of Infectious Diseases, 2013, 207:18-29.
Dawany et al., "Identification of a 251 Gene Expression Signature That Can Accurately Detect M. tuberculosis in Patients with and without HIV Co-Infection", PLOS ONE, 2014, 9(2): e89925, pp. 1-8.
Desvignes et al., "STIM1 controls T cell-mediated immune regulation and inflammation in chronic infection", The Journal of Clinical Investigation, 2015, 125(6):2347-2362.
Gavin et al., "Host Responses to Melioidosis and Tuberculosis Are Both Dominated by Interferon-Mediated Signaling", PLOS ONE, 2013, 8(1): e54961, pp. 1-13.
Kaforou et al., "Detection of Tuberculosis in HIV-Infected and-Uninfected African Adults Using Whole Blood RNA Expression Signatures: A Case-Control Study", PLOS Medicine, 2013, 10(10): e1001538, pp. 1-17.
Maertzdorf et al., "Common patterns and disease-related signatures in tuberculosis and sarcoidosis", PNAS, 2012, 109(20): 7853-7858.
Maertzdorf et al., "Concise gene signature for point-of-care classification of tuberculosis", EMBO Molecular Medicine, 2016, 8(2): 86-95.
Maertzdorf et al., "Functional Correlations of Pathogenesis-Driven Gene Expression Signatures in Tuberculosis", PLOS ONE, 2011, 6(10): e26938, pp. 1-8.

(Continued)

*Primary Examiner* — James Martinell
(74) *Attorney, Agent, or Firm* — James S. Keddie; Bozicevic, Field & Francis LLP

(57) ABSTRACT

Methods for diagnosis of tuberculosis are disclosed. In particular, the invention relates to the use of a panel of biomarkers for aiding diagnosis, prognosis, and treatment of tuberculosis. The identified biomarkers can be used to detect active tuberculosis as well as to distinguish active tuberculosis from latent tuberculosis and other pulmonary and infectious diseases, and for monitoring responses to treatment.

15 Claims, 61 Drawing Sheets

(56) References Cited

OTHER PUBLICATIONS

McIlleron et al., "Determinants of Rifampin, Isoniazid, Pyrazinamide, and Ethambutol Pharmacokinetics in a Cohort of Tuberculosis Patients", Antimicrobial Agents and Chemotherapy, 2006, 50(4): 1170-1177.

Ottenhoff et al., "Genome-Wide Expression Profiling Identifies Type 1 Interferon Response Pathways in Active Tuberculosis", PLOS ONE, 2012, 7(9): e45839, pp. 1-12.

Sweeney et al., "Genome-wide expression for diagnosis of pulmonary tuberculosis: a multicohort analysis", Lancet Respir Med., 2016, 4(3): 213-224. doi:10.1016/S2213-2600(16)00048-5.

Tientcheu et al, "Differential transcriptomic and metabolic profiles of M. africanum- and M. tuberculosis-infected patients after, but not before drug treatment", Genes Immun., 2015, 16(5): 347-355. doi:10.1038/gene.2015.21.

Verhagen et al, "A predictive signature gene set for discriminating active from latent tuberculosis in Warao Amerindian children", BMC Genomics, 2013, 14:74, 11 pages.

Wu et al, "Systematic Expression Profiling Analysis Identifies Specific MicroRNA-Gene Interactions that May Differentiate between Active and Latent Tuberculosis Infection", BioMed Research International, 2014, vol. 2014, Article ID 895179, 9 pages.

Warsinske et al., "Assessment of Validity of a Blood-Based 3-Gene Signature Score for Progression and Diagnosis of Tuberculosis, Disease Severity, and Treatment Response", JAWA Network Open, 2018, 1(6):e183779, XP55579029.

\* cited by examiner

METHODS FOR DIAGNOSIS OF TUBERCULOSIS

CROSS-REFERENCE TO RELATED APPLICATIONS

This application is a § 371 national phase of International Application No. PCT/US2016/057145, filed on Oct. 14, 2016, which claims the benefit of U.S. Application Ser. No. 62/241,506, filed on Oct. 14, 2015, which applications are incorporated by reference herein.

STATEMENT REGARDING FEDERALLY SPONSORED RESEARCH OR DEVELOPMENT

This invention was made with Government support under contracts LM007033, AI109662, and AI057229 awarded by the National Institutes of Health. The Government has certain rights in the invention.

TECHNICAL FIELD

The present invention pertains generally to methods for diagnosis of tuberculosis. In particular, the invention relates to biomarkers that can be used to detect active tuberculosis and distinguish active tuberculosis from latent tuberculosis and other pulmonary and infectious diseases.

BACKGROUND

Tuberculosis (TB) is a worldwide public health issue, with 9 million new infections and 1.5 million deaths in 2013 (Global Tuberculosis Programme, World Health Organization. Global tuberculosis report. Geneva, Switzerland: World Health Organisation; 2012: volumes). Despite advances in diagnosis and treatment, there is still a large burden of disease. TB is difficult to accurately diagnose; traditional methods such as tuberculin skin testing and interferon gamma release assays (IGRAs) are unable to distinguish between latent TB (LTB) and active TB (ATB), and have lower sensitivity in HIV-positive patients[2]. Although the Xpert MTB/RIF assay has significantly improved diagnostic power, it suffers from reduced accuracy in HIV-positive patients, and is not useful for monitoring treatment response (Steingart et al. (2014) Cochrane Database Syst. Rev. 1: CD009593; Friedrich et al. (2013) Lancet Respir. Med 1:462-470). Further, it relies on induced sputum, which can be difficult to obtain from adults after symptomatic improvement or from pediatric patients at any time. Current methods could thus potentially be complemented by an accurate, HIV-invariant blood-based diagnostic and treatment-response test.

Several studies have investigated the host response to tuberculosis infection using microarray-based whole genome expression profiles in peripheral blood. However, the results from these studies have not translated into clinical practice so far, due largely to poor generalizability. For instance, different gene signatures, with minimal overlap, have been proposed for distinguishing ATB from other diseases (OD) or LTB (REF Nature and PloS Medicine) and in children and adults (Anderson et al. (2014) N. Engl. J. Med. 370:1712-1723; Kaforou et al. (2014) J. Infect 69 Suppl. 1:S28-31). Many of these studies have now been deposited in publically accessible databases such as the NIH Gene Expression Omnibus (GEO), allowing their further analysis and re-use.

There remains a need for sensitive and specific diagnostic tests for tuberculosis that can distinguish between latent and active disease and better methods of monitoring responses to treatment.

SUMMARY

The invention relates to the use of biomarkers for diagnosis of tuberculosis. In particular, the inventors have discovered biomarkers that can be used to detect active tuberculosis and distinguish active tuberculosis from latent tuberculosis and other pulmonary and infectious diseases. These biomarkers can be used alone or in combination with one or more additional biomarkers or relevant clinical parameters in prognosis, diagnosis, or monitoring treatment of tuberculosis.

In one aspect, the invention includes a method for diagnosing and treating a patient suspected of having tuberculosis, the method comprising: a) obtaining a biological sample from the patient; b) measuring the levels of expression of a set of genes that are overexpressed in patients who have active tuberculosis and a set of genes that are underexpressed in patients who have active tuberculosis in the biological sample, wherein the set of genes that are overexpressed in patients who have active tuberculosis comprises one or more genes selected from the group consisting of AIM2, ALDH1A1, ANKRD22, ASGR1, BATF2, BRSK1, C5, CD274, CNDP2, C1QB, DUSP3, FAM26F, FAM111A, GBP1, GBP2, GBP4, GBP5, GPBAR1, HLA-DMA, KCNJ2, LHFPL2, MOV10, P2RY14, PRPS2, PSMB9, PSME2, RARRES3, SCO2, TAP2, TAPBPL, USF1, VAMP5, and WDFY1, and the set of genes that are underexpressed in patients who have active tuberculosis comprises one or more genes selected from the group consisting of AP1M1, ARHGEF18, BANK1, BLK, CD79A, CD79B, COL9A2, EML4, FNBP1, GNG7, HLA-DOB, IL27RA, KLF2, MAP7, MCM5, NOV, ORAI1, OSBPL10, OXSR1, PITPNC1, PNOC, PPIA, PPM1H, RBBP7, RNF44, SWAP70, SYTL1, TATDN2, TPK1, and TRIM28; and c) diagnosing the patient with active tuberculosis by analyzing the levels of expression of each biomarker in conjunction with respective reference value ranges for a control subject, wherein increased levels of expression of the set of genes that are overexpressed in patients who have active tuberculosis compared to the reference value ranges for the control subject in combination with decreased levels of expression of the set of genes that are underexpressed in patients who have active tuberculosis compared to the reference value ranges for the control subject indicate that the patient has active tuberculosis; and d) administering an effective amount of at least one antibiotic to the patient if the patient is diagnosed with active tuberculosis.

In certain embodiments, the set of genes that are overexpressed in patients who have active tuberculosis and the set of genes that are underexpressed in patients who have active tuberculosis are selected from the group consisting of: a) a set of genes that are overexpressed in patients who have active tuberculosis comprising GBP5 and DUSP3 and a set of genes that are underexpressed in patients who have active tuberculosis comprising KLF2; b) a set of genes that are overexpressed in patients who have active tuberculosis comprising GBP6, HLA-DMA, and TAPBPL and a set of genes that are underexpressed in patients who have active tuberculosis comprising TPK1, CD79B, and AP1M1; c) a set of genes that are overexpressed in patients who have active tuberculosis comprising ANKRD22, ASGR1, and C5 and a set of genes that are underexpressed in patients who have active tuberculosis comprising OXSR1; d) a set of genes that are overexpressed in patients who have active tuberculosis comprising BATF2, RARRES3, and ALDH1A1 and a set of genes that are underexpressed in patients who have active tuberculosis comprising ORAI1, RBBP7, and HLA-DOB; e) a set of genes that are overexpressed in patients who have active tuberculosis comprising VAMP5, PSME2, and USF1 and a set of genes that are underexpressed in patients who have active tuberculosis comprising TATDN2, CD79A, and COL9A2; f) a set of genes that are overexpressed in patients who have active tuberculosis comprising GBP2, FAM111A, and BRSK1 and a set of genes that are underexpressed in patients who have active tuberculosis comprising FNBP1, MAP7, and IL27RA; g) a set of genes that are overexpressed in patients who have active tuberculosis comprising WDFY1 and a set of genes that are underexpressed in patients who have active tuberculosis comprising EML4, BANK1, and PITPNC1; h) a set of genes that are overexpressed in patients who have active tuberculosis comprising GBP1 and GPBAR1 and a set of genes that are underexpressed in patients who have active tuberculosis comprising OSBPL10, NOV, and MCM5; i) a set of genes that are overexpressed in patients who have active tuberculosis comprising CD274, SCO2, and KCNJ2 and a set of genes that are underexpressed in patients who have active tuberculosis comprising GNG7 and PPM1H; j) a set of genes that are overexpressed in patients who have active tuberculosis comprising AIM2, GBP4, and PRPS2 and a set of genes that are underexpressed in patients who have active tuberculosis comprising PNOC and RNF44; k) a set of genes that are overexpressed in patients who have active tuberculosis comprising PSMB9, CNDP2, TAP2, and FAM26F and a set of genes that are underexpressed in patients who have active tuberculosis comprising ARHGEF18, SWAP70, and SYTL1; and 1) a set of genes that are overexpressed in patients who have active tuberculosis comprising LHFPL2, MOV10, C1QB, and P2RY14 and a set of genes that are underexpressed in patients who have active tuberculosis comprising TRIM28, BLK, and PPIA.

In another embodiment, the invention includes a method for diagnosing and treating tuberculosis in a patient, the method comprising: a) obtaining a biological sample from the patient; b) measuring levels of expression of GBP5, DUSP3, and KLF2 biomarkers in the biological sample; c) diagnosing the patient with tuberculosis by analyzing the levels of expression of each biomarker in conjunction with respective reference value ranges for the biomarkers, wherein increased levels of expression of the GBP5 and DUSP3 biomarkers compared to the reference value ranges for the biomarkers for a control subject in combination with a decreased level of expression of the KLF2 biomarker compared to reference value ranges of the biomarker for a control subject indicate that the patient has active tuberculosis; and d) administering an effective amount of at least one antibiotic to the patient if the patient is diagnosed with active tuberculosis.

In another embodiment, the method further comprises determining a TB score for the patient as described herein, wherein a higher TB score for the patient compared to reference value ranges for a control subject indicates that the patient has active tuberculosis.

Reference value ranges can represent the levels of expression of one or more biomarkers found in one or more samples of one or more subjects without active tuberculosis (e.g., healthy subject, non-infected subject, or subject with latent tuberculosis). Alternatively, the reference value ranges can represent the levels of expression of one or more biomarkers found in one or more samples of one or more subjects with active tuberculosis. In certain embodiments, the levels of expression of the biomarkers in a biological sample from a subject are compared to reference values for subjects with latent or active tuberculosis or other pulmonary or infectious diseases.

Antibiotics that may be used in treating tuberculosis include, but are not limited to, ethambutol, isoniazid, pyrazinamide, rifabutin, rifampin, rifapentine, amikacin, capreomycin, cycloserine, ethionamide, levofloxacin, moxifloxacin, para-aminosalicylic acid, and streptomycin.

Methods of the invention, as described herein, can be used to determine if the patient has active tuberculosis and to distinguish a diagnosis of active tuberculosis from latent tuberculosis and other pulmonary conditions or infectious diseases. In addition, the levels of expression of the biomarkers can be used to evaluate disease severity, wherein increasing levels of expression of a set of genes that are overexpressed in patients who have active tuberculosis (e.g., GBP5 and DUSP3) and decreasing levels of expression of a set of genes that are underexpressed in patients who have active tuberculosis (e.g., KLF2) correlate with worsening tuberculosis infection; and decreasing levels of expression of a set of genes that are overexpressed in patients who have active tuberculosis (e.g., GBP5 and DUSP3) and increasing levels of expression of a set of genes that are underexpressed in patients who have active tuberculosis (e.g., KLF2) correlate with recovery from active tuberculosis. Alternatively, a TB score can be used to evaluate disease severity, wherein an increasing TB score correlates with worsening tuberculosis infection and a decreasing TB score correlates with recovery from active tuberculosis.

In certain embodiments, the biological sample comprises blood, sputum, or immune cells (e.g., monocytes or macrophages).

Biomarker polynucleotides (e.g., coding transcripts) can be detected, for example, by microarray analysis, polymerase chain reaction (PCR), reverse transcriptase polymerase chain reaction (RT-PCR), Northern blot, or serial analysis of gene expression (SAGE).

In another embodiment, measuring the levels of expression of the biomarkers comprises measuring amounts of a first in vitro complex comprising a first labeled probe hybridized to a nucleic acid comprising a GBP5 biomarker gene sequence, a second in vitro complex comprising a second labeled probe hybridized to a nucleic acid comprising a DUSP3 biomarker gene sequence, and a third in vitro complex comprising a third labeled probe hybridized to a nucleic acid comprising a KLF2 biomarker gene sequence to determine the levels of expression of the GBP5, DUSP3, and KLF2 biomarkers in the biological sample.

In another embodiment, the invention includes a method for monitoring the efficacy of a therapy for treating a tuberculosis infection in a patient, the method comprising: a) obtaining a first biological sample from the patient before the patient undergoes said therapy and a second biological sample after the patient undergoes said therapy; b) measuring levels of expression of GBP5, DUSP3, and KLF2 biomarkers in the first biological sample and the second biological sample; and c) analyzing the levels of expression of the GBP5, DUSP3, and KLF2 biomarkers in conjunction with respective reference value ranges for the biomarkers wherein decreased levels of expression of the GBP5 and DUSP3 biomarkers and an increased level of expression of the KLF2 biomarker in the second biological sample compared to the levels of expression of the GBP5, DUSP3, and KLF2 biomarkers in the first biological sample indicate that the tuberculosis infection in the patient is improving and increased levels of expression of the GBP5 and DUSP3 biomarkers and a decreased level of expression of the KLF2 biomarker in the second biological sample compared to the levels of expression of the GBP5, DUSP3, and KLF2 biomarkers in the first biological sample indicate that the tuberculosis infection in the patient is worsening or not responding to the therapy.

In another embodiment, the invention includes a method for monitoring the efficacy of a therapy for treating a tuberculosis infection in a patient, the method comprising: a) obtaining a first biological sample from the patient before the patient undergoes said therapy and a second biological sample after the patient undergoes said therapy; b) measuring levels of expression of GBP5, DUSP3, and KLF2 biomarkers in the first biological sample and the second biological sample; and c) calculating TB scores based on the levels of expression of the GBP5, DUSP3, and KLF2 biomarkers in the first biological sample and the second biological sample, wherein a lower TB score for the second biological sample compared to the TB score for the first biological sample indicates that the tuberculosis infection in the patient is improving and a higher TB score for the second biological sample compared to the TB score for the first biological sample indicates that the tuberculosis infection in the patient is worsening or not responding to the therapy.

In another embodiment, the invention includes a method for distinguishing active tuberculosis from latent tuberculosis, the method comprising: a) obtaining a biological sample from a patient; b) measuring the levels of expression of GBP5, DUSP3, and KLF2 biomarkers; and c) analyzing the levels of expression of the GBP5, DUSP3, and KLF2 biomarkers in conjunction with respective reference value ranges for said biomarkers, wherein similarity of the levels of expression of the GBP5, DUSP3, and KLF2 biomarkers to reference value ranges for a subject with active tuberculosis indicate that the patient has active tuberculosis, and wherein similarity of the levels of expression of the GBP5, DUSP3, and KLF2 biomarkers to reference value ranges for a subject with latent tuberculosis indicate that the patient has latent tuberculosis.

In another embodiment, the invention includes a method of monitoring a tuberculosis infection in a subject, the method comprising: a) measuring levels of expression of GBP5, DUSP3, and KLF2 biomarkers in a first biological sample from the subject, wherein the first biological sample is obtained from the subject at a first time point; b) measuring levels of expression of GBP5, DUSP3, and KLF2 biomarkers in a second biological sample from the subject, wherein the second biological sample is obtained from the subject at a second time point (i.e., later); and c) comparing the levels of expression of the biomarkers in the first biological sample to the levels of expression of the biomarkers in the second biological sample, wherein decreased levels of expression of the GBP5 and DUSP3 biomarkers and an increased level of expression of the KLF2 biomarker in the second biological sample compared to the levels of expression of the biomarkers in the first biological sample indicate that the tuberculosis infection in the patient is improving and increased levels of expression of the GBP5 and DUSP3 biomarkers and a decreased level of expression of the KLF2 biomarker in the second biological sample compared to the levels of expression of the biomarkers in the first biological sample indicate that the tuberculosis infection in the patient is worsening.

In another embodiment, the invention includes a method of monitoring a tuberculosis infection in a subject, the method comprising: a) measuring levels of expression of GBP5, DUSP3, and KLF2 biomarkers in a first biological sample from the subject, wherein the first biological sample is obtained from the subject at a first time point; b) measuring levels of expression of GBP5, DUSP3, and KLF2 biomarkers in a second biological sample from the subject, wherein the second biological sample is obtained from the subject at a second time point; and c) calculating TB scores based on the levels of expression of the GBP5, DUSP3, and KLF2 biomarkers in the first biological sample and the second biological sample, wherein a lower TB score for the second biological sample compared to the TB score for the first biological sample indicates that the tuberculosis infection in the patient is improving and a higher TB score for the second biological sample compared to the TB score for the first biological sample indicates that the tuberculosis infection in the patient is worsening.

In another embodiment, the invention includes a method for distinguishing active tuberculosis from latent tuberculosis, the method comprising: a) obtaining a biological sample from a patient; b) measuring levels of expression of GBP5, DUSP3, and KLF2 biomarkers in the biological sample; and c) analyzing levels of expression of each biomarker in conjunction with respective reference value ranges for each biomarker, wherein similarity of the level of expression of GBP5, DUSP3, and KLF2 to reference value ranges for a subject with active tuberculosis indicates that the patient has active tuberculosis, and wherein similarity of the level of expression of GBP5, DUSP3, and KLF2 to reference value ranges for a subject with latent tuberculosis indicates that the patient has latent tuberculosis.

In another embodiment, the invention includes a method for treating a patient suspected of having tuberculosis, the method comprising: a) receiving information regarding the diagnosis of the patient according to a method described herein; and b) administering a therapeutically effective amount of at least one antibiotic (e.g., rifampicin, isoniazid, pyrazinamide, or ethambutol) to the patient if the patient has a positive tuberculosis diagnosis. After treatment, the method may further comprise monitoring the response of the patient to treatment.

In another embodiment, the invention includes a method for treating a patient suspected of having tuberculosis, the method comprising: a) diagnosing the patient according to a method described herein; and b) administering a therapeutically effective amount of at least one antibiotic (e.g., rifampicin, isoniazid, pyrazinamide, or ethambutol) to the patient if the patient has a positive tuberculosis diagnosis.

In another embodiment, the invention includes a biomarker panel comprising GBP5, DUSP3, and KLF2 biomarkers.

In another aspect, the invention includes a kit for diagnosing tuberculosis in a subject. The kit may include a container for holding a biological sample isolated from a human subject suspected of having tuberculosis, at least one agent that specifically detects a tuberculosis biomarker; and printed instructions for reacting the agent with the biological sample or a portion of the biological sample to detect the presence or amount of at least one tuberculosis biomarker in the biological sample. The agents may be packaged in separate containers. The kit may further comprise one or more control reference samples and reagents for performing PCR or microarray analysis for detection of biomarkers as described herein.

In certain embodiments, the kit includes agents for detecting polynucleotides of a biomarker panel comprising a plurality of biomarkers for diagnosing tuberculosis, wherein one or more biomarkers are selected from the group consisting of a GBP5 polynucleotide, a DUSP3 polynucleotide, and a KLF2 polynucleotide. In one embodiment, the kit includes agents for detecting biomarkers of a biomarker panel comprising GBP5, DUSP3, and KLF2 biomarkers.

In certain embodiments, the kit comprises a microarray for analysis of a plurality of biomarker polynucleotides. In one embodiment, the kit comprises a microarray comprising an oligonucleotide that hybridizes to a GBP5 polynucleotide, an oligonucleotide that hybridizes to a DUSP3 polynucleotide, and an oligonucleotide that hybridizes to a KLF2 polynucleotide.

In another embodiment, the kit comprises agents for detecting expression levels of a set of genes that are overexpressed in patients who have active tuberculosis and a set of genes that are underexpressed in patients who have active tuberculosis selected from the group consisting of: a) a set of genes that are overexpressed in patients who have active tuberculosis comprising GBP5 and DUSP3 and a set of genes that are underexpressed in patients who have active tuberculosis comprising KLF2; b) a set of genes that are overexpressed in patients who have active tuberculosis comprising GBP6, HLA-DMA, and TAPBPL and a set of genes that are underexpressed in patients who have active tuberculosis comprising TPK1, CD79B, and AP1M1; c) a set of genes that are overexpressed in patients who have active tuberculosis comprising ANKRD22, ASGR1, and C5 and a set of genes that are underexpressed in patients who have active tuberculosis comprising OXSR1; d) a set of genes that are overexpressed in patients who have active tuberculosis comprising BATF2, RARRES3, and ALDH1A1 and a set of genes that are underexpressed in patients who have active tuberculosis comprising ORAI1, RBBP7, and HLA-DOB; e) a set of genes that are overexpressed in patients who have active tuberculosis comprising VAMPS, PSME2, and USF1 and a set of genes that are underexpressed in patients who have active tuberculosis comprising TATDN2, CD79A, and COL9A2; f) a set of genes that are overexpressed in patients who have active tuberculosis comprising GBP2, FAM111A, and BRSK1 and a set of genes that are underexpressed in patients who have active tuberculosis comprising FNBP1, MAP7, and IL27RA; g) a set of genes that are overexpressed in patients who have active tuberculosis comprising WDFY1 and a set of genes that are underexpressed in patients who have active tuberculosis comprising EML4, BANK1, and PITPNC1; h) a set of genes that are overexpressed in patients who have active tuberculosis comprising GBP1 and GPBAR1 and a set of genes that are underexpressed in patients who have active tuberculosis comprising OSBPL10, NOV, and MCM5; i) a set of genes that are overexpressed in patients who have active tuberculosis comprising CD274, SCO2, and KCNJ2 and a set of genes that are underexpressed in patients who have active tuberculosis comprising GNG7 and PPM1H; j) a set of genes that are overexpressed in patients who have active tuberculosis comprising AIM2, GBP4, and PRPS2 and a set of genes that are underexpressed in patients who have active tuberculosis comprising PNOC and RNF44; k) a set of genes that are overexpressed in patients who have active tuberculosis comprising PSMB9, CNDP2, TAP2, and FAM26F and a set of genes that are underexpressed in patients who have active tuberculosis comprising ARHGEF18, SWAP70, and SYTL1; and 1) a set of genes that are overexpressed in patients who have active tuberculosis comprising LHFPL2, MOV10, C1QB, and P2RY14 and a set of genes that are underexpressed in patients who have active tuberculosis comprising TRIM28, BLK, and PPIA.

In another aspect, the invention includes a diagnostic system comprising a storage component (i.e., memory) for storing data, wherein the storage component has instructions for determining the diagnosis of the patient stored therein; a computer processor for processing data, wherein the computer processor is coupled to the storage component and configured to execute the instructions stored in the storage component in order to receive patient data and analyze patient data according to an algorithm; and a display component for displaying information regarding the diagnosis of the patient. The storage component may include instructions for calculating the TB score, as described herein (see Example 1). Additionally, the storage component may further include instructions for performing multivariate linear discriminant analysis (LDA), receiver operating characteristic (ROC) analysis, principal component analysis (PCA), ensemble data mining methods, cell specific significance analysis of microarrays (csSAM), or multi-dimensional protein identification technology (MUDPIT) analysis.

In certain embodiments, the invention includes a computer implemented method for diagnosing a patient suspected of having tuberculosis, the computer performing steps comprising: a) receiving inputted patient data comprising values for the level of a plurality of tuberculosis biomarkers in a biological sample from the patient; b) analyzing the level of a plurality of tuberculosis biomarkers and comparing with respective reference value ranges for the tuberculosis biomarkers; c) calculating a TB score for the patient based on the levels of the tuberculosis biomarkers; d) determining whether the patient has tuberculosis based on the value of the TB score; and e) displaying information regarding the diagnosis of the patient.

In certain embodiments, the inputted patient data comprises values for the levels of at least 3 tuberculosis biomarkers in a biological sample from the patient. For example, the inputted patient data may comprise values for the levels of a GBP5 polynucleotide, a DUSP3 polynucleotide, and a KLF2 polynucleotide.

In other embodiments, the inputted patient data comprises values for the levels of expression of a set of genes that are overexpressed in patients who have active tuberculosis and a set of genes that are underexpressed in patients who have active tuberculosis selected from the group consisting of: a) a set of genes that are overexpressed in patients who have active tuberculosis comprising GBP5 and DUSP3 and a set of genes that are underexpressed in patients who have active tuberculosis comprising KLF2; b) a set of genes that are overexpressed in patients who have active tuberculosis comprising GBP6, HLA-DMA, and TAPBPL and a set of genes that are underexpressed in patients who have active tuberculosis comprising TPK1, CD79B, and AP1M1; c) a set of genes that are overexpressed in patients who have active tuberculosis comprising ANKRD22, ASGR1, and C5 and a set of genes that are underexpressed in patients who have active tuberculosis comprising OXSR1; d) a set of genes that are overexpressed in patients who have active tuberculosis comprising BATF2, RARRES3, and ALDH1A1 and a set of genes that are underexpressed in patients who have active tuberculosis comprising ORAI1, RBBP7, and HLA-DOB; e) a set of genes that are overexpressed in patients who have active tuberculosis comprising VAMPS, PSME2, and USF1 and a set of genes that are underexpressed in patients who have active tuberculosis comprising TATDN2, CD79A, and COL9A2; f) a set of genes that are overexpressed in patients who have active tuberculosis comprising GBP2, FAM111A, and BRSK1 and a set of genes that are underexpressed in patients who have active tuberculosis comprising FNBP1, MAP7, and IL27RA; g) a set of genes that are overexpressed in patients who have active tuberculosis comprising WDFY1 and a set of genes that are underexpressed in patients who have active tuberculosis comprising EML4, BANK1, and PITPNC1; h) a set of genes that are overexpressed in patients who have active tuberculosis comprising GBP1 and GPBAR1 and a set of genes that are underexpressed in patients who have active tuberculosis comprising OSBPL10, NOV, and MCM5; i) a set of genes that are overexpressed in patients who have active tuberculosis comprising CD274, SCO2, and KCNJ2 and a set of genes that are underexpressed in patients who have active tuberculosis comprising GNG7 and PPM1H; j) a set of genes that are overexpressed in patients who have active tuberculosis comprising AIM2, GBP4, and PRPS2 and a set of genes that are underexpressed in patients who have active tuberculosis comprising PNOC and RNF44; k) a set of genes that are overexpressed in patients who have active tuberculosis comprising PSMB9, CNDP2, TAP2, and FAM26F and a set of genes that are underexpressed in patients who have active tuberculosis comprising ARHGEF18, SWAP70, and SYTL1; and 1) a set of genes that are overexpressed in patients who have active tuberculosis comprising LHFPL2, MOV10, C1QB, and P2RY14 and a set of genes that are underexpressed in patients who have active tuberculosis comprising TRIM28, BLK, and PPIA.

In another aspect, the invention includes a composition comprising at least one in vitro complex comprising a labeled probe hybridized to a nucleic acid comprising a biomarker GBP5, DUSP3, or KLF2 gene sequence, said labeled probe hybridized to said biomarker GBP5, DUSP3, or KLF2 gene sequence, or its complement, wherein said nucleic acid is extracted from a patient who has tuberculosis, or is an amplification product of a nucleic acid extracted from a patient who has tuberculosis. The probe may be detectably labeled with any type of label, including, but not limited to, a fluorescent label, bioluminescent label, chemiluminescent label, colorimetric label, or isotopic label (e.g., stable trace isotope or radioactive isotope). In certain embodiments, the composition is in a detection device (i.e., device capable of detecting labeled probe).

In one embodiment, the invention includes a composition comprising a first in vitro complex comprising a first labeled probe hybridized to a nucleic acid comprising a biomarker GBP5 gene sequence, a second in vitro complex comprising a second labeled probe hybridized to a nucleic acid comprising a biomarker DUSP3 gene sequence, and a third in vitro complex comprising a third labeled probe hybridized to a nucleic acid comprising a biomarker KLF2 gene sequence.

In another aspect, the invention includes a method for diagnosing tuberculosis in a patient. The method comprises: a) obtaining a biological sample from the patient; b) contacting at least one biomarker GBP5, DUSP3, or KLF2 nucleic acid from the biological sample or an amplification product of the biomarker nucleic acid with at least one labeled probe capable of detecting at least one nucleic acid comprising a biomarker GBP5, DUSP3, or KLF2 gene sequence, said labeled probe capable of hybridizing to the biomarker GBP5, DUSP3, or KLF2 gene sequence, or its complement; c) measuring at least one in vitro complex comprising a labeled probe hybridized to a nucleic acid comprising a biomarker GBP5, DUSP3, or KLF2 gene sequence to determine the level of expression of at least one biomarker nucleic acid in the biological sample; and d) analyzing the level of expression of at least one biomarker nucleic acid, wherein an increased level of expression of at least one biomarker nucleic acid comprising a GBP5 or DUSP3 gene sequence compared to reference value ranges of the biomarker nucleic acid for a control subject indicates that the patient has active tuberculosis, or a decreased level of expression of a biomarker nucleic acid comprising a KLF2 gene sequence compared to reference value ranges of the biomarker nucleic acid for a control subject indicates that the patient has active tuberculosis.

In another embodiment, the method comprises measuring amounts of a first in vitro complex comprising a first labeled probe hybridized to a nucleic acid comprising a biomarker GBP5 gene sequence, a second in vitro complex comprising a second labeled probe hybridized to a nucleic acid comprising a biomarker DUSP3 gene sequence, and a third in vitro complex comprising a third labeled probe hybridized to a nucleic acid comprising a biomarker KLF2 gene sequence to determine levels of expression of biomarker nucleic acids comprising GBP5, DUSP3, and KLF2 gene sequences in the biological sample, wherein increased levels of expression of the biomarker nucleic acids comprising GBP5 and DUSP3 gene sequences and a decreased level of expression of a biomarker nucleic acid comprising a KLF2 gene sequence compared to reference value ranges of the biomarker nucleic acids for a control subject indicate that the patient has active tuberculosis.

These and other embodiments of the subject invention will readily occur to those of skill in the art in view of the disclosure herein.

BRIEF DESCRIPTION OF THE FIGURES

FIG. 1A shows a schematic of the multi-cohort analysis pipeline. FIGS. 1B-1D shows forest plots for each of the three genes derived in the forward search, including GBP5 (FIG. 1B), DUSP3 (FIG. 1C), and KLF2 (FIG. 1D).

FIGS. 2A-2C show ROC curves in discovery cohorts showing HC (FIG. 2A), LTB (FIG. 2B), and OD (FIG. 2C) versus ATB patients. Healthy patients were not included in the multi-cohort analysis, but are shown here. FIGS. 2D and 2F show ROC curves in validation cohorts. FIG. 2D shows four validation datasets, which compared healthy controls with active TB. FIG. 2E shows four validation datasets, which compare latent TB with active TB. FIG. 2F shows three validation datasets, which compare other diseases with active TB. Violin plots with patient-level data are shown in FIGS. 5, 6, and 8.

FIG. 5C shows GSE56153, which also included healthy controls; the TB score returned to normal after treatment (Wilcoxon P=NS between cured cases and HC). FIG. 5D shows GSE62147, which also examined active *M. africanum* infections.

FIGS. 6A-6C show violin plots of GSE19491, GSE32750, and GSE42834, respectively; all comparisons to ATB significant (Wilcoxon p<1e-10). Healthy patients were not included in multi-cohort analysis but are shown here.

FIG. 10 (upper) shows genes that have not been re-centered to their global mean. FIG. 10 (lower) shows genes that have been re-centered to their global mean by subtracting the difference between the dataset mean and the global mean for each gene. Note that each gene maintains its distribution within a dataset.

FIG. 11 (upper) shows genes that have not been re-centered to their global mean. FIG. 11 (lower) shows genes that have been re-centered to their global mean by subtracting the difference between the dataset mean and the global mean for each gene. Note that each gene maintains its distribution within a dataset.

FIG. 12 (upper) shows genes that have not been re-centered to their global mean. FIG. 12 (lower) shows genes that have been re-centered to their global mean by subtracting the difference between the dataset mean and the global mean for each gene. Note that each gene maintains its distribution within a dataset.

FIG. 13A shows that the three gene set showed a significant difference between the two groups, with (FIG. 13B) an ROC AUC of 0.85.

FIG. 17A shows latent TB versus active TB; FIG. 17B shows other disease versus active TB. The gene sets were tested with the difference of arithmetic means as in the original paper.

(FIG. 18B) other disease versus active TB. Each dataset was tested using a K-nearest neighbors classifier built in GSE19491, as in the original paper. ROC curves were built from vote-count thresholds. GSE41055 is listed as 'NA' because all votes assigned both classes as LTB, so no thresholding could be done.

FIG. 19A shows latent TB versus active TB; FIG. 19B shows other disease versus active TB. Each dataset was tested using a support vector machine model built in GSE42834 using genes in the 144-transcript set, as in the original paper.

FIG. 20A shows latent TB versus active TB; FIG. 20B shows other disease versus active TB. The gene sets were tested with the difference of arithmetic means in each dataset, as in the original paper.

FIG. 21A shows latent TB versus active TB; FIG. 21B shows other disease versus active TB. Each dataset was tested against a random forest model built in GSE41055 using the 10-gene set, as in the original paper.

FIG. 22A shows latent TB versus active TB; FIG.

22B shows other disease versus active TB. This plot is supplied to allow comparison of the generalizability of the three-gene set and method to the other gene sets and methods that have been reported previously.

Figure 23A:
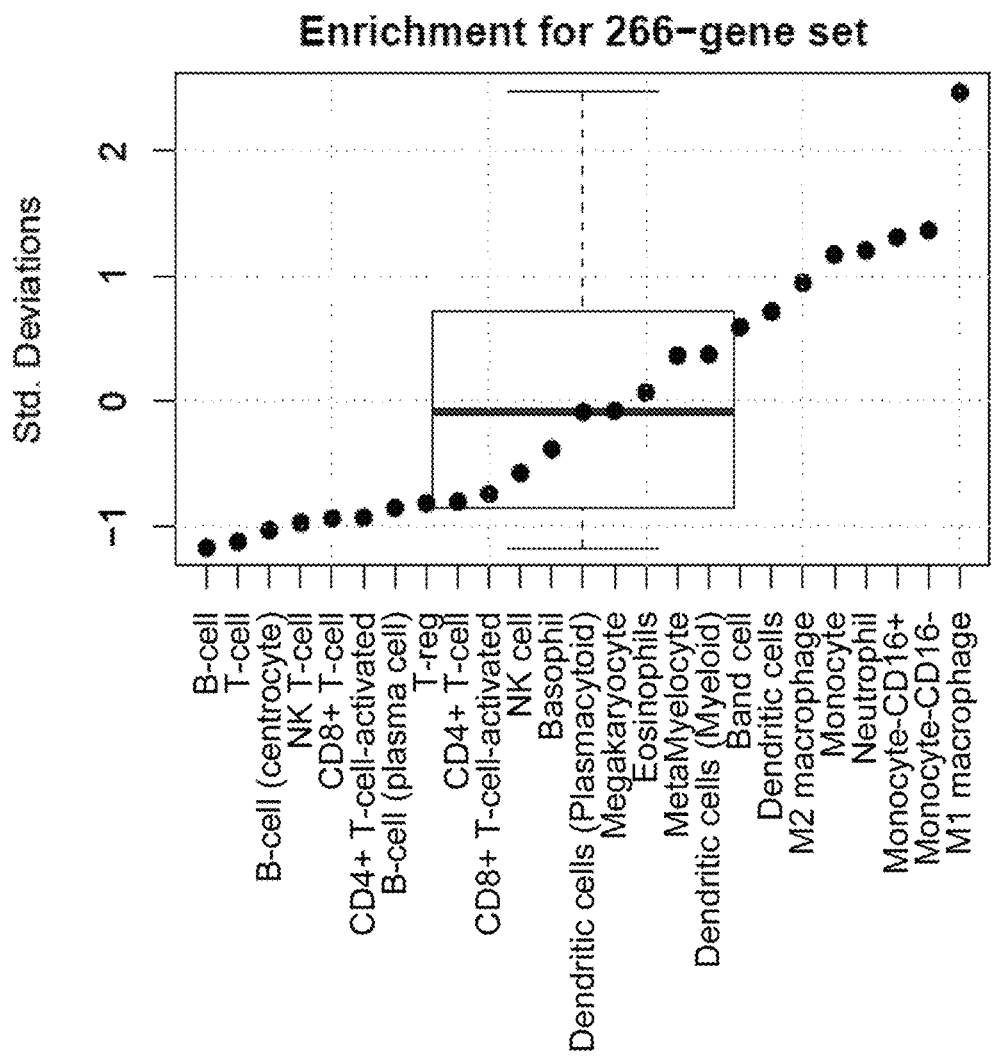
Figure 23B:
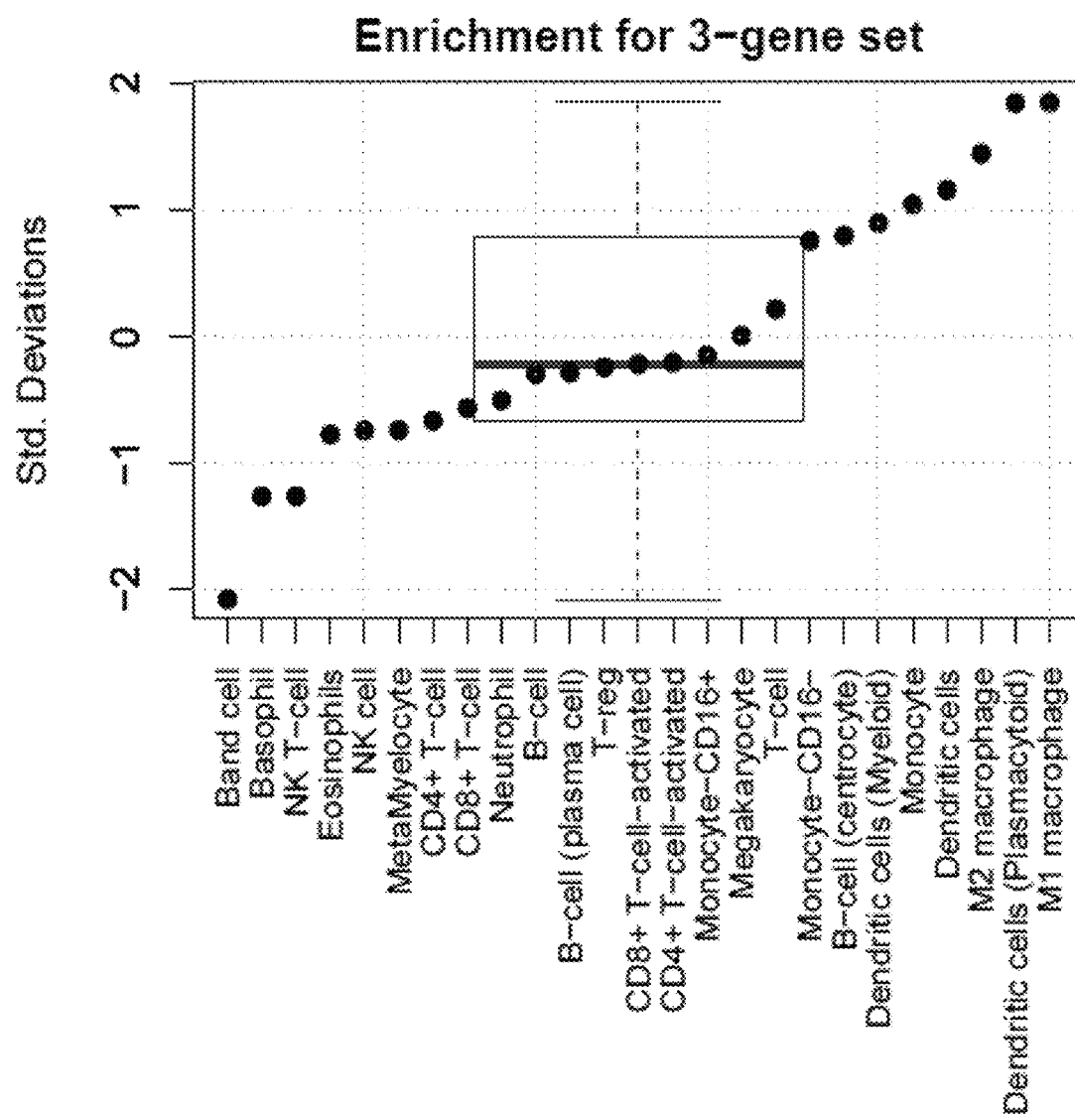

FIGS. 23A and 23B show enrichment profiles of (FIG. 23A) all 266 differentially expressed genes and (FIG. 23B) the 3 diagnostic genes in publically available sorted-cell gene expression profiles. Y-axis shows standard deviations from the mean. Both gene sets are significantly enriched in M1 macrophages compared to other cell types (p<0.05).

Figure 24A:
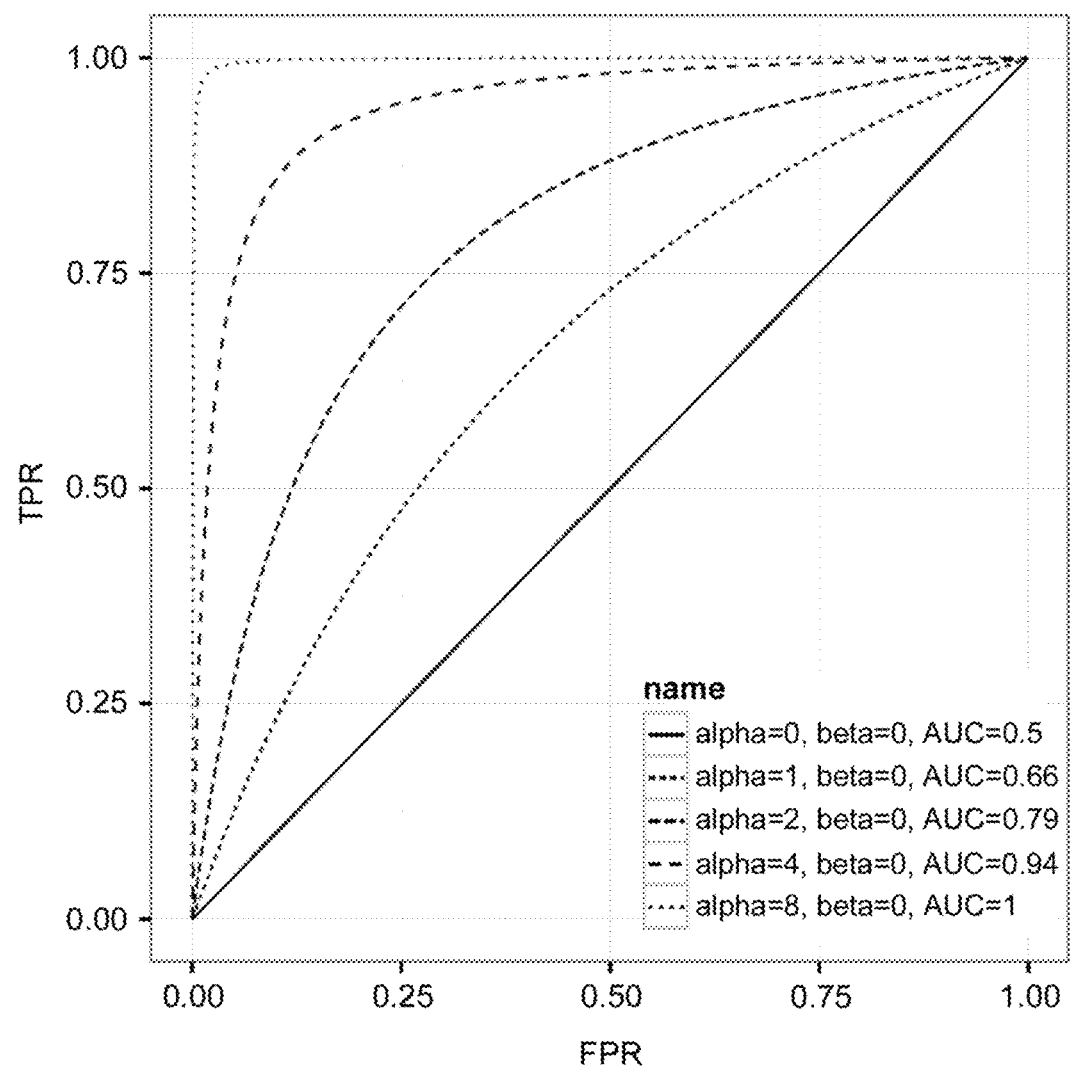
Figure 24B:
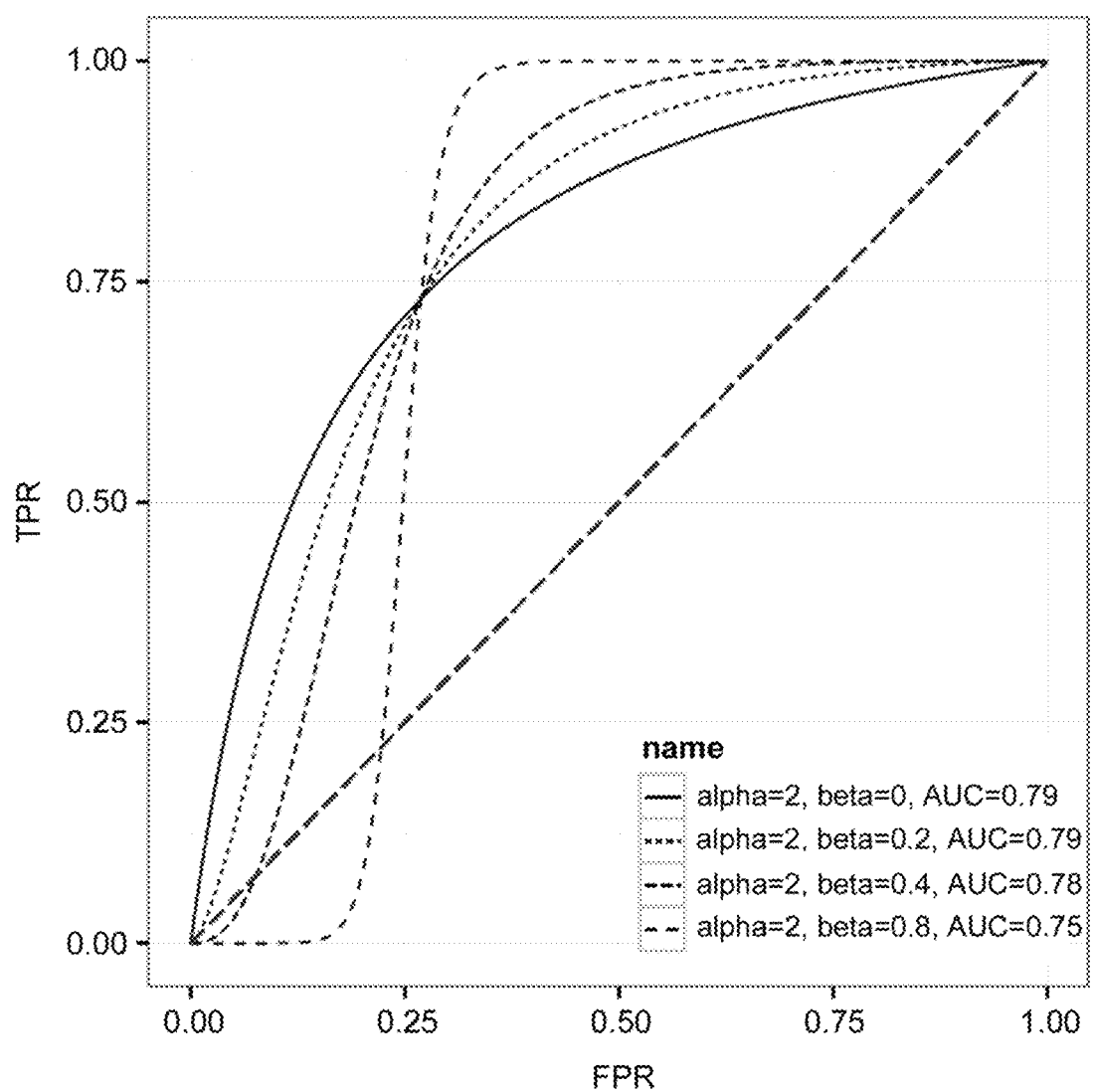

FIGS. 24A and 24B show example ROC curves constructed using the method of Kester and Buntinx for a range of (FIG. 24A) alpha and (FIG. 24B) beta, showing the effect of varying the different parameters on both ROC curve shape and AUC. For summary ROC curves, alpha and beta are calculated from a random-effects model from the contributing datasets.

DETAILED DESCRIPTION

The practice of the present invention will employ, unless otherwise indicated, conventional methods of medicine, chemistry, biochemistry, recombinant DNA techniques and immunology, within the skill of the art. Such techniques are explained fully in the literature. See, e.g., *Clinical Tuberculosis* (P. Davies, S. Gordon, and G. Davies eds., CRC Press; 5$^{th}$ edition, 2014); *Tuberculosis* (W. Rom and S. Garay eds., LWW, Second edition, 2003); *Handbook of Tuberculosis: Clinics, Diagnostics, Therapy, and Epidemiology* (S. Kaufmann and P. van Helden eds., Wiley-Blackwell, 2008); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an," and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

A "biomarker" in the context of the present invention refers to a biological compound, such as a polynucleotide or polypeptide which is differentially expressed in a sample taken from patients having tuberculosis as compared to a comparable sample taken from control subjects (e.g., a person with a negative diagnosis, normal or healthy subject, or non-infected subject). The biomarker can be a nucleic acid, a fragment of a nucleic acid, a polynucleotide, or an oligonucleotide that can be detected and/or quantified. Tuberculosis biomarkers include polynucleotides comprising nucleotide sequences from genes or RNA transcripts of genes, including but not limited to, GBP5, DUSP3, KLF2, AIM2, ALDH1A1, ANKRD22, ASGR1, BATF2, BRSK1, C5, CD274, CNDP2, C1QB, FAM26F, FAM111A, GBP1, GBP2, GBP4, GPBAR1, HLA-DMA, KCNJ2, LHFPL2, MOV10, P2RY14, PRPS2, PSMB9, PSME2, RARRES3, SCO2, TAP2, TAPBPL, USF1, VAMPS, WDFY1, AP1M1, ARHGEF18, BANK1, BLK, CD79A, CD79B, COL9A2, EML4, FNBP1, GNG7, HLA-DOB, IL27RA, MAP7, MCM5, NOV, ORAI1, OSBPL10, OXSR1, PITPNC1, PNOC, PPIA, PPM1H, RBBP7, RNF44, SWAP70, SYTL1, TATDN2, TPK1, and TRIM28, and their expression products, including guanylate binding protein 5, dual specificity phosphatase 3, Kruppel-like factor 2, interferon-inducible protein AIM2 (absent in melanoma 2), aldehyde dehydrogenase 1 family member A1, ankyrin repeat domain 22, asialoglycoprotein receptor 1, basic leucine zipper ATF-like transcription factor 2, BR serine/threonine kinase 1, complement C5, CD274 (programmed cell death 1 ligand 1), CNDP dipeptidase 2, complement C1q subcomponent subunit B, family with sequence similarity 26 member F (protein FAM26F), family with sequence similarity 111 member A (protein FAM111A), guanylate binding protein 1, guanylate binding protein 2, guanylate binding protein 4, G protein-coupled bile acid receptor 1, major histocompatibility complex class II DM alpha, potassium voltage-gated channel subfamily J member 2, lipoma HMGIC fusion partner-like 2, Mov10 RISC complex RNA helicase, purinergic receptor P2Y14, phosphoribosyl pyrophosphate synthetase 2, proteasome subunit beta 9, proteasome activator subunit 2, retinoic acid receptor responder 3, SCO2, cytochrome c oxidase assembly protein, transporter 2, ATP binding cassette subfamily B member, TAP binding protein-like protein (tapasin-related protein), upstream transcription factor 1, vesicle associated membrane protein 5, WD repeat and FYVE domain containing 1, adaptor related protein complex 1 mu 1 subunit, Rho/Rac guanine nucleotide exchange factor 18, B-cell scaffold protein with ankyrin repeats 1, BLK proto-oncogene Src family tyrosine kinase, CD79a molecule, CD79b molecule, collagen type IX alpha 2 chain, echinoderm microtubule associated protein like 4, formin binding protein 1, G protein subunit gamma 7, major histocompatibility complex, class II, DO beta, interleukin 27 receptor subunit alpha, microtubule associated protein 7, minichromosome maintenance complex component 5, nephroblastoma overexpressed protein (insulin-like growth factor-binding protein 9), ORAI calcium release-activated calcium modulator 1, oxysterol binding protein-like 10 protein, oxidative stress responsive 1, phosphatidylinositol transfer protein, cytoplasmic 1, prepronociceptin, peptidylprolyl isomerase A, protein phosphatase, $Mg^{2+}/Mn^{2+}$ dependent 1H, RB binding protein 7, chromatin remodeling factor, ring finger protein 44, SWAP switching B-cell complex 70 kDa subunit, synaptotagmin-like 1 protein, TatD DNase domain containing 2 protein, thiamin pyrophosphokinase 1, and tripartite motif containing 28 protein (transcription intermediary factor 1-beta).

The terms "polypeptide" and "protein" refer to a polymer of amino acid residues and are not limited to a minimum length. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation, hydroxylation, oxidation, and the like.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), and any other type of polynucleotide which is an N- or C-glycoside of a purine or pyrimidine base. There is no intended distinction in length between the terms "polynucleotide," "oligonucleotide," "nucleic acid" and "nucleic acid molecule," and these terms are used interchangeably.

The phrase "level of expression" refers to expression of either mRNA or protein whose abundance is measured quantitatively.

The phrase "differentially expressed" refers to differences in the quantity and/or the frequency of a biomarker present in a sample taken from patients having, for example, tuberculosis as compared to a control subject or non-infected subject. For example, a biomarker can be a polynucleotide which is present at an elevated level or at a decreased level in samples of patients with tuberculosis compared to samples of control subjects. Alternatively, a biomarker can be a polynucleotide which is detected at a higher frequency or at a lower frequency in samples of patients with tuberculosis compared to samples of control subjects. A biomarker can be differentially present in terms of quantity, frequency or both.

A polynucleotide is differentially expressed between two samples if the amount of the polynucleotide in one sample is statistically significantly different from the amount of the polynucleotide in the other sample. For example, a polynucleotide is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polynucleotide is differentially expressed in two sets of samples if the frequency of detecting the polynucleotide in samples of patients' suffering from tuberculosis, is statistically significantly higher or lower than in the control samples. For example, a polynucleotide is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

A "similarity value" is a number that represents the degree of similarity between two things being compared. For example, a similarity value may be a number that indicates the overall similarity between a patient's expression profile using specific phenotype-related biomarkers and reference value ranges for the biomarkers in one or more control samples or a reference expression profile (e.g., the similarity to an "active tuberculosis" expression profile or a "latent tuberculosis" expression profile). The similarity value may be expressed as a similarity metric, such as a correlation coefficient, or may simply be expressed as the expression level difference, or the aggregate of the expression level differences, between levels of biomarkers in a patient sample and a control sample or reference expression profile.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; and primates.

As used herein, a "biological sample" refers to a sample of tissue, cells, or fluid isolated from a subject, including but not limited to, for example, blood, buffy coat, plasma, serum, immune cells (e.g., monocytes or macrophages), sputa, fecal matter, urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components.

A "test amount" of a biomarker refers to an amount of a biomarker present in a sample being tested. A test amount can be either an absolute amount (e.g., µg/ml) or a relative amount (e.g., relative intensity of signals).

A "diagnostic amount" of a biomarker refers to an amount of a biomarker in a subject's sample that is consistent with a diagnosis of tuberculosis. A diagnostic amount can be either an absolute amount (e.g., µg/ml) or a relative amount (e.g., relative intensity of signals).

A "control amount" of a biomarker can be any amount or a range of amount which is to be compared against a test amount of a biomarker. For example, a control amount of a biomarker can be the amount of a biomarker in a person without tuberculosis. A control amount can be either in absolute amount (e.g., µg/ml) or a relative amount (e.g., relative intensity of signals).

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) J Immunology 149B:120-126); humanized antibody molecules (see, e.g., Riechmann et al. (1988) *Nature* 332:323-327; Verhoeyan et al. (1988) *Science* 239: 1534-1536; and U.K. Patent Publication No. GB 2,276,169, published 21 Sep. 1994); and, any functional fragments obtained from such molecules, wherein such fragments retain specific-binding properties of the parent antibody molecule.

"Detectable moieties," "detectable labels," or "labels" contemplated for use in the invention include any molecule capable of detection, including, but not limited to, fluorescers, chemiluminescers, chromophores, radioactive isotopes, stable trace isotopes, enzymes, enzyme substrates, enzyme cofactors, enzyme inhibitors, semiconductor nanoparticles, dyes, metal ions, metal sols, ligands (e.g., biotin, streptavidin or haptens) and the like. Detectable labels include, but are not limited to, fluorescent dyes such as fluorescein, phycoerythrin, Cy-3, Cy-5, allophycoyanin, DAPI, Texas Red, rhodamine, Oregon green, Lucifer yellow, and the like, green fluorescent protein (GFP), red fluorescent protein (DsRed), cyan fluorescent protein (CFP), yellow fluorescent protein (YFP), and Cerianthus Orange Fluorescent Protein (cOFP), enzymes, such as alkaline phosphatase (AP), beta-lactamase, chloramphenicol acetyltransferase (CAT), adenosine deaminase (ADA), aminoglycoside phosphotransferase (neo$^r$, G418r) dihydrofolate reductase (DHFR), hygromycin-B-phosphotransferase (HPH), thymidine kinase (TK), lacZ (encoding β-galactosidase), and xanthine guanine phosphoribosyltransferase (XGPRT), β-glucuronidase (gus), placental alkaline phosphatase (PLAP), secreted embryonic alkaline phosphatase (SEAP), and firefly or bacterial luciferase (LUC). Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Diagnosis" as used herein generally includes determination as to whether a subject is likely affected by a given disease, disorder or dysfunction. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

"Substantially purified" refers to nucleic acid molecules or proteins that are removed from their natural environment and are isolated or separated, and are at least about 60% free, preferably about 75% free, and most preferably about 90% free, from other components with which they are naturally associated.

As used herein, the term "probe" or "oligonucleotide probe" refers to a polynucleotide, as defined above, that contains a nucleic acid sequence complementary to a nucleic acid sequence present in the target nucleic acid analyte (e.g., biomarker). The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally.

The term "amplicon" refers to the amplified nucleic acid product of a PCR reaction or other nucleic acid amplification process (e.g., ligase chain reaction (LGR), nucleic acid sequence based amplification (NASBA), transcription-mediated amplification (TMA), Q-beta amplification, strand displacement amplification, or target mediated amplification). Amplicons may comprise RNA or DNA depending on the technique used for amplification.

The terms "hybridize" and "hybridization" refer to the formation of complexes between nucleotide sequences which are sufficiently complementary to form complexes via Watson-Crick base pairing.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "selectively detects" or "selectively detecting" refer to the detection of biomarker nucleic acids using oligonucleotides, e.g., primers or probes that are capable of detecting a particular biomarker nucleic acid, for example, by amplifying and/or binding to at least a portion of the biomarker nucleic acid, but do not amplify and/or bind to sequences from other nucleic acids under appropriate hybridization conditions.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of biomarkers that can be used in the diagnosis of tuberculosis. In particular, the inventors have shown that GBP5, DUSP3, and KLF2 biomarkers, as well as other biomarkers, can be used to detect active tuberculosis, and are useful for distinguishing active tuberculosis from latent tuberculosis and other pulmonary and infectious diseases and monitoring responses to treatment of tuberculosis (see Example 1).

In order to further an understanding of the invention, a more detailed discussion is provided below regarding the identified biomarkers associated with tuberculosis and methods of using such biomarkers in prognosis, diagnosis, or monitoring treatment of tuberculosis.

A. Biomarkers

Biomarkers that can be used in the practice of the invention include polynucleotides comprising nucleotide sequences from genes or RNA transcripts of genes, including but not limited to, GBP5, DUSP3, KLF2, AIM2, ALDH1A1, ANKRD22, ASGR1, BATF2, BRSK1, C5, CD274, CNDP2, C1QB, FAM26F, FAM111A, GBP1, GBP2, GBP4, GPBAR1, HLA-DMA, KCNJ2, LHFPL2, MOV10, P2RY14, PRPS2, PSMB9, PSME2, RARRES3, SCO2, TAP2, TAPBPL, USF1, VAMP5, WDFY1, AP1M1, ARHGEF18, BANK1, BLK, CD79A, CD79B, COL9A2, EML4, FNBP1, GNG7, HLA-DOB, IL27RA, MAP7, MCM5, NOV, ORAI1, OSBPL10, OXSR1, PITPNC1, PNOC, PPIA, PPM1H, RBBP7, RNF44, SWAP70, SYTL1, TATDN2, TPK1, and TRIM28, and their expression products, including guanylate binding protein 5, dual specificity phosphatase 3, Kruppel-like factor 2, interferon-inducible protein AIM2 (absent in melanoma 2), aldehyde dehydrogenase 1 family member A1, ankyrin repeat domain 22, asialoglycoprotein receptor 1, basic leucine zipper ATF-like transcription factor 2, BR serine/threonine kinase 1, complement C5, CD274 (programmed cell death 1 ligand 1), CNDP dipeptidase 2, complement C1q subcomponent subunit B, family with sequence similarity 26 member F (protein FAM26F), family with sequence similarity 111 member A (protein FAM111A), guanylate binding protein 1, guanylate binding protein 2, guanylate binding protein 4, G protein-coupled bile acid receptor 1, major histocompatibility complex class II DM alpha, potassium voltage-gated channel subfamily J member 2, lipoma HMGIC fusion partner-like 2, Mov10 RISC complex RNA helicase, purinergic receptor P2Y14, phosphoribosyl pyrophosphate synthetase 2, proteasome subunit beta 9, proteasome activator subunit 2, retinoic acid receptor responder 3, SCO2, cytochrome c oxidase assembly protein, transporter 2, ATP binding cassette subfamily B member, TAP binding protein-like protein (tapasin-related protein), upstream transcription factor 1, vesicle associated membrane protein 5, WD repeat and FYVE domain containing 1, adaptor related protein complex 1 mu 1 subunit, Rho/Rac guanine nucleotide exchange factor 18, B-cell scaffold protein with ankyrin repeats 1, BLK proto-oncogene Src family tyrosine kinase, CD79a molecule, CD79b molecule, collagen type IX alpha 2 chain, echinoderm microtubule associated protein like 4, formin binding protein 1, G protein subunit gamma 7, major histocompatibility complex, class II, DO beta, interleukin 27 receptor subunit alpha, microtubule associated protein 7, minichromosome maintenance complex component 5, nephroblastoma overexpressed protein (insulin-like growth factor-binding protein 9), ORAI calcium release-activated calcium modulator 1, oxysterol binding protein-like 10 protein, oxidative stress responsive 1, phosphatidylinositol transfer protein, cytoplasmic 1, prepronociceptin, peptidylprolyl isomerase A, protein phosphatase, $Mg^{2+}/Mn^{2+}$ dependent 1H, RB binding protein 7, chromatin remodeling factor, ring finger protein 44, SWAP switching B-cell complex 70 kDa subunit, synaptotagmin-like 1 protein, TatD DNase domain containing 2 protein, thiamin pyrophosphokinase 1, and tripartite motif containing 28 protein (transcription intermediary factor 1-beta). Differential expression of these biomarkers is associated with tuberculosis and therefore expression profiles of these biomarkers are useful for diagnosing tuberculosis and distinguishing active tuberculosis from latent tuberculosis and other pulmonary and infectious diseases.

Accordingly, in one aspect, the invention provides a method for diagnosing tuberculosis in a subject, comprising measuring the level of a plurality of biomarkers in a biological sample derived from a subject suspected of having tuberculosis, and analyzing the levels of the biomarkers and comparing with respective reference value ranges for the biomarkers, wherein differential expression of one or more biomarkers in the biological sample compared to one or more biomarkers in a control sample indicates that the subject has tuberculosis. When analyzing the levels of biomarkers in a biological sample, the reference value ranges used for comparison can represent the levels of one or more biomarkers found in one or more samples of one or more subjects without active tuberculosis (e.g., healthy subject, non-infected subject, or subject with latent tuberculosis). Alternatively, the reference value ranges can represent the levels of one or more biomarkers found in one or more samples of one or more subjects with active tuberculosis. In certain embodiments, the levels of the biomarkers in a biological sample from a subject are compared to reference values for subjects with latent or active tuberculosis or other pulmonary or infectious diseases.

The biological sample obtained from the subject to be diagnosed is typically blood, sputum, or immune cells (e.g., monocytes or macrophages), but can be any sample from bodily fluids, tissue or cells that contain the expressed biomarkers. A "control" sample, as used herein, refers to a biological sample, such as a bodily fluid, tissue, or cells that are not diseased. That is, a control sample is obtained from a normal or non-actively infected subject (e.g. an individual known to not have active tuberculosis). A biological sample can be obtained from a subject by conventional techniques. For example, blood can be obtained by venipuncture, and solid tissue samples can be obtained by surgical techniques according to methods well known in the art.

In certain embodiments, a panel of biomarkers is used for diagnosis of tuberculosis. Biomarker panels of any size can be used in the practice of the invention. Biomarker panels for diagnosing tuberculosis typically comprise at least 3 biomarkers and up to 30 biomarkers, including any number of biomarkers in between, such as 3, 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 3, or at least 4, or at least 5, or at least 6, or at least 7, or at least 8, or at least 9, or at least 10, or at least 11 or more biomarkers. Although smaller biomarker panels are usually more economical, larger biomarker panels (i.e., greater than 30 biomarkers) have the advantage of providing more detailed information and can also be used in the practice of the invention.

In certain embodiments, the invention includes a panel of biomarkers for diagnosing tuberculosis comprising one or more polynucleotides comprising a nucleotide sequence from a gene or an RNA transcript of a gene selected from the group consisting of GBP5, DUSP3, and KLF2. In one embodiment, the panel of biomarkers comprises a GBP5 polynucleotide, a DUSP3 polynucleotide, and a KLF2 polynucleotide.

In certain embodiments, a TB score is used for diagnosis of tuberculosis. The TB score is calculated by subtracting the mean of the expression levels of all measured biomarkers that are underexpressed compared to control reference values for the biomarkers from the mean of the expression levels of all measured biomarkers that are overexpressed compared to control reference values for the biomarkers. A higher TB score for the subject compared to reference value ranges for control subjects indicates that the subject has active tuberculosis (see Example 1).

The methods described herein may be used to determine if a patient should be treated for tuberculosis. For example, a patient is selected for treatment for tuberculosis if the patient has a positive tuberculosis diagnosis based on a biomarker expression profile or a TB score, as described herein.

In one embodiment, the invention includes a method of treating a subject having tuberculosis, the method comprising: a) diagnosing the subject with tuberculosis according to a method described herein; and b) administering a therapeutically effective amount of at least one antibiotic to the subject if the subject has a positive tuberculosis diagnosis.

In another embodiment, the invention includes a method of treating a subject suspected of having tuberculosis, the method comprising: a) receiving information regarding the diagnosis of the subject according to a method described herein; and b) administering a therapeutically effective amount of at least one antibiotic to the subject if the patient has a positive tuberculosis diagnosis.

Antibiotics that may be used in treating tuberculosis include, but are not limited to, ethambutol, isoniazid, pyrazinamide, rifabutin, rifampin, rifapentine, amikacin, capreomycin, cycloserine, ethionamide, levofloxacin, moxifloxacin, para-aminosalicylic acid, and streptomycin. Typically, several antibiotics are administered simultaneously to treat active tuberculosis, whereas a single antibiotic is administered to treat latent tuberculosis. Treatment may continue for at least a month or several months, up to one or two years, or longer, depending on whether the tuberculosis infection is active or latent. Longer treatment is generally required for severe tuberculosis infection, particularly if the infection becomes antibiotic resistant. Latent tuberculosis may be effectively treated in less time, typically 4 to 12 months, to prevent tuberculosis infection from becoming active. Subjects, whose infection is antibiotic resistant, may be screened to determine antibiotic sensitivity in order to identify antibiotics that will eradicate the tuberculosis infection. In addition, corticosteroid medicines also may be administered to reduce inflammation caused by active tuberculosis.

The methods of the invention, as described herein, can also be used for determining the prognosis of a subject and for monitoring treatment of a subject who has tuberculosis. The inventors have shown that increased levels of gene expression of certain biomarkers (e.g., GBP5 and DUSP3) and decreased levels of gene expression of other biomarkers (e.g., KLF2) correlate with disease severity (see, e.g., Examples 1 and 2 and Table 6). Thus, a medical practitioner can monitor the progress of disease by measuring the levels of the biomarkers in biological samples from the patient. For example, decreases in the levels of GBP5 and DUSP3 gene expression and increases in the level of KLF2 gene expression as compared to prior levels of GBP5, DUSP3, and KLF2 gene expression (e.g., in a biological sample collected earlier) indicate the disease in the subject is improving or has improved, whereas increases in the levels of GBP5 and DUSP3 gene expression and decreases in the level of KLF2 gene expression as compared to prior levels of GBP5, DUSP3, and KLF2 gene expression (e.g., in a biological sample collected earlier) indicate the disease in the subject has worsened or is worsening. Such worsening could indicate that the tuberculosis infection is drug-resistant and the need for an alternate treatment regimen.

Alternatively or in addition, a TB score can be used to evaluate disease severity, wherein an increasing TB score correlates with worsening tuberculosis infection and a decreasing TB score correlates with recovery from active tuberculosis.

The methods described herein for prognosis or diagnosis of subjects who have tuberculosis may be used in individuals who have not yet been diagnosed (for example, preventative screening), or who have been diagnosed, or who are suspected of having tuberculosis (e.g., display one or more characteristic symptoms), or who are at risk of developing tuberculosis (e.g., have a genetic predisposition or presence of one or more developmental, environmental, or behavioral risk factors). For example, patients having one or more risk factors including, but not limited to, patients who are immunosuppressed, immunodeficient, elderly, suspected of having had exposure to a subject infected with tuberculosis, or having symptoms of lung disease may be screened by the methods described herein. The methods may also be used to detect latent or active tuberculosis infection or evaluate severity of disease. The methods may also be used to detect the response of tuberculosis to prophylactic or therapeutic treatments or other interventions. The methods can furthermore be used to help the medical practitioner in determining prognosis (e.g., worsening, status-quo, partial recovery, or complete recovery) of the patient, and the appropriate course of action, resulting in either further treatment or observation, or in discharge of the patient from the medical care center.

In one embodiment, the invention includes a method for distinguishing active tuberculosis from latent tuberculosis. The method comprises: obtaining a biological sample from a patient and measuring levels of expression of GBP5, DUSP3, and KLF2 biomarkers in the biological sample. The levels of expression of each biomarker are analyzed in conjunction with respective reference value ranges for each biomarker. Similarity of the levels of expression of GBP5, DUSP3, and KLF2 biomarkers to reference value ranges for a subject with active tuberculosis indicates that the patient has active tuberculosis, whereas similarity of the levels of expression of the GBP5, DUSP3, and KLF2 biomarkers to reference value ranges for a subject with latent tuberculosis indicates that the patient has latent tuberculosis.

In another embodiment, the invention includes a method for monitoring the efficacy of a therapy for treating tuberculosis in a patient. The method comprises: analyzing the levels of GBP5, DUSP3, and KLF2 biomarkers in biological samples derived from the patient before and after the patient undergoes the therapy, in conjunction with respective reference levels for the biomarkers. Increasing levels of the GBP5 and DUSP3 biomarkers and a decreasing level of the KLF2 biomarker in the patient indicate that the condition of the patient is worsening and decreasing levels of the GBP5 and DUSP3 biomarkers and an increasing level of the KLF2 biomarker in the subject indicate that the condition of the patient is improving. The levels of the GBP5, DUSP3, and KLF2 biomarkers in biological samples from the patient may be compared to reference levels of the biomarkers for latent tuberculosis or active tuberculosis (e.g., at different degrees of disease severity) to evaluate the severity of the tuberculosis infection in the patient.

In another embodiment, the invention includes a method for evaluating the effect of an agent for treating tuberculosis in a patient. The method comprising: analyzing the levels of GBP5, DUSP3, and KLF2 biomarkers in biological samples derived from the patient before and after the patient is treated with the agent, and comparing the levels of the GBP5, DUSP3, and KLF2 biomarkers with respective reference levels for the biomarkers.

In another embodiment, the invention includes a method for diagnosing and treating a patient suspected of having tuberculosis, the method comprising: a) obtaining a biological sample from the patient; b) measuring the levels of expression of a set of genes that are overexpressed in patients who have active tuberculosis and a set of genes that are underexpressed in patients who have active tuberculosis in the biological sample, wherein the set of genes that are overexpressed in patients who have active tuberculosis comprises one or more genes selected from the group consisting of AIM2, ALDH1A1, ANKRD22, ASGR1, BATF2, BRSK1, C5, CD274, CNDP2, C1QB, DUSP3, FAM26F, FAM111A, GBP1, GBP2, GBP4, GBP5, GPBAR1, HLA-DMA, KCNJ2, LHFPL2, MOV10, P2RY14, PRPS2, PSMB9, PSME2, RARRES3, SCO2, TAP2, TAPBPL, USF1, VAMP5, and WDFY1, and the set of genes that are underexpressed in patients who have active tuberculosis comprises one or more genes selected from the group consisting of AP1M1, ARHGEF18, BANK1, BLK, CD79A, CD79B, COL9A2, EML4, FNBP1, GNG7, HLA-DOB, IL27RA, KLF2, MAP7, MCM5, NOV, ORAI1, OSBPL10, OXSR1, PITPNC1, PNOC, PPIA, PPM1H, RBBP7, RNF44, SWAP70, SYTL1, TATDN2, TPK1, and TRIM28; and c) diagnosing the patient with active tuberculosis by analyzing the levels of expression of each biomarker in conjunction with respective reference value ranges for a control subject, wherein increased levels of expression of the set of genes that are overexpressed in patients who have active tuberculosis compared to the reference value ranges for the control subject in combination with decreased levels of expression of the set of genes that are underexpressed in patients who have active tuberculosis compared to the reference value ranges for the control subject indicate that the patient has active tuberculosis; and d) administering an effective amount of at least one antibiotic to the patient if the patient is diagnosed with active tuberculosis.

In certain embodiments, the set of genes that are overexpressed in patients who have active tuberculosis and the set of genes that are underexpressed in patients who have active tuberculosis are selected from the group consisting of: a) a set of genes that are overexpressed in patients who have active tuberculosis comprising GBP5 and DUSP3 and a set of genes that are underexpressed in patients who have active tuberculosis comprising KLF2; b) a set of genes that are overexpressed in patients who have active tuberculosis comprising GBP6, HLA-DMA, and TAPBPL and a set of genes that are underexpressed in patients who have active tuberculosis comprising TPK1, CD79B, and AP1M1; c) a set of genes that are overexpressed in patients who have active tuberculosis comprising ANKRD22, ASGR1, and C5 and a set of genes that are underexpressed in patients who have active tuberculosis comprising OXSR1; d) a set of genes that are overexpressed in patients who have active tuberculosis comprising BATF2, RARRES3, and ALDH1A1 and a set of genes that are underexpressed in patients who have active tuberculosis comprising ORAI1, RBBP7, and HLA-DOB; e) a set of genes that are overexpressed in patients who have active tuberculosis comprising VAMP5, PSME2, and USF1 and a set of genes that are underexpressed in patients who have active tuberculosis comprising TATDN2, CD79A, and COL9A2; f) a set of genes that are overexpressed in patients who have active tuberculosis comprising GBP2, FAM111A, and BRSK1 and a set of genes that are underexpressed in patients who have active tuberculosis comprising FNBP1, MAP7, and IL27RA; g) a set of genes that are overexpressed in patients who have active tuberculosis comprising WDFY1 and a set of genes that are underexpressed in patients who have active tuberculosis comprising EML4, BANK1, and PITPNC1; h) a set of genes that are overexpressed in patients who have active tuberculosis comprising GBP1 and GPBAR1 and a set of genes that are underexpressed in patients who have active tuberculosis comprising OSBPL10, NOV, and MCM5; i) a set of genes that are overexpressed in patients who have active tuberculosis comprising CD274, SCO2, and KCNJ2 and a set of genes that are underexpressed in patients who have active tuberculosis comprising GNG7 and PPM1H; j) a set of genes that are overexpressed in patients who have active tuberculosis comprising AIM2, GBP4, and PRPS2 and a set of genes that are underexpressed in patients who have active tuberculosis comprising PNOC and RNF44; k) a set of genes that are overexpressed in patients who have active tuberculosis comprising PSMB9, CNDP2, TAP2, and FAM26F and a set of genes that are underexpressed in patients who have active tuberculosis comprising ARHGEF18, SWAP70, and SYTL1; and l) a set of genes that are overexpressed in patients who have active tuberculosis comprising LHFPL2, MOV10, C1QB, and P2RY14 and a set of genes that are underexpressed in patients who have active tuberculosis comprising TRIM28, BLK, and PPIA.

B. Detecting and Measuring Biomarkers

It is understood that the biomarkers in a sample can be measured by any suitable method known in the art. Measurement of the expression level of a biomarker can be direct or indirect. For example, the abundance levels of RNAs or proteins can be directly quantitated. Alternatively, the amount of a biomarker can be determined indirectly by measuring abundance levels of cDNAs, amplified RNAs or DNAs, or by measuring quantities or activities of RNAs, proteins, or other molecules (e.g., metabolites) that are indicative of the expression level of the biomarker. The methods for measuring biomarkers in a sample have many applications. For example, one or more biomarkers can be measured to aid in the diagnosis of tuberculosis, to determine the appropriate treatment for a subject, to monitor responses in a subject to treatment, or to identify therapeutic compounds that modulate expression of the biomarkers in vivo or in vitro.

Detecting Biomarker Polynucleotides

In one embodiment, the expression levels of the biomarkers are determined by measuring polynucleotide levels of the biomarkers. The levels of transcripts of specific biomarker genes can be determined from the amount of mRNA, or polynucleotides derived therefrom, present in a biological sample. Polynucleotides can be detected and quantitated by a variety of methods including, but not limited to, microarray analysis, polymerase chain reaction (PCR), reverse transcriptase polymerase chain reaction (RT-PCR), Northern blot, and serial analysis of gene expression (SAGE). See, e.g., Draghici *Data Analysis Tools for DNA Microarrays*, Chapman and Hall/CRC, 2003; Simon et al. *Design and Analysis of DNA Microarray Investigations*, Springer, 2004; *Real-Time PCR: Current Technology and Applications*, Logan, Edwards, and Saunders eds., Caister Academic Press, 2009; Bustin *A-Z of Quantitative PCR* (IUL Biotechnology, No. 5), International University Line, 2004; Velculescu et al. (1995) Science 270: 484-487; Matsumura et al. (2005) Cell. Microbiol. 7: 11-18; *Serial Analysis of Gene Expression (SAGE): Methods and Protocols (Methods in Molecular Biology)*, Humana Press, 2008; herein incorporated by reference in their entireties.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., tuberculosis).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., *Molecular Cloning: A Laboratory Manual* (3rd Edition, 2001). Alternatively, the solid support or surface may be a glass or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 cm$^2$ and 25 cm$^2$; however, larger arrays may also be used, e.g., in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., *PCR Protocols: A Guide To Methods And Applications*, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, or other porous or nonporous material. One method for attaching nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995); herein incorporated by reference in their entireties).

A second method for making microarrays produces high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; herein incorporated by reference in their entireties) or other methods for rapid synthesis and deposition of defined oligonucleotides (Blanchard et al., Biosensors & Bioelectronics 11:687-690; herein incorporated by reference in its entirety). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids Res. 20:1679-1684; herein incorporated by reference in its entirety), may also be used. In principle, any type of array, for example, dot blots on a nylon hybridization membrane (see Sambrook, et al., *Molecular Cloning: A Laboratory Manual,* 3rd Edition, 2001) could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123; herein incorporated by reference in their entireties. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 $cm^2$. The polynucleotide probes are attached to the support covalently at either the 3' or the 5' end of the polynucleotide.

Biomarker polynucleotides which may be measured by microarray analysis can be expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)$^+$ messenger RNA (mRNA) or a fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly(A)$^+$ RNA are well known in the art, and are described generally, e.g., in Sambrook, et al., *Molecular Cloning: A Laboratory Manual* (3rd Edition, 2001). RNA can be extracted from a cell of interest using guanidinium thiocyanate lysis followed by CsCl centrifugation (Chirgwin et al., 1979, *Biochemistry* 18:5294-5299), a silica gel-based column (e.g., RNeasy (Qiagen, Valencia, Calif.) or StrataPrep (Stratagene, La Jolla, Calif.)), or using phenol and chloroform, as described in Ausubel et al., eds., 1989, *Current Protocols In Molecular Biology,* Vol. III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. RNA can be fragmented by methods known in the art, e.g., by incubation with $ZnCl_2$, to generate fragments of RNA.

In one embodiment, total RNA, mRNA, or nucleic acids derived therefrom, are isolated from a sample taken from a tuberculosis patient. Biomarker polynucleotides that are poorly expressed in particular cells may be enriched using normalization techniques (Bonaldo et al., 1996, Genome Res. 6:791-806).

As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise polynucleotide molecules from a normal biological sample (i.e., control sample, e.g., blood from a subject not having tuberculosis) or from a tuberculosis reference biological sample, (e.g., blood from a subject having tuberculosis).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (3rd Edition, 2001), and in Ausubel et al., *Current Protocols In Molecular Biology*, vol. 2, Current Protocols Publishing, New York (1994). Typical hybridization conditions for the cDNA microarrays of Schena et al. are hybridization in 5.times.SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, *Hybridization With Nucleic Acid Probes*, Elsevier Science Publishers B.V.; and Kricka, 1992, *Nonisotopic Dna Probe Techniques*, Academic Press, San Diego, Calif. Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). Arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

In one embodiment, the invention includes a microarray comprising an oligonucleotide that hybridizes to a GBP5 polynucleotide, an oligonucleotide that hybridizes to a DUSP3 polynucleotide, and an oligonucleotide that hybridizes to a KLF2 polynucleotide.

Polynucleotides can also be analyzed by other methods including, but not limited to, northern blotting, nuclease protection assays, RNA fingerprinting, polymerase chain reaction, ligase chain reaction, Qbeta replicase, isothermal amplification method, strand displacement amplification, transcription based amplification systems, nuclease protection (S1 nuclease or RNAse protection assays), SAGE as well as methods disclosed in International Publication Nos. WO 88/10315 and WO 89/06700, and International Applications Nos. PCT/US87/00880 and PCT/US89/01025; herein incorporated by reference in their entireties.

A standard Northern blot assay can be used to ascertain an RNA transcript size, identify alternatively spliced RNA transcripts, and the relative amounts of mRNA in a sample, in accordance with conventional Northern hybridization techniques known to those persons of ordinary skill in the art. In Northern blots, RNA samples are first separated by size by electrophoresis in an agarose gel under denaturing conditions. The RNA is then transferred to a membrane, cross-linked, and hybridized with a labeled probe. Nonisotopic or high specific activity radiolabeled probes can be used, including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Isotopes that can be used include, but not limited to, $^{3}H$, $^{14}C$, $^{32}P$, $^{35}S$, $^{36}Cl$, $^{35}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and S1 nuclease assays) can be used to detect and quantitate specific mRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Serial Analysis Gene Expression (SAGE) can also be used to determine RNA abundances in a cell sample. See, e.g., Velculescu et al., 1995, Science 270:484-7; Carulli, et al., 1998, Journal of Cellular Biochemistry Supplements 30/31: 286-96; herein incorporated by reference in their entireties. SAGE analysis does not require a special device for detection, and is one of the preferable analytical methods for simultaneously detecting the expression of a large number of transcription products. First, poly $A^+$ RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system. (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

Analysis of Biomarker Data

Biomarker data may be analyzed by a variety of methods to identify biomarkers and determine the statistical significance of differences in observed levels of expression of the biomarkers between test and reference expression profiles in order to evaluate whether a patient has latent or active tuberculosis or some other pulmonary or infectious disease. In certain embodiments, patient data is analyzed by one or more methods including, but not limited to, multivariate linear discriminant analysis (LDA), receiver operating characteristic (ROC) analysis, principal component analysis (PCA), ensemble data mining methods, significance analysis of microarrays (SAM), cell specific significance analysis of microarrays (csSAM), spanning-tree progression analysis of density-normalized events (SPADE), and multi-dimensional protein identification technology (MUDPIT) analysis. (See, e.g., Hilbe (2009) Logistic Regression Models, Chapman & Hall/CRC Press; McLachlan (2004) Discriminant Analysis and Statistical Pattern Recognition. Wiley Interscience; Zweig et al. (1993) Clin. Chem. 39:561-577; Pepe (2003) The statistical evaluation of medical tests for classification and prediction, New York, N.Y.: Oxford; Sing et al. (2005) Bioinformatics 21:3940-3941; Tusher et al. (2001) Proc. Natl. Acad. Sci. U.S.A. 98:5116-5121; Oza (2006) Ensemble data mining, NASA Ames Research Center, Moffett Field, Calif., USA; English et al. (2009) J. Biomed. Inform. 42(2):287-295; Zhang (2007) Bioinformatics 8: 230; Shen-Orr et al. (2010) Journal of Immunology 184: 144-130; Qiu et al. (2011) Nat. Biotechnol. 29(10):886-891; Ru et al. (2006) J. Chromatogr. A. 1111(2): 166-174, Jolliffe Principal Component Analysis (Springer Series in Statistics, $2^{nd}$ edition, Springer, N Y, 2002), Koren et al. (2004) IEEE Trans Vis Comput Graph 10:459-470; herein incorporated by reference in their entireties.)

C. Kits

In yet another aspect, the invention provides kits for diagnosing tuberculosis, wherein the kits can be used to detect the biomarkers of the present invention. For example, the kits can be used to detect any one or more of the biomarkers described herein, which are differentially expressed in samples of a tuberculosis patient and healthy or non-infected subjects. The kit may include one or more agents for detection of biomarkers, a container for holding a biological sample isolated from a human subject suspected of having tuberculosis; and printed instructions for reacting agents with the biological sample or a portion of the biological sample to detect the presence or amount of at least one tuberculosis biomarker in the biological sample. The agents may be packaged in separate containers. The kit may further comprise one or more control reference samples and reagents for performing an immunoassay or microarray analysis.

In certain embodiments, the kit comprises agents for measuring the levels of at least three biomarkers of interest. For example, the kit may include agents for detecting biomarkers of a panel comprising a GBP5 polynucleotide, a DUSP3 polynucleotide, and a KLF2 polynucleotide. In addition, the kit may include agents for detecting more than one biomarker panel, such as two or three biomarker panels, which can be used alone or together in any combination, and/or in combination with clinical parameters for diagnosis of tuberculosis.

In certain embodiments, the kit comprises a microarray for analysis of a plurality of biomarker polynucleotides. An exemplary microarray included in the kit comprises an oligonucleotide that hybridizes to a GBP5 polynucleotide, an oligonucleotide that hybridizes to a DUSP3 polynucleotide, and an oligonucleotide that hybridizes to a KLF2 polynucleotide.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing tuberculosis.

The kits of the invention have a number of applications. For example, the kits can be used to determine if a subject has latent or active tuberculosis or some other pulmonary or infectious disease, and for monitoring responses to treatment. In another example, the kits can be used to determine if a patient should be treated for tuberculosis, for example, with antibiotics. In another example, kits can be used to monitor the effectiveness of treatment of a patient having tuberculosis. In a further example, the kits can be used to identify compounds that modulate expression of one or more of the biomarkers in in vitro or in vivo animal models to determine the effects of treatment.

In another embodiment, the kit comprises agents for detecting expression levels of a set of genes that are overexpressed in patients who have active tuberculosis and a set of genes that are underexpressed in patients who have active tuberculosis selected from the group consisting of: a) a set of genes that are overexpressed in patients who have active tuberculosis comprising GBP5 and DUSP3 and a set of genes that are underexpressed in patients who have active tuberculosis comprising KLF2; b) a set of genes that are overexpressed in patients who have active tuberculosis comprising GBP6, HLA-DMA, and TAPBPL and a set of genes that are underexpressed in patients who have active tuberculosis comprising TPK1, CD79B, and AP1M1; c) a set of genes that are overexpressed in patients who have active tuberculosis comprising ANKRD22, ASGR1, and C5 and a set of genes that are underexpressed in patients who have active tuberculosis comprising OXSR1; d) a set of genes that are overexpressed in patients who have active tuberculosis comprising BATF2, RARRES3, and ALDH1A1 and a set of genes that are underexpressed in patients who have active tuberculosis comprising ORAI1, RBBP7, and HLA-DOB; e) a set of genes that are overexpressed in patients who have active tuberculosis comprising VAMPS, PSME2, and USF1 and a set of genes that are underexpressed in patients who have active tuberculosis comprising TATDN2, CD79A, and COL9A2; f) a set of genes that are overexpressed in patients who have active tuberculosis comprising GBP2, FAM111A, and BRSK1 and a set of genes that are underexpressed in patients who have active tuberculosis comprising FNBP1, MAP7, and IL27RA; g) a set of genes that are overexpressed in patients who have active tuberculosis comprising WDFY1 and a set of genes that are underexpressed in patients who have active tuberculosis comprising EML4, BANK1, and PITPNC1; h) a set of genes that are overexpressed in patients who have active tuberculosis comprising GBP1 and GPBAR1 and a set of genes that are underexpressed in patients who have active tuberculosis comprising OSBPL10, NOV, and MCM5; i) a set of genes that are overexpressed in patients who have active tuberculosis comprising CD274, SCO2, and KCNJ2 and a set of genes that are underexpressed in patients who have active tuberculosis comprising GNG7 and PPM1H; j) a set of genes that are overexpressed in patients who have active tuberculosis comprising AIM2, GBP4, and PRPS2 and a set of genes that are underexpressed in patients who have active tuberculosis comprising PNOC and RNF44; k) a set of genes that are overexpressed in patients who have active tuberculosis comprising PSMB9, CNDP2, TAP2, and FAM26F and a set of genes that are underexpressed in patients who have active tuberculosis comprising ARHGEF18, SWAP70, and SYTL1; and 1) a set of genes that are overexpressed in patients who have active tuberculosis comprising LHFPL2, MOV10, C1QB, and P2RY14 and a set of genes that are underexpressed in patients who have active tuberculosis comprising TRIM28, BLK, and PPIA.

D. Diagnostic System and Computerized Methods for Diagnosis of Tuberculosis

In a further aspect, the invention includes a computer implemented method for diagnosing a patient suspected of having tuberculosis. The computer performs steps comprising: receiving inputted patient data comprising values for the levels of one or more tuberculosis biomarkers in a biological sample from the patient; analyzing the levels of one or more tuberculosis biomarkers and comparing with respective reference value ranges for the tuberculosis biomarkers; calculating a TB score for the patient; calculating the likelihood that the patient has tuberculosis; and displaying information regarding the diagnosis of the patient. In certain embodiments, the inputted patient data comprises values for the levels of a plurality of tuberculosis biomarkers in a biological sample from the patient.

In certain embodiments, the inputted patient data comprises values for the levels of expression of a set of genes that are overexpressed in patients who have active tuberculosis and a set of genes that are underexpressed in patients who have active tuberculosis selected from the group consisting of: a) a set of genes that are overexpressed in patients who have active tuberculosis comprising GBP5 and DUSP3 and a set of genes that are underexpressed in patients who have active tuberculosis comprising KLF2; b) a set of genes that are overexpressed in patients who have active tuberculosis comprising GBP6, HLA-DMA, and TAPBPL and a set of genes that are underexpressed in patients who have active tuberculosis comprising TPK1, CD79B, and AP1M1; c) a set of genes that are overexpressed in patients who have active tuberculosis comprising ANKRD22, ASGR1, and C5 and a set of genes that are underexpressed in patients who have active tuberculosis comprising OXSR1; d) a set of genes that are overexpressed in patients who have active tuberculosis comprising BATF2, RARRES3, and ALDH1A1 and a set of genes that are underexpressed in patients who have active tuberculosis comprising ORAI1, RBBP7, and HLA-DOB; e) a set of genes that are overexpressed in patients who have active tuberculosis comprising VAMPS, PSME2, and USF1 and a set of genes that are underexpressed in patients who have active tuberculosis comprising TATDN2, CD79A, and COL9A2; f) a set of genes that are overexpressed in patients who have active tuberculosis comprising GBP2, FAM111A, and BRSK1 and a set of genes that are underexpressed in patients who have active tuberculosis comprising FNBP1, MAP7, and IL27RA; g) a set of genes that are overexpressed in patients who have active tuberculosis comprising WDFY1 and a set of genes that are underexpressed in patients who have active tuberculosis comprising EML4, BANK1, and PITPNC1; h) a set of genes that are overexpressed in patients who have active tuberculosis comprising GBP1 and GPBAR1 and a set of genes that are underexpressed in patients who have active tuberculosis comprising OSBPL10, NOV, and MCM5; i) a set of genes that are overexpressed in patients who have active tuberculosis comprising CD274, SCO2, and KCNJ2 and a set of genes that are underexpressed in patients who have active tuberculosis comprising GNG7 and PPM1H; j) a set of genes that are overexpressed in patients who have active tuberculosis comprising AIM2, GBP4, and PRPS2 and a set of genes that are underexpressed in patients who have active tuberculosis comprising PNOC and RNF44; k) a set of genes that are overexpressed in patients who have active tuberculosis comprising PSMB9, CNDP2, TAP2, and FAM26F and a set of genes that are underexpressed in patients who have active tuberculosis comprising ARHGEF18, SWAP70, and SYTL1; and 1) a set of genes that are overexpressed in patients who have active tuberculosis comprising LHFPL2, MOV10, C1QB, and P2RY14 and a set of genes that are underexpressed in patients who have active tuberculosis comprising TRIM28, BLK, and PPIA.

In a further aspect, the invention includes a diagnostic system for performing the computer implemented method, as described. A diagnostic system may include a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for determining the diagnosis of the subject. For example, the storage component includes instructions for calculating a TB score for the subject based on biomarker expression levels, as described herein (see Example 1). In addition, the storage component may further comprise instructions for performing multivariate linear discriminant analysis (LDA), receiver operating characteristic (ROC) analysis, principal component analysis (PCA), ensemble data mining methods, cell specific significance analysis of microarrays (csSAM), or multi-dimensional protein identification technology (MUDPIT) analysis. The computer processor is coupled to the storage component and configured to execute the instructions stored in the storage component in order to receive patient data and analyze patient data according to one or more algorithms. The display component displays information regarding the diagnosis of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

In one aspect, computer is a server communicating with one or more client computers. Each client computer may be configured similarly to the server, with a processor, storage component and instructions. Each client computer may be a personal computer, intended for use by a person, having all the internal components normally found in a personal computer such as a central processing unit (CPU), display (for example, a monitor displaying information processed by the processor), CD-ROM, hard-drive, user input device (for example, a mouse, keyboard, touch-screen or microphone), speakers, modem and/or network interface device (telephone, cable or otherwise) and all of the components used for connecting these elements to one another and permitting them to communicate (directly or indirectly) with one another. Moreover, computers in accordance with the systems and methods described herein may comprise any device capable of processing instructions and transmitting data to and from humans and other computers including network computers lacking local storage capability.

Although the client computers may comprise a full-sized personal computer, many aspects of the system and method are particularly advantageous when used in connection with mobile devices capable of wirelessly exchanging data with a server over a network such as the Internet. For example, client computer may be a wireless-enabled PDA such as a Blackberry phone, Apple iPhone, Android phone, or other Internet-capable cellular phone. In such regard, the user may input information using a small keyboard, a keypad, a touch screen, or any other means of user input. The computer may have an antenna for receiving a wireless signal.

The server and client computers are capable of direct and indirect communication, such as over a network. It should be appreciated that a typical system can include a large number of connected computers, with each different computer being at a different node of the network. The network, and intervening nodes, may comprise various combinations of devices and communication protocols including the Internet, World Wide Web, intranets, virtual private networks, wide area networks, local networks, cell phone networks, private networks using communication protocols proprietary to one or more companies, Ethernet, WiFi and HTTP. Such communication may be facilitated by any device capable of transmitting data to and from other computers, such as modems (e.g., dial-up or cable), networks and wireless interfaces. The server may be a web server.

Although certain advantages are obtained when information is transmitted or received as noted above, other aspects of the system and method are not limited to any particular manner of transmission of information. For example, in some aspects, information may be sent via a medium such as a disk, tape, flash drive, DVD, or CD-ROM. In other aspects, the information may be transmitted in a non-electronic format and manually entered into the system. Yet further, although some functions are indicated as taking place on a server and others on a client, various aspects of the system and method may be implemented by a single computer having a single processor.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Multi-Cohort Analysis of Genome-Wide Expression for Diagnosis of Pulmonary Tuberculosis Introduction Active tuberculosis (ATB) is difficult to diagnose, particularly in comparison to latent TB (LTB), and other pulmonary and infectious diseases (OD). It is also difficult to effectively monitor TB treatment response. We used three publicly available peripheral blood whole genome expression datasets to discover a three-gene signature that distinguishes patients with ATB from those with LTB or OD. We further validated its diagnostic power to separate ATB from healthy controls, LTB, and OD in seven independent cohorts composed of both children and adults from nine countries. Expression of the three-gene set declined in ATB patients with treatment in four longitudinal cohorts, and was not confounded by HIV infection status, bacterial drug resistance, or BCG vaccination. Overall, our integrated multi-cohort analysis yielded a three-gene set that is robustly diagnostic for ATB, that was extensively validated in multiple independent cohorts, and that has broad clinical application for diagnosis and treatment response monitoring.

Methods

We hypothesized that integration of gene expression data from heterogeneous ATB patient populations across a wide variety of ages, countries, and inclusion criteria would yield a set of conserved genes that are indicative of ATB with excellent generalizability across cohorts. Using a systematic search, we identified 13 publically available datasets composed of 2,484 patient samples that matched inclusion criteria (Table 1) (Anderson et al. (2014) N. Engl. J. Med. 370:1712-1723, Kaforou et al. (2014) J. Infect. 69 Suppl 1:S28-31, Berry et al. (2010) Nature 466:973-977, Bloom et al. (2013) PLoS One 8:e70630; Verhagen et al. (2013) BMC Genomics 14:74, Maertzdorf et al. (2011) PLoS One 6:e26938, Ottenhoff et al. PLoS One 7:e45839, Maertzdorf et al. (2012) Proc. Natl. Acad. Sci. USA 109:7853-7858, Bloom et al. (2012) PLoS One 7:e46191, Cliff et al. (2013) J. Infect. Dis. 207:18-29, Wu et al. (2014) Biomed. Res. Int. 2014:895179, Cai et al. (2014) PLoS One 9:e92340, Dawany et al. (2014) PLoS One 9:e89925, Tientcheu et al. (2015) Genes Immun. 16(5):347-355). We applied our previously described multi-cohort analysis framework (Khatri et al. (2013) J. Exp. Med. 210:2205-2221, Sweeney et al. (2015) Sci. Transl. Med. 7:287ra271, Li et al. (2014) Acta Neuropathol. Commun. 2:93) to three of these datasets (GSE19491 (adults, Berry et al. (2010) Nature 466:973-977), GSE37250 (adults, Kaforou et al. (2014) J. Infect. 69 Suppl. 1:S28-31), and GSE42834 (adults, Bloom et al.

Figure 1A:
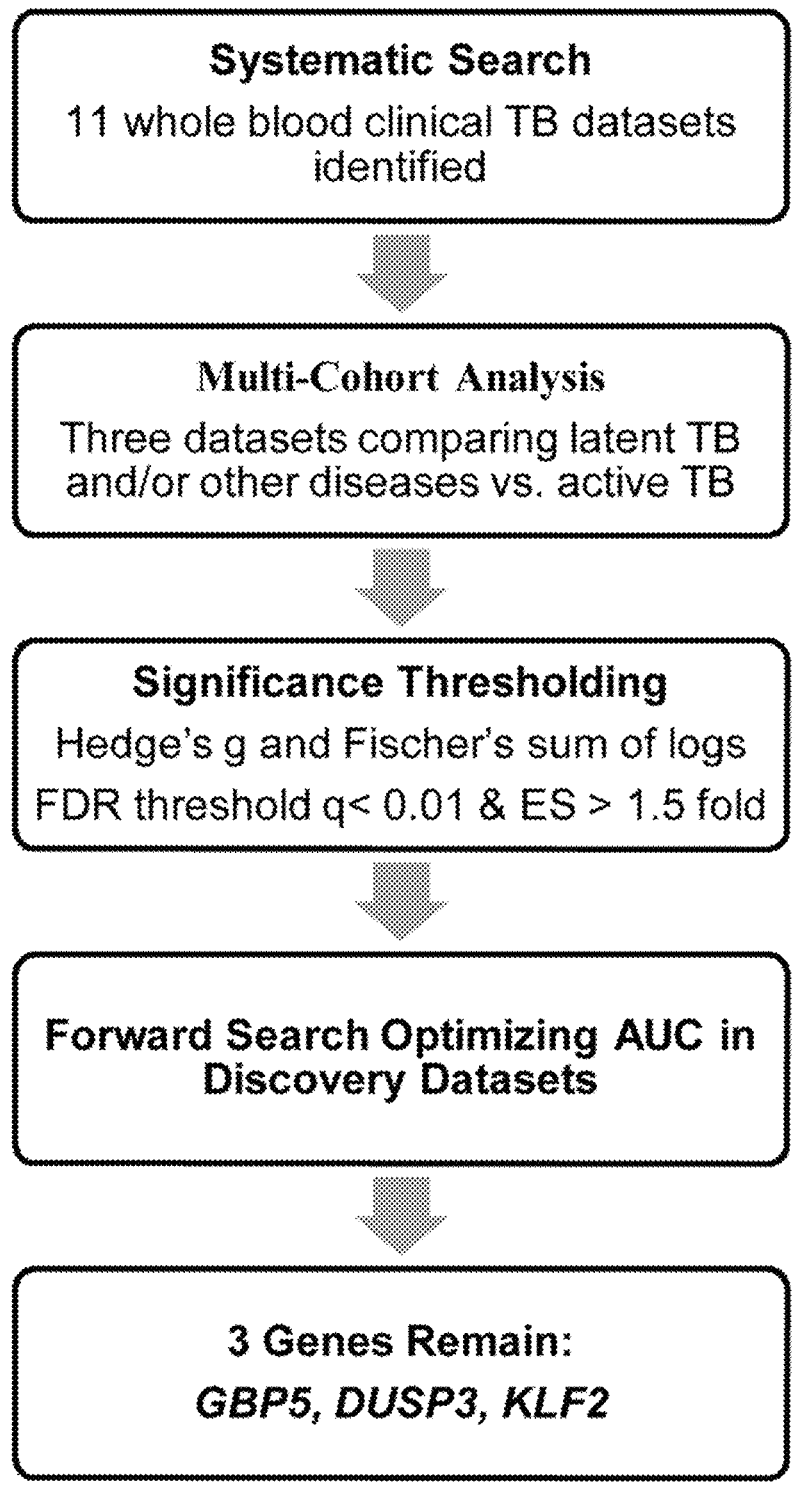
FIGS. 1A-1D show a multi-cohort analysis and three-gene set.
Figure 1B:
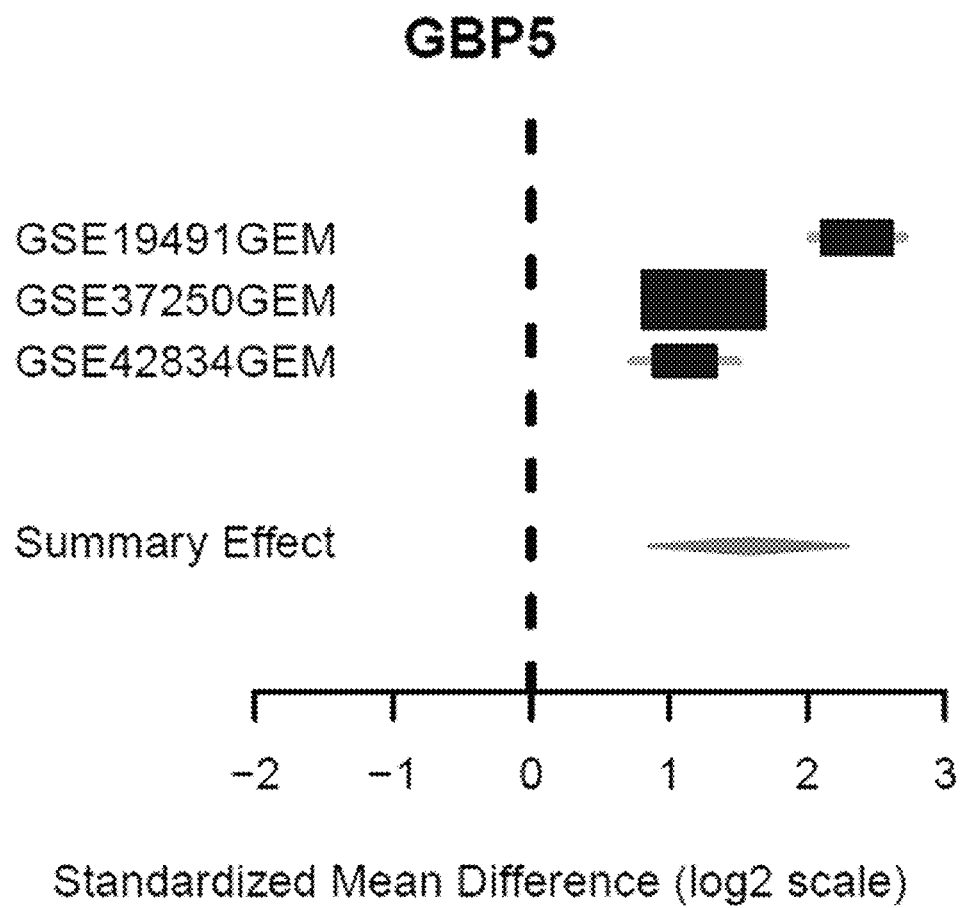
Figure 1C:
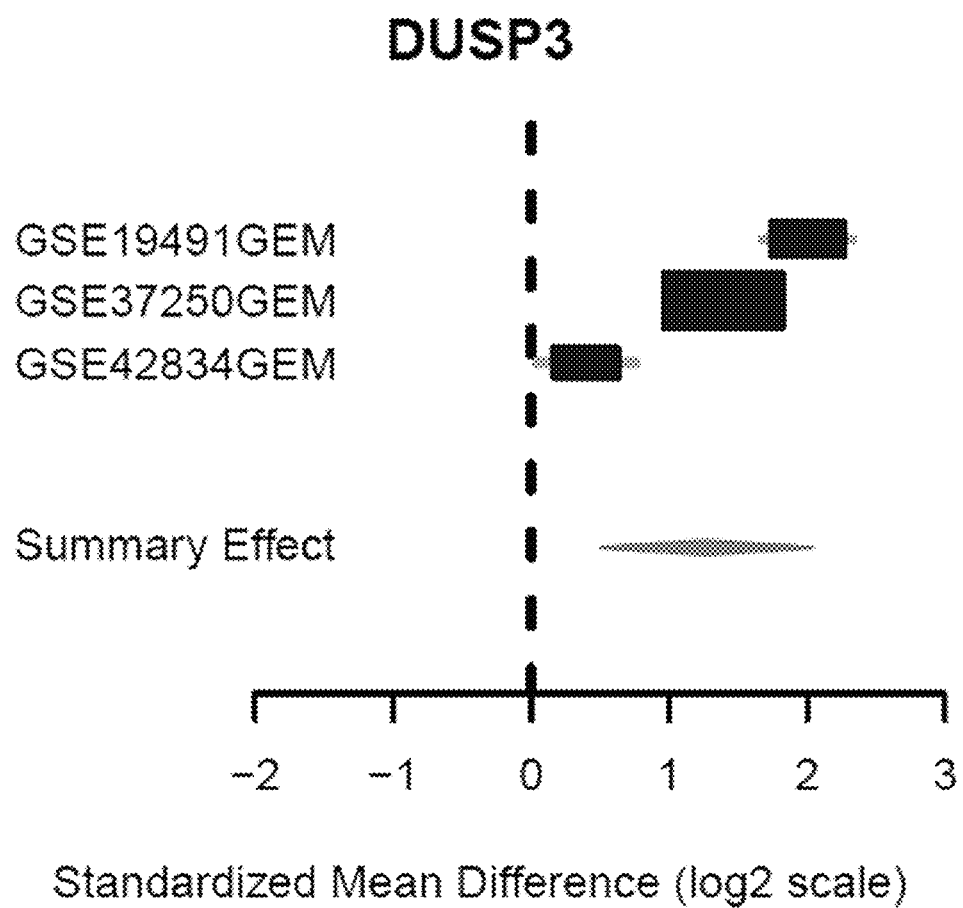
Figure 1D:
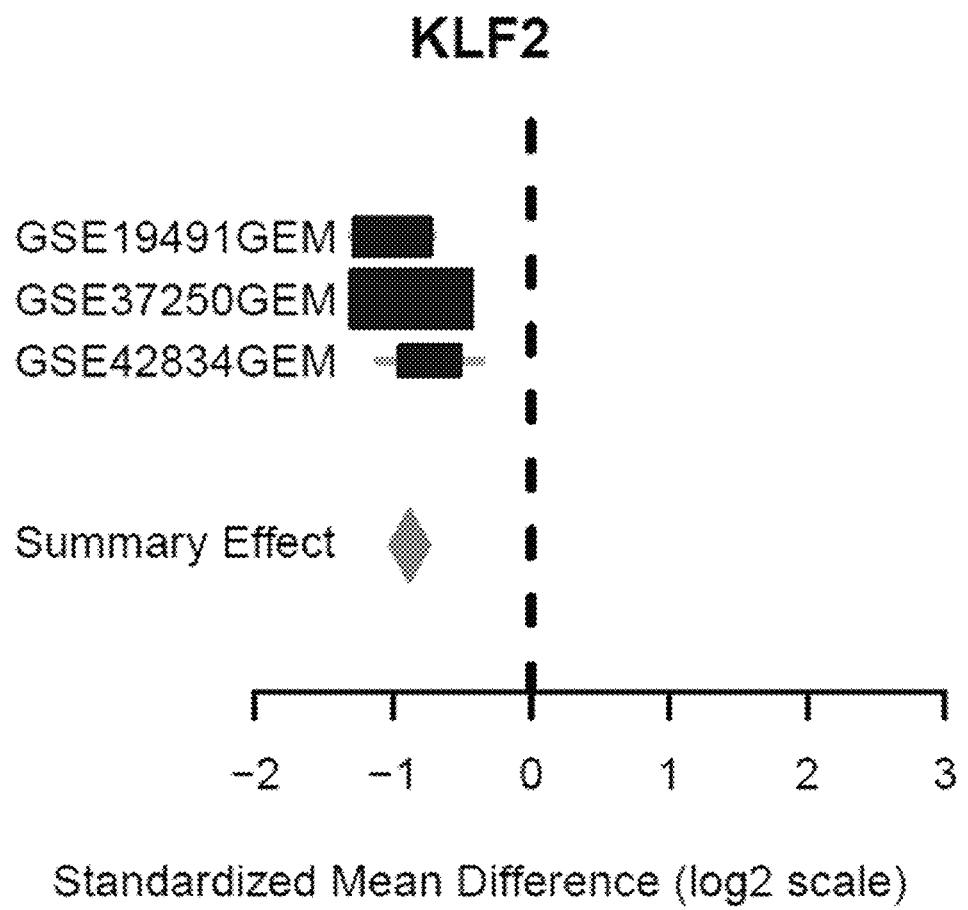
Figure 2A:
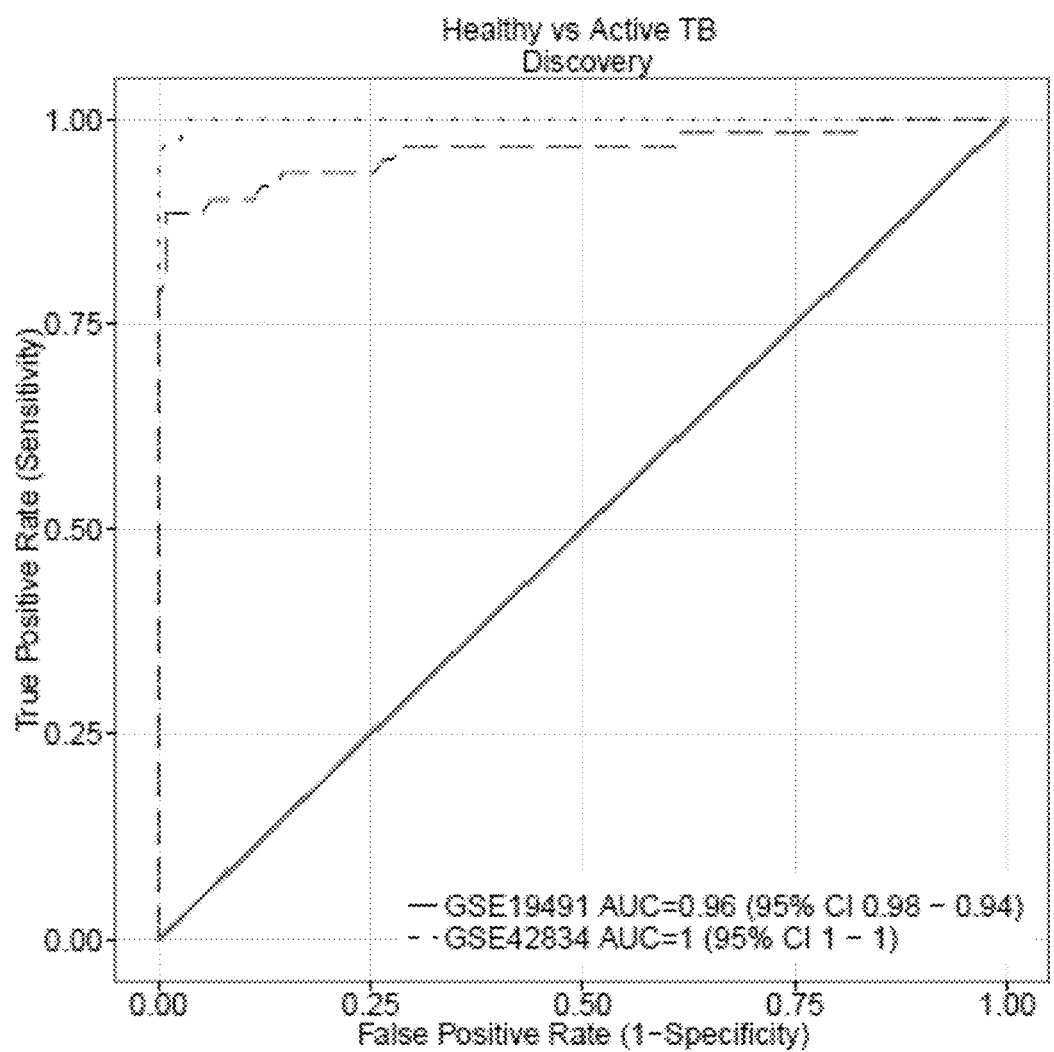
FIGS. 2A-2F show the performance of the three-gene set in the discovery datasets.
Figure 2B:
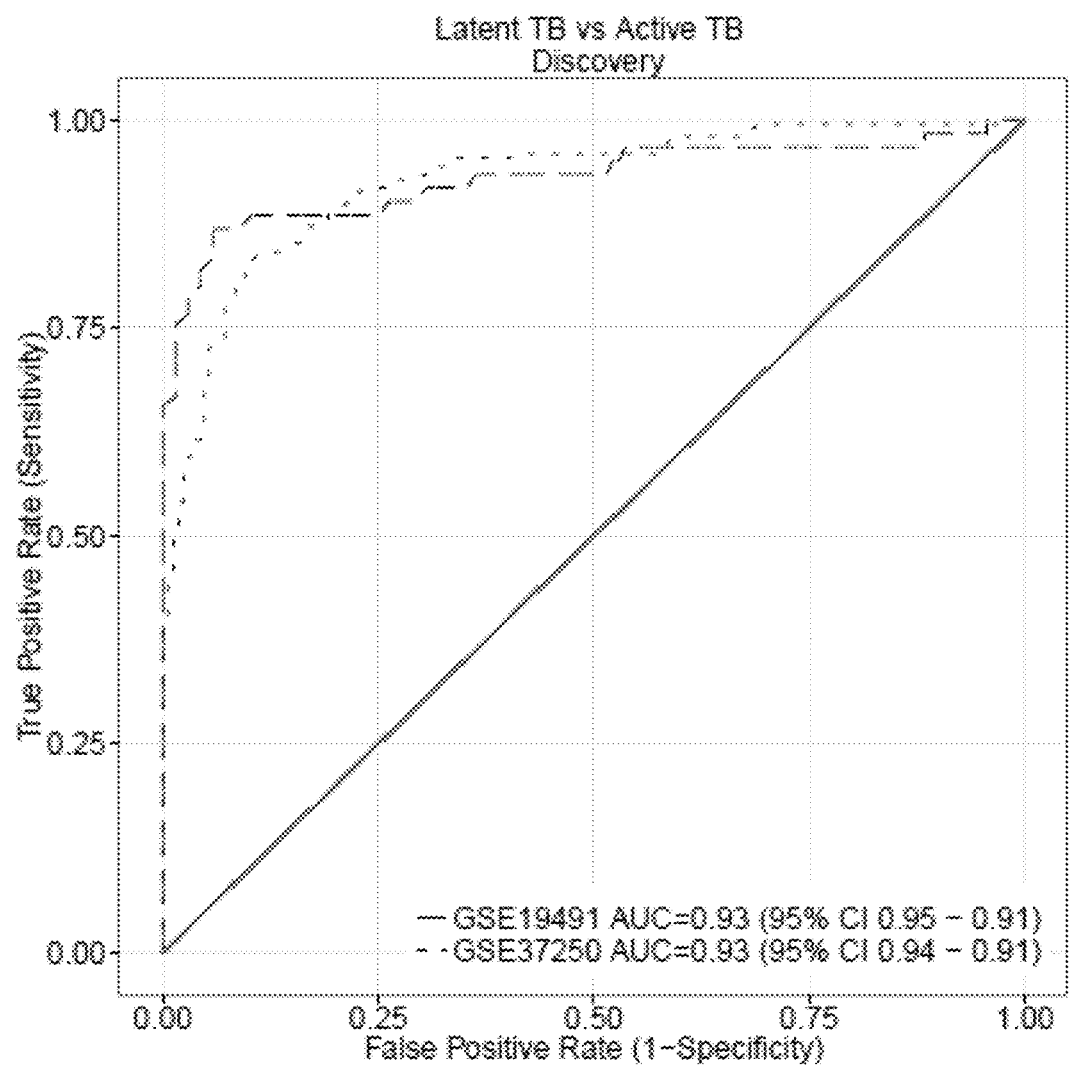
Figure 2C:
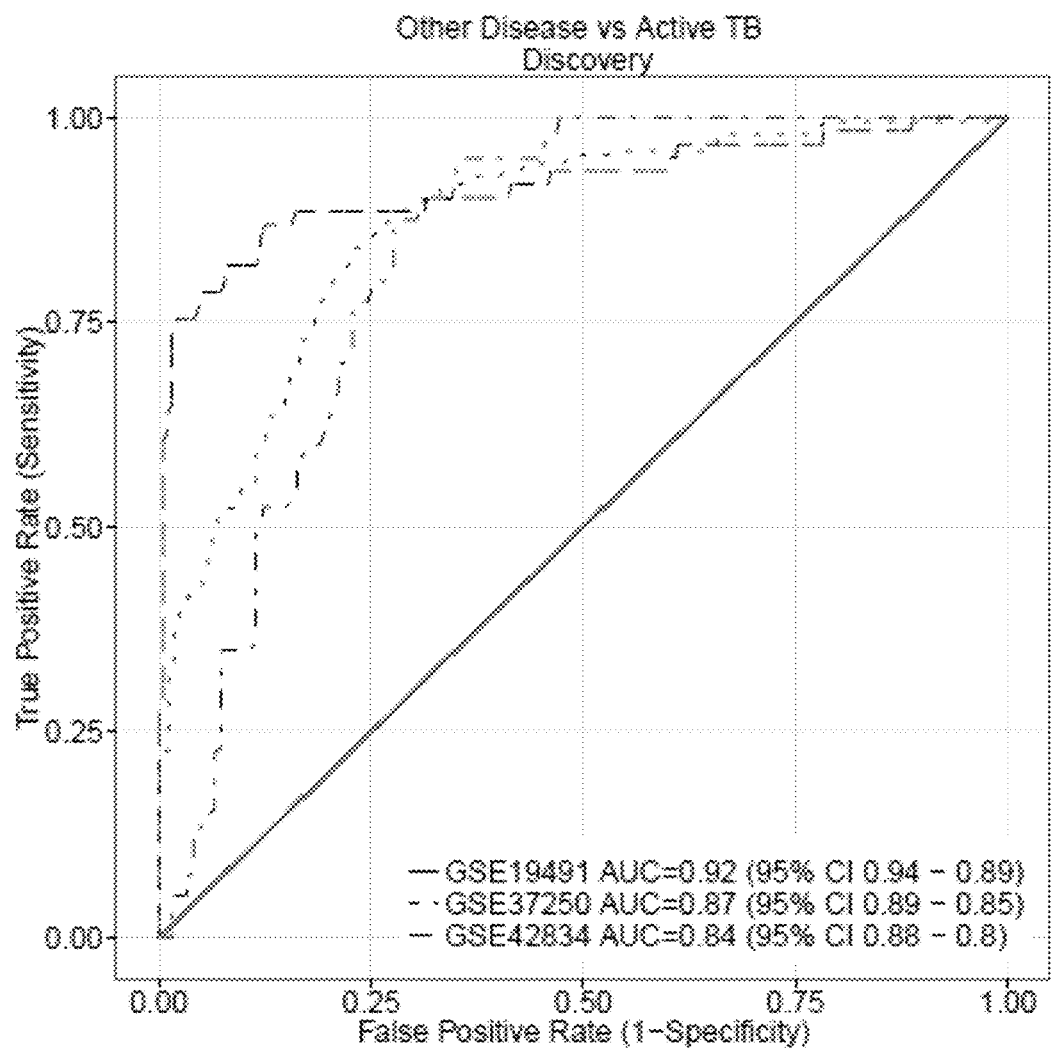
Figure 6A:
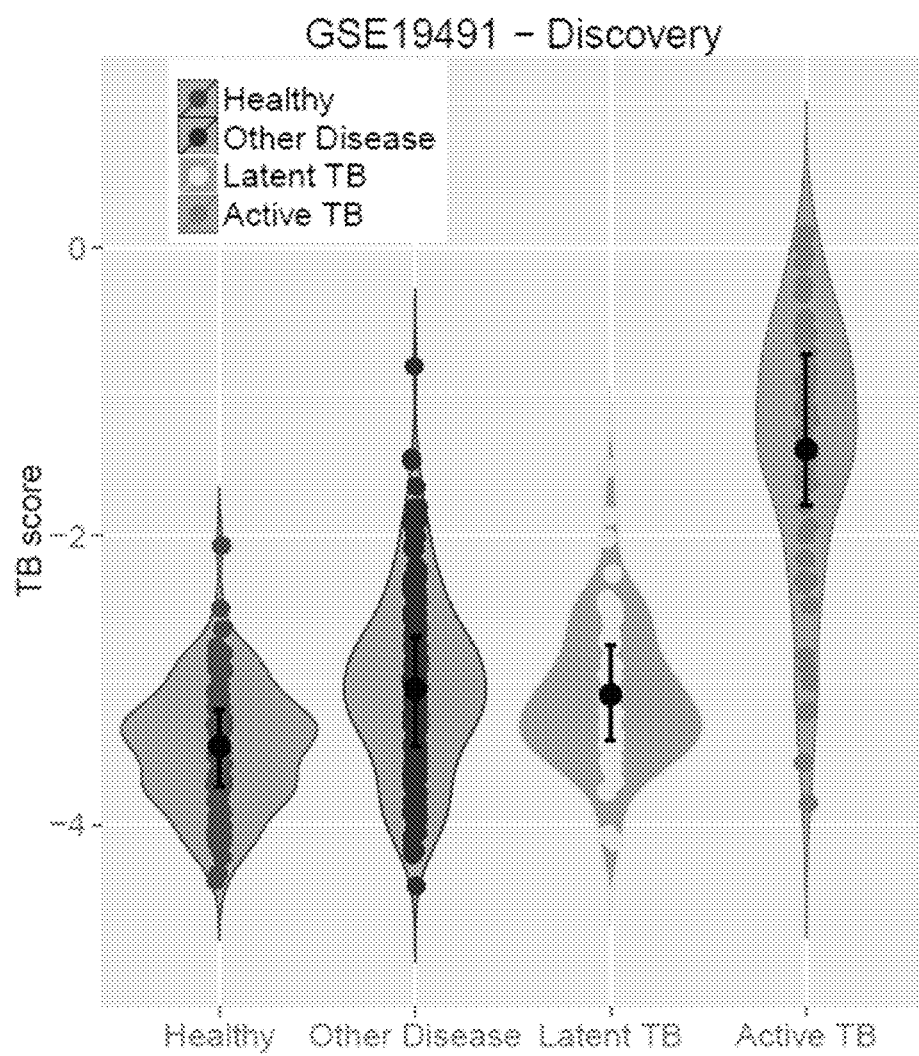
FIGS. 6A-6C show the performance of the three-gene set in the discovery datasets.
Figure 6B:
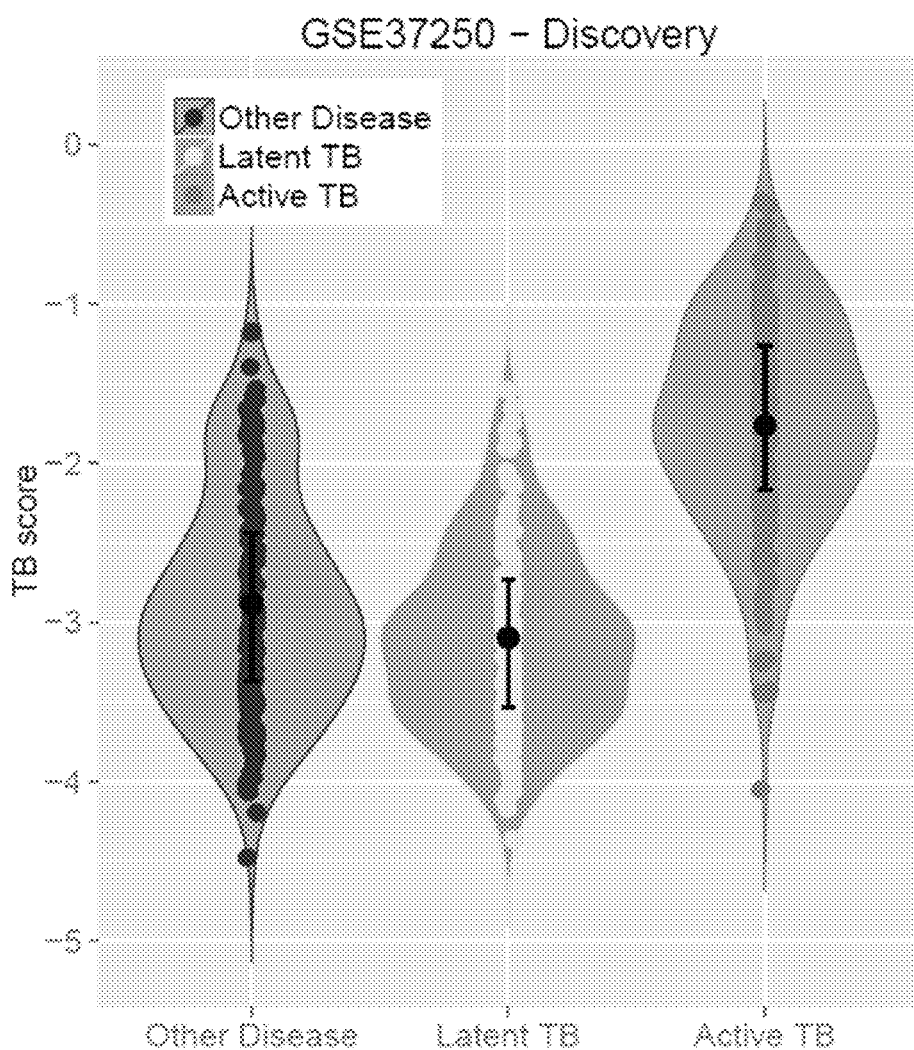
Figure 6C:
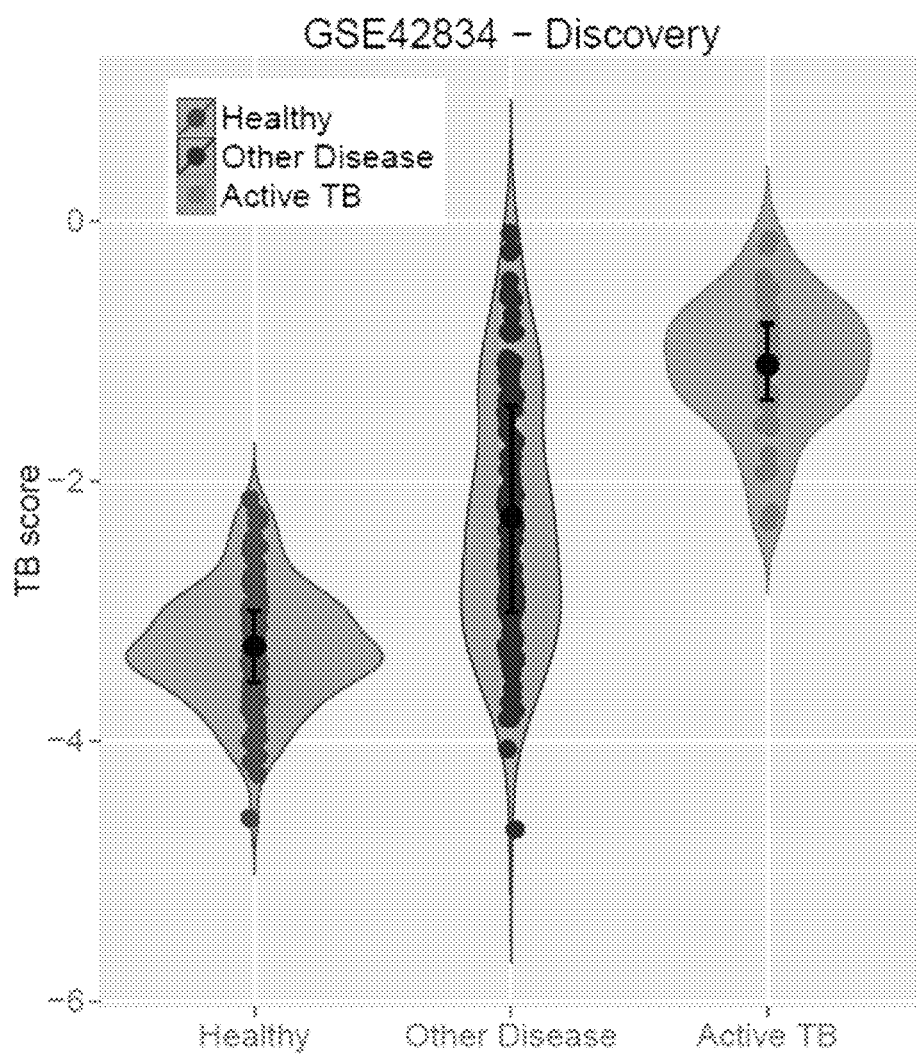
Figure 7A:
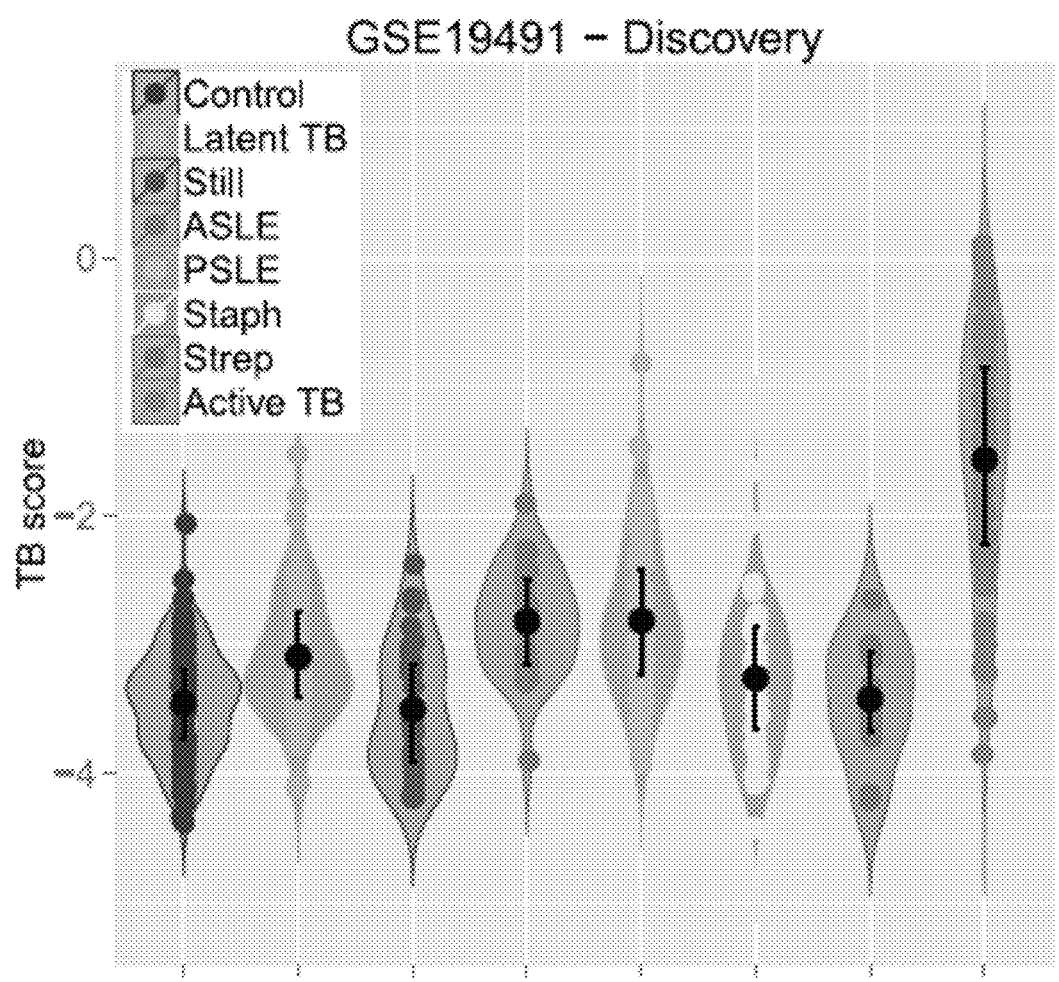
FIGS. 7A-7D show breakdown of 'Other Disease' category by disease type in the discovery datasets GSE19491 (FIGS. 7A and 7C) and GSE42834 (FIGS. 7B and 7D).
Figure 7B:
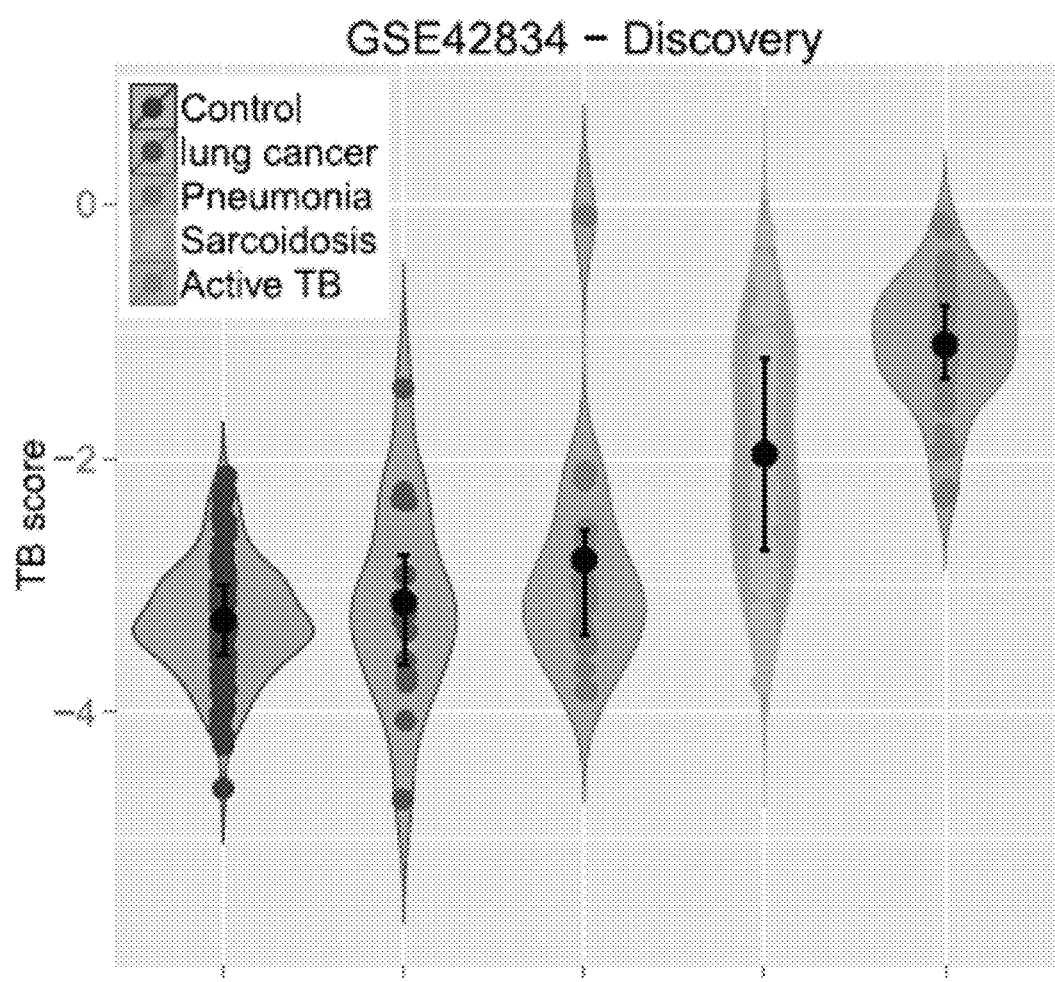
Figure 7C:
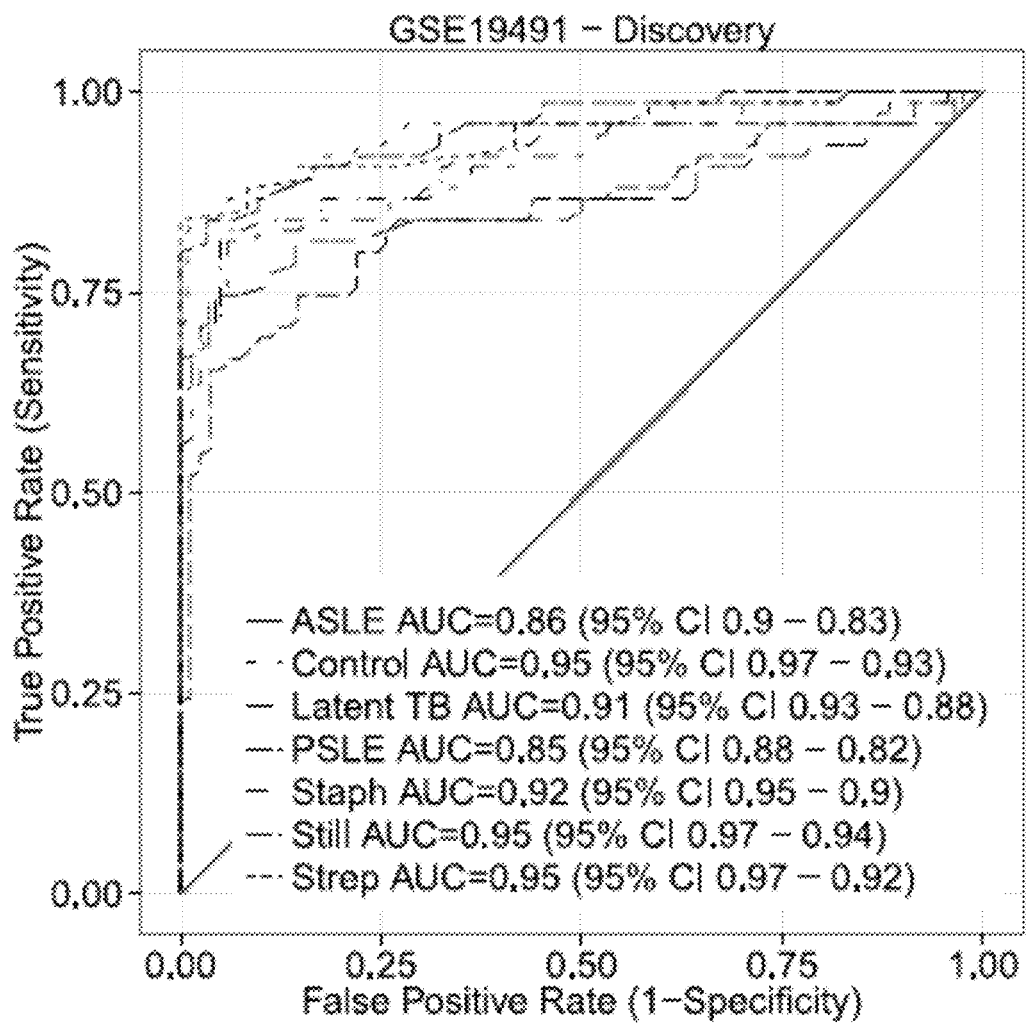
Figure 7D:
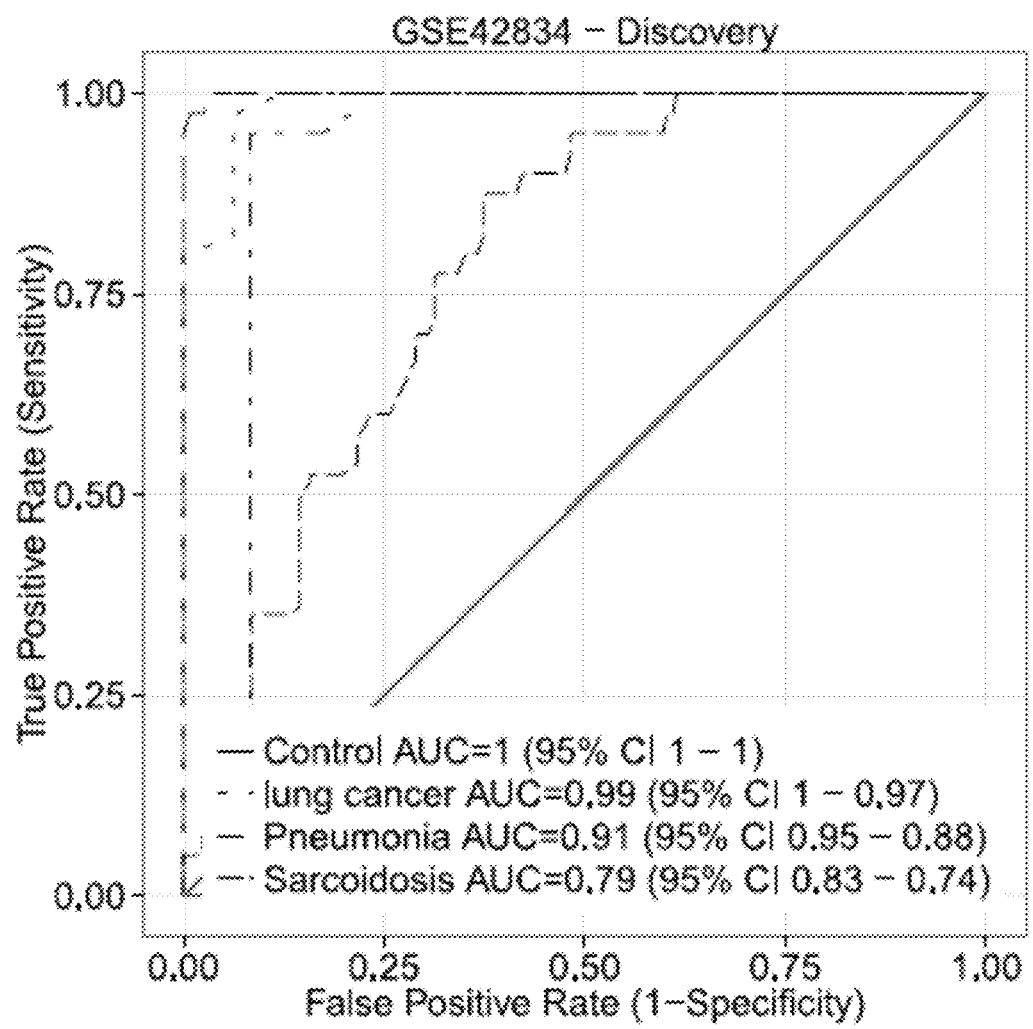
Figure 8A:
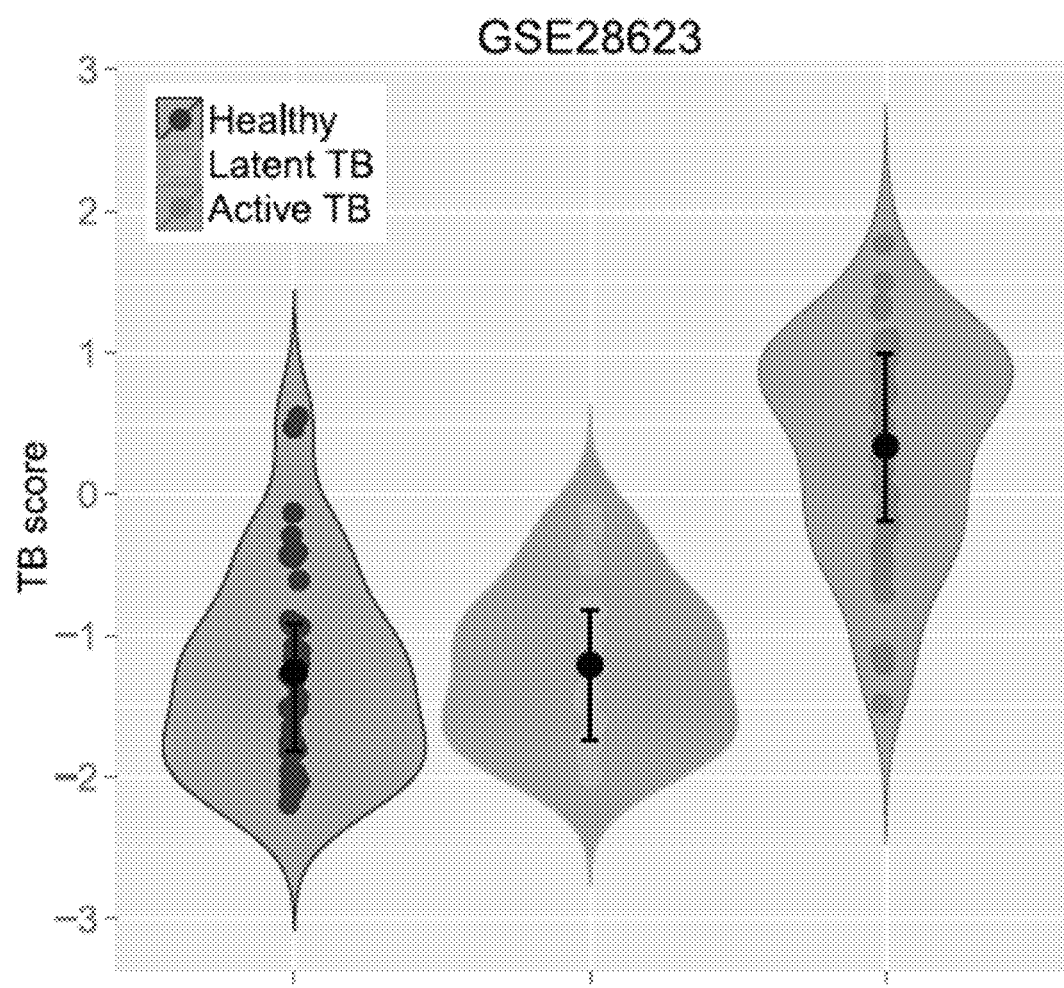
FIGS. 8A-8E show violin plots of the validation datasets GSE28623 (FIG. 8A), GSE34608 (FIG. 8B), GSE39940 (FIG. 8C), GSE39939 (FIG. 8D), and GSE41055 (FIG. 8E).
Figure 8B:
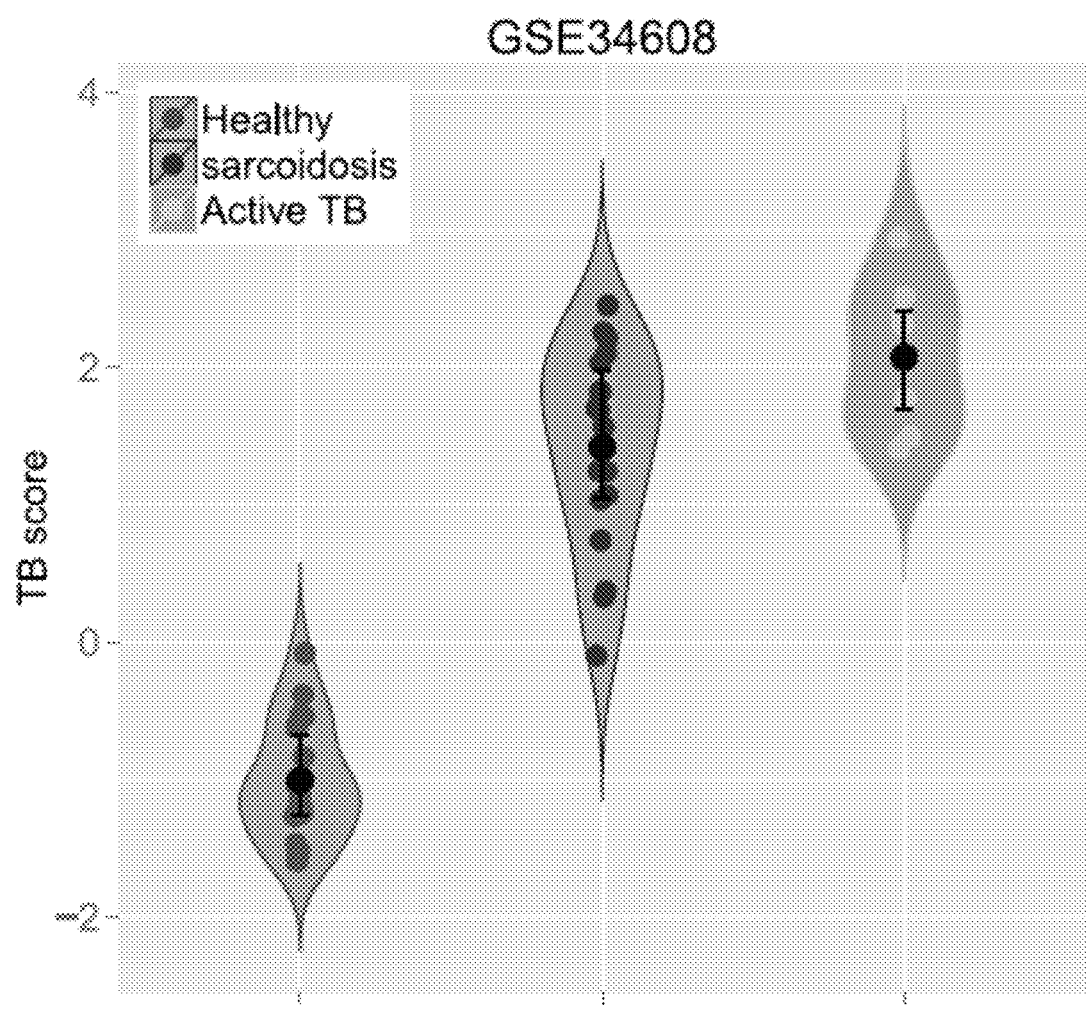
Figure 8C:
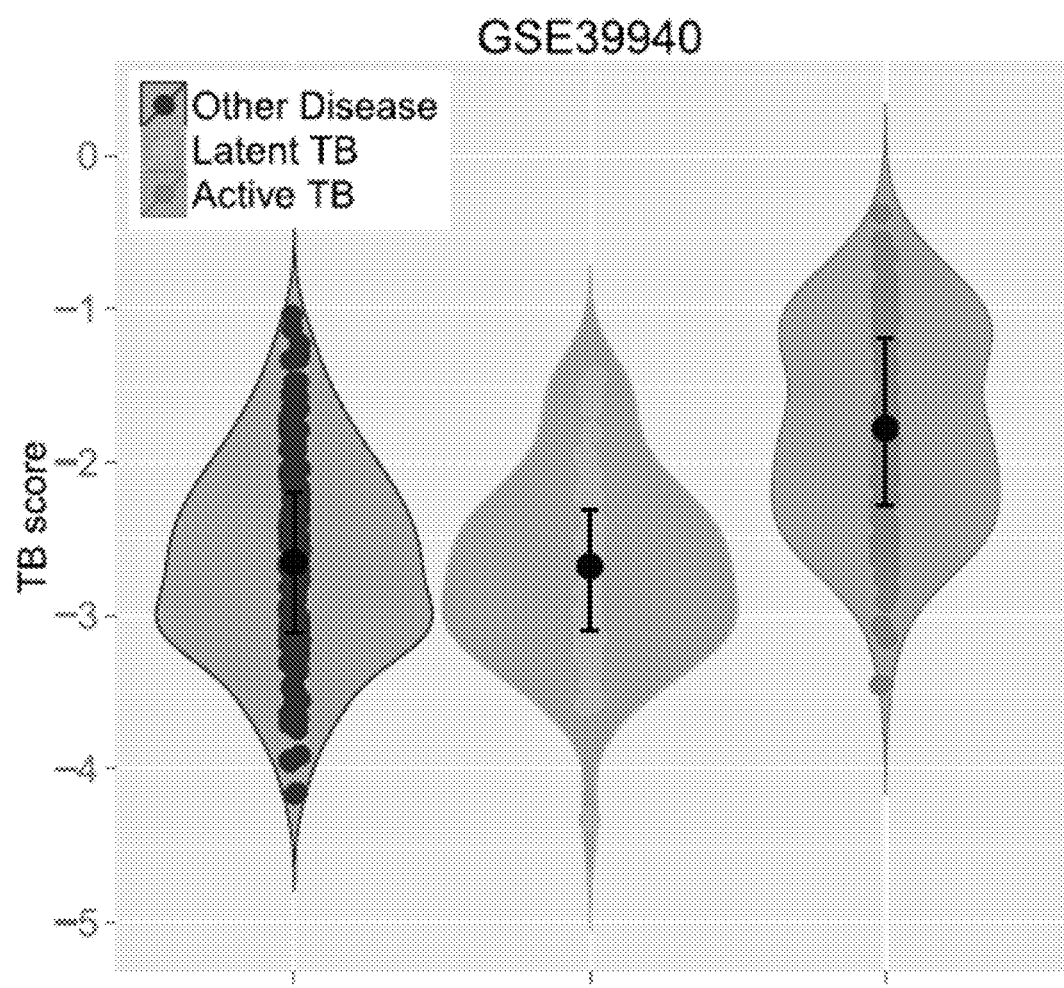
Figure 8D:
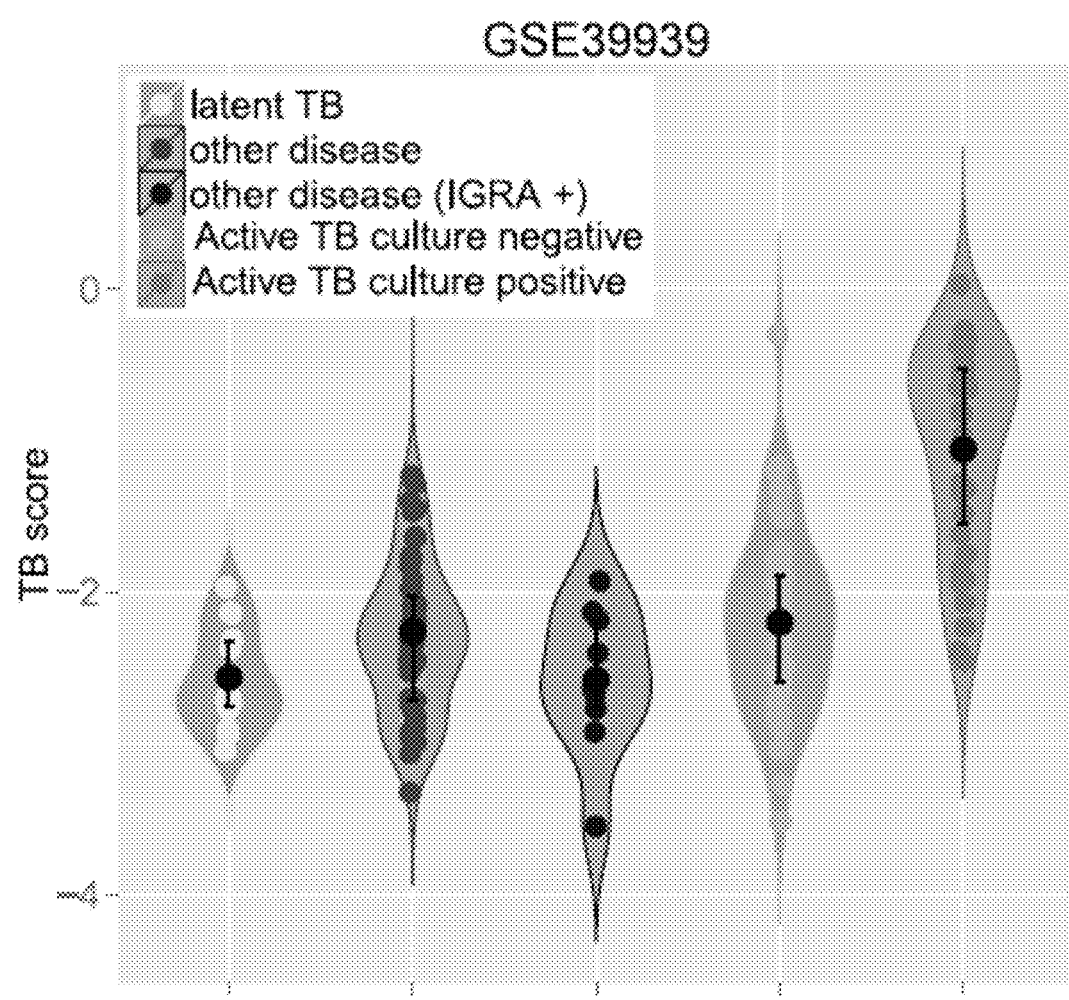
Figure 8E:
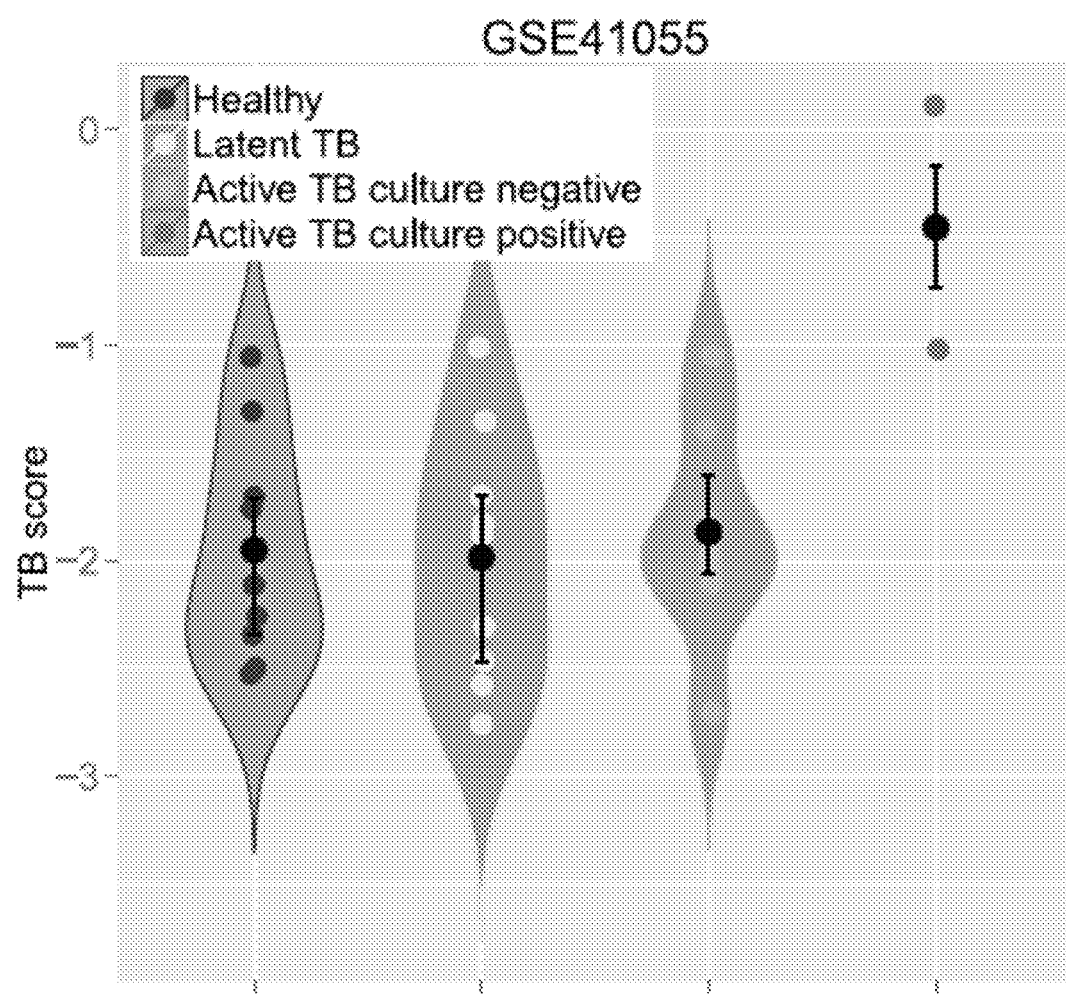

(2013) PLoS One 8:e70630), composed of 1,023 whole blood samples (LTB=236, OD=491, ATB=296), to compare patients with LTB or OD to patients with ATB (FIG. 1A). Samples with OD included patients with sarcoidosis, pulmonary and non-pulmonary infections, autoimmune disease, and lung cancer. We identified 266 genes significantly differentially expressed (158 over- and 108 under-expressed) in ATB compared to LTB and OD at FDR ≤1% and effect size >1.5 fold (Table 2). We applied a greedy forward search (Sweeney et al. (2015) Sci. Transl. Med. 7:287ra271) to obtain a set of genes optimized for diagnostic power, resulting in a three-gene set (GBP5, DUSP3, KLF2; FIG. 1B). As expected, in the discovery datasets, the three-gene set distinguished ATB from healthy controls (HC) (AUCs of 0.96 and 1.0, mean sensitivity 0.93, mean specificity 0.97), LTB (AUCs of 0.93 and 0.93, mean sensitivity 0.88, mean specificity 0.85), and OD (mean AUC of 0.88, range 0.84-0.92; mean sensitivity 0.82, mean specificity 0.79) (FIGS. 2A-2C; FIG. 6). Individual dataset test characteristics (sensitivity, specificity, NPV, PPV, and accuracy) are shown in Table 3. A breakdown of the 'other disease' category by disease class is shown in FIG. 7. The TB score performed well across all classes of other disease (AUC≥0.85) except sarcoidosis (AUC=0.79), which may be the result of the interferon response common to these two diseases (Maertzdorf et al. (2012) Proc. Natl. Acad. Sci. USA 109:7853-7858).

We next validated the three-gene set in 10 independent clinical TB gene expression datasets, including 4 types of comparisons: (1) HC vs. ATB, (2) LTB vs. ATB, (3) OD vs. ATB, and (4) longitudinal treatment/recovery from ATB. Several validation datasets include multiple patient classes (i.e., HC, LTB, and ATB); in such cases, we compared each patient class separately against the ATB group in the same dataset, where ATB was always defined as culture-positive or smear-positive cases.

Figure 2D:
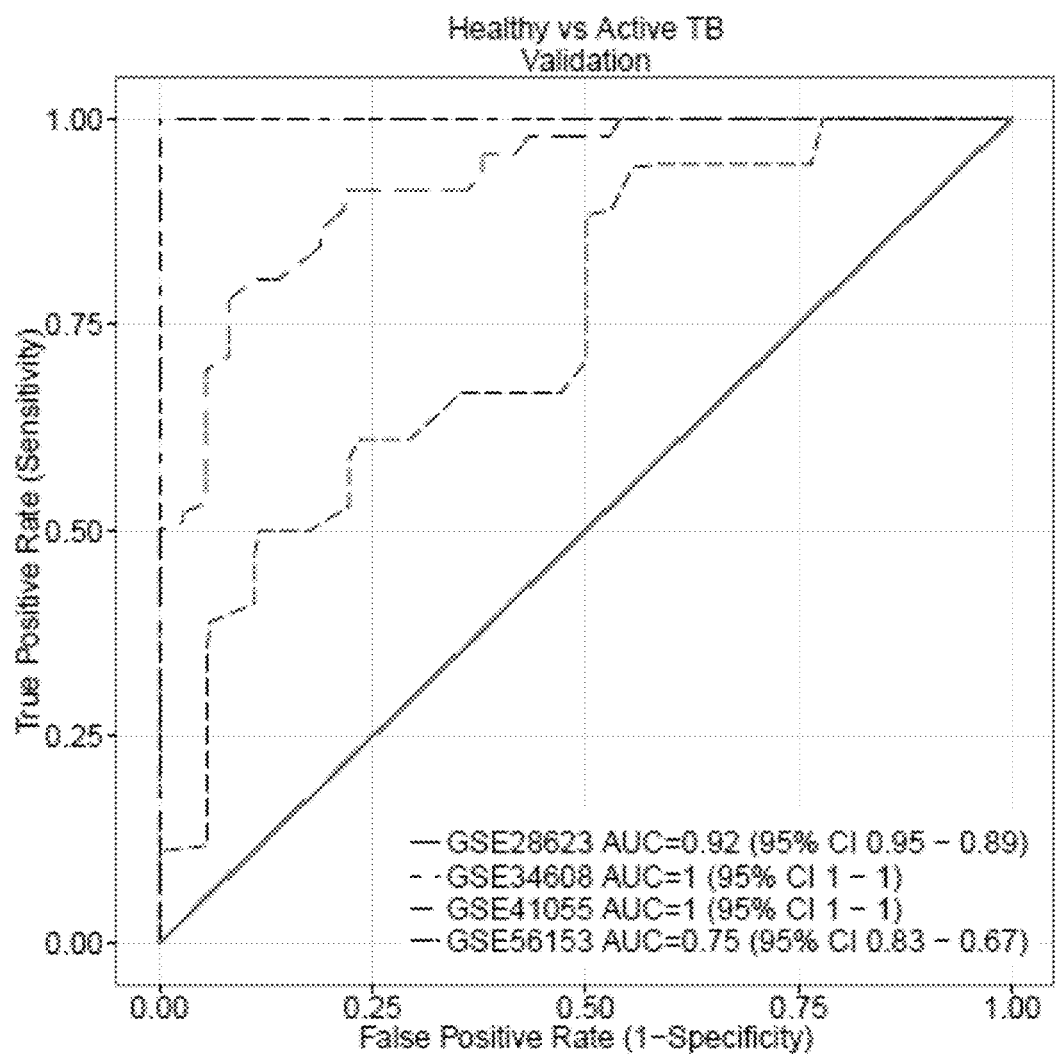
Figure 9:
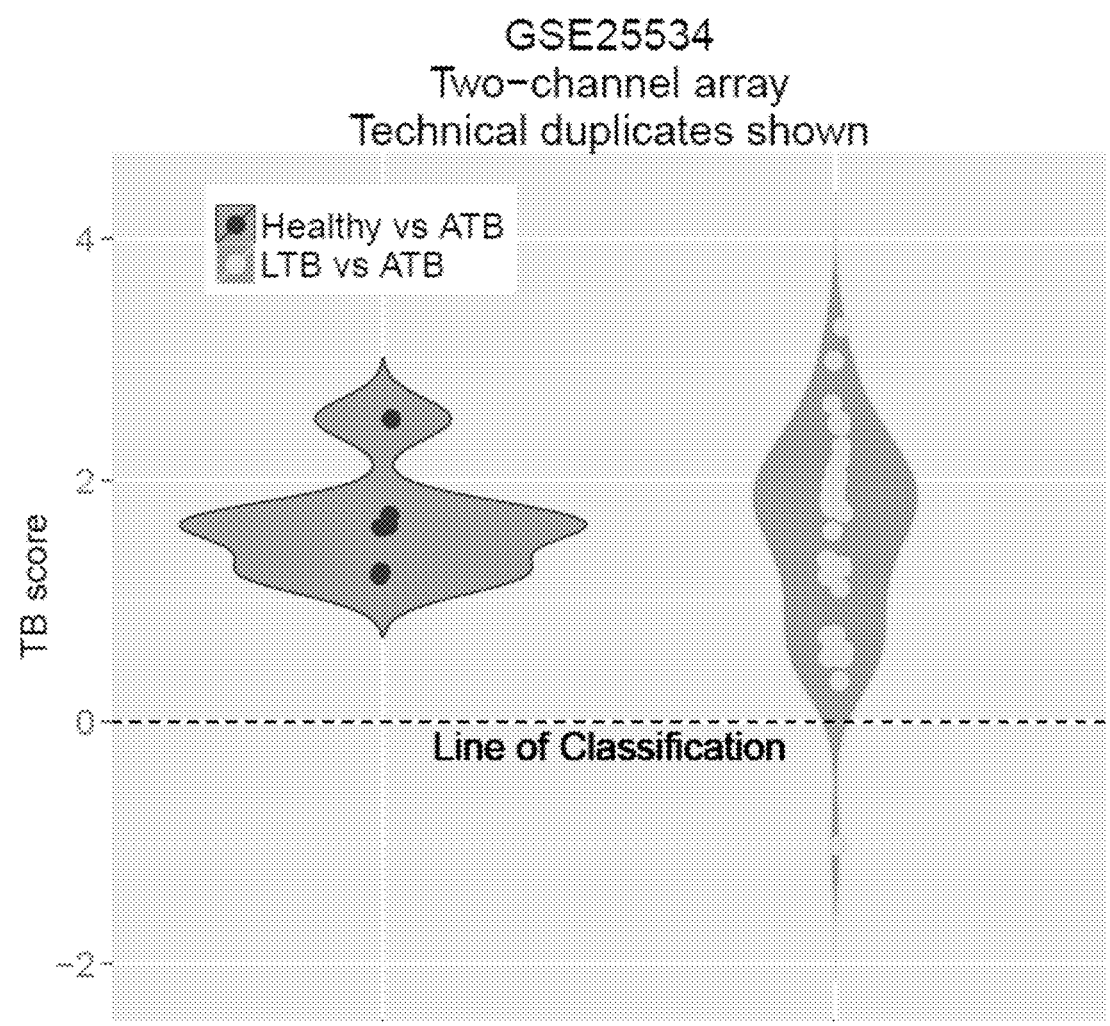
FIG. 9 shows the TB score in GSE25534, which utilized a two-channel array, wherein gene expression values represent relative values between the two samples on the array. Here, a positive TB score means that the TB score was greater in the ATB sample on the array than the control (healthy or LTB) sample on the array. A positive TB score for a given array would thus correctly classify that ATB sample vs. that control sample. The violin plots thus indicate that all but one sample are correctly classified by the three-gene set. As with other two-channel array studies, GSE25534 contains technical duplicates, which are shown here.

There were four independent datasets comparing HC with A TB patients (GSE28623 (adults, Maertzdorf et al. (2011) PLoS One 6, e26938), GSE34608 (adults, Maertzdorf et al. (2012) Proc. Natl. Acad. Sci. USA 109:7853-7858), GSE41055 (children, Verhagen et al. (2013) BMC Genomics 14:74), and GSE56153 (adults, Ottenhoff et al. (2012) PLoS One 7:e45839); total HC=82, ATB=91; Table 1). Despite significant clinical heterogeneity in these datasets, including age, country of origin, and inclusion criterion, ATB patients had significantly higher score compared to HCs (Wilcoxon P<0.05) in all datasets, with a mean AUC of 0.92 (range 0.75-1.0, mean sensitivity 0.86, mean specificity 0.81; FIG. 2D; FIG. 8; individual dataset test characteristics in Table 4). In a fifth dataset, GSE25534 (adults, Maertzdorf et al. (2011) Genes Immun. 12:15-22) that utilized a two-channel array design, the three-gene set perfectly classified healthy vs. ATB samples, though no ROC curve can be constructed (N=25, FIG. 9). Thus, our three-gene set successfully distinguished ATB patients from HCs.

Figure 2E:
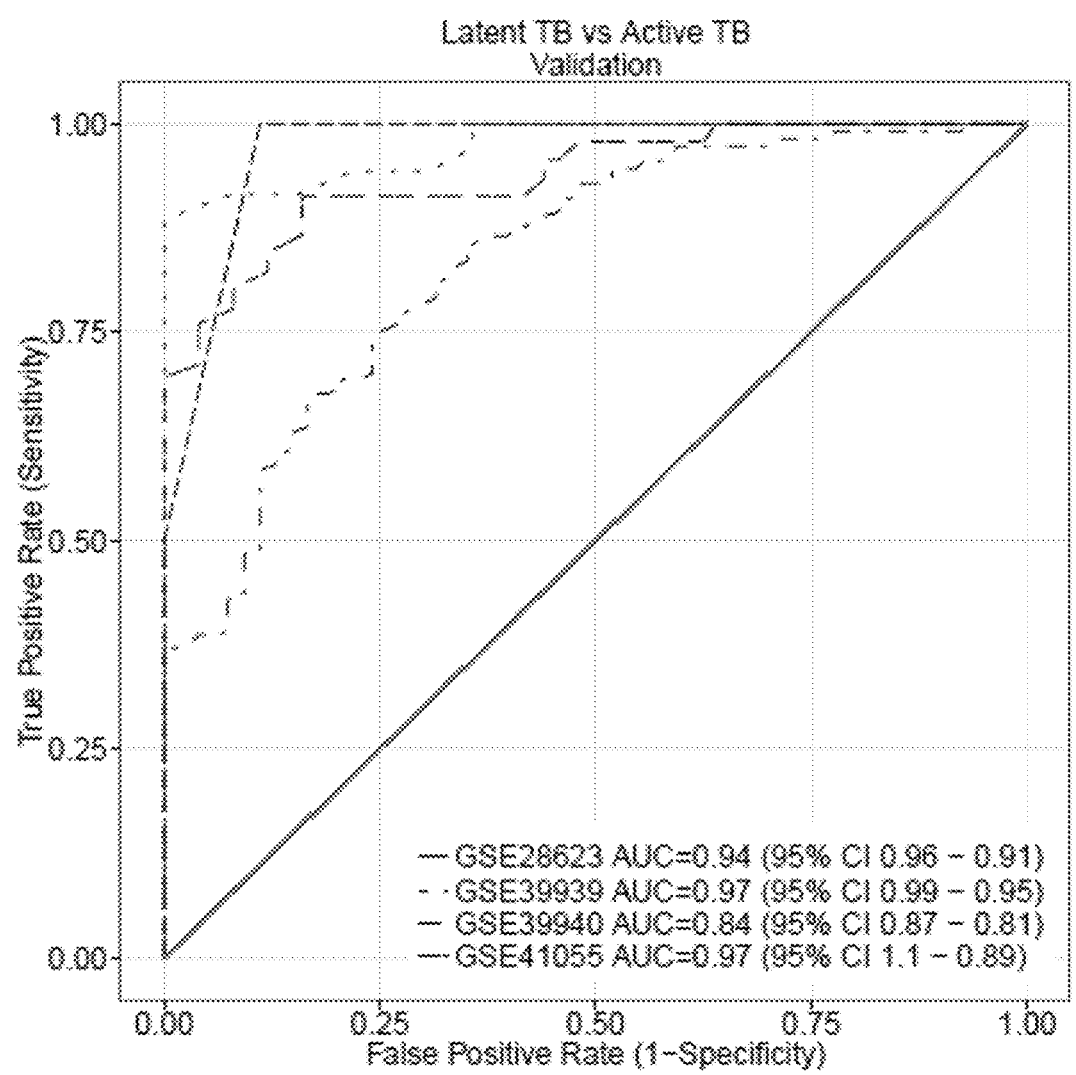

There were four independent datasets comparing LTB with A TB patients (GSE28623 (Maertzdorf et al. (2011) PLoS One 6:e26938), GSE39939 (children, Anderson et al. (2014) N. Engl. J. Med. 370:1712-1723), GSE39940 (children, Anderson et al., supra), and GSE41055 (Verhagen et al. (2013) BMC Genomics 14:74); total LTB=102, ATB=194; Table 1). ATB patients had higher TB scores compared to LTB patients (Wilcoxon P<0.05) in all datasets. The four cohorts had a mean AUC of 0.93 (range 0.84-0.97; mean sensitivity 0.87, mean specificity 0.85; FIGS. 2E and 8; individual dataset test characteristics in Table 4). Furthermore, in GSE25534 (with a two-channel array), the three-gene set classified LTB vs. ATB samples with 97% accuracy (N=38, FIG. 9). These results provide strong evidence that the three-gene set separates ATB from LTB.

Figure 2F:
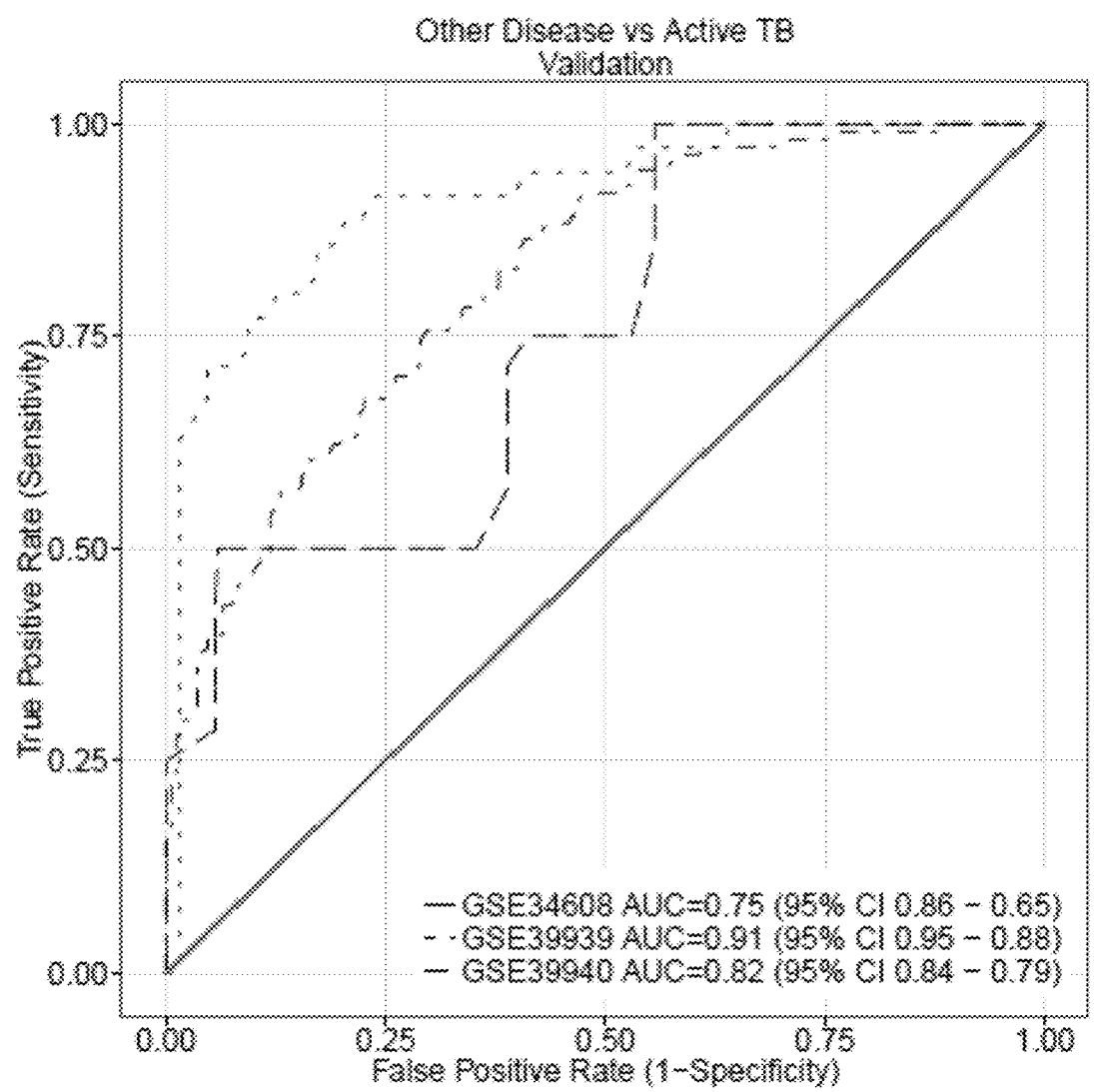

There were three independent datasets comparing OD with A TB patients (GSE34608 (Maertzdorf et al. (2012) Proc. Natl. Acad. Sci. USA 109:7853-7858), GSE39939 (Anderson et al. (2014) N. Engl. J. Med. 370:1712-1723), GSE39940 (Anderson et al., supra); total OD=251, ATB=154; Table 1). In these cohorts, the 'other disease' category included primarily pneumonia patients, but also patients with chronic lung diseases such as sarcoidosis, non-pulmonary infections, or malignancies. ATB patients had higher TB scores compared to OD patients (Wilcoxon P<0.05) in all datasets. The three cohorts had a mean AUC of 0.83 (range 0.75-0.91; mean sensitivity 0.65, mean specificity 0.74; FIG. 2F; FIG. 8; individual dataset test characteristics in Table 4). Even in the difficult case of separating ATB from OD, the three-gene set performs well.

Figure 3:
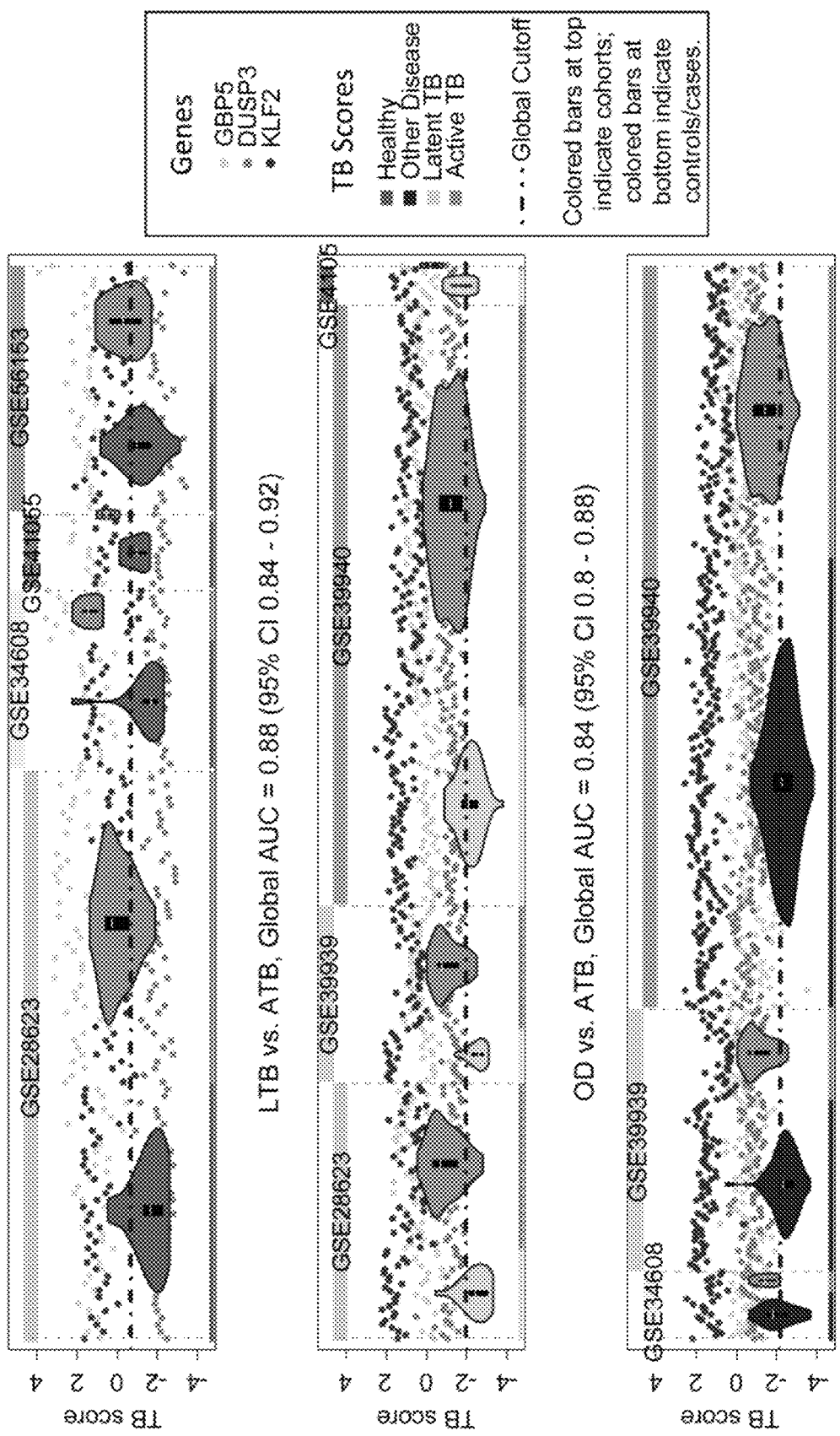
FIG. 3 shows the establishment of a single global test cutoff in the validation datasets. Shown are sample-level normalized gene scores, along with group TB score distributions. Bars within violin plots indicate inner quartiles; white dash is median. By centering the genes within each dataset to their global mean, a single cutoff across multiple datasets can be established.
Figure 10:
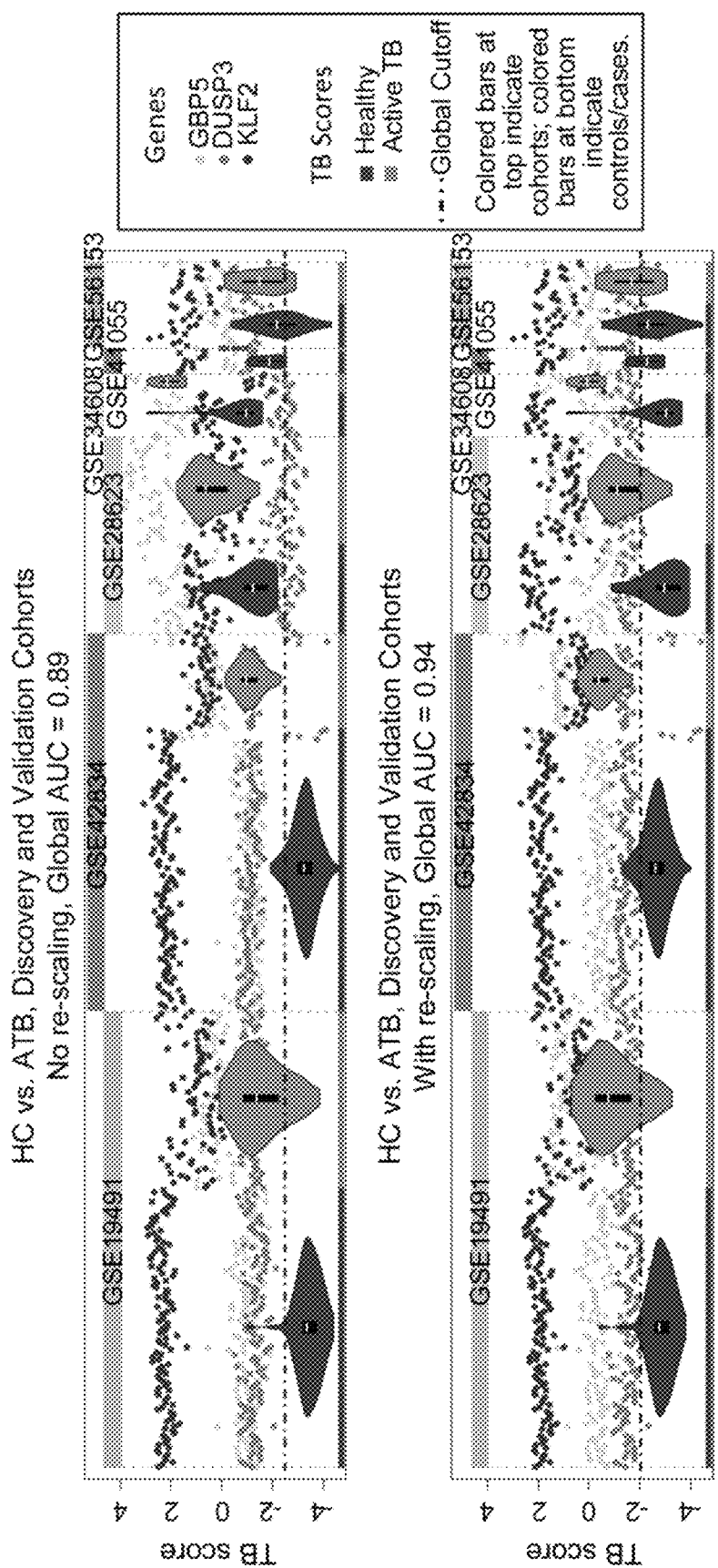
FIG. 10 shows the establishment of a single global test cutoff in the joint discovery and validation datasets for HC versus ATB. Shown are sample-level normalized gene scores, along with group TB score distributions.
Figure 11:
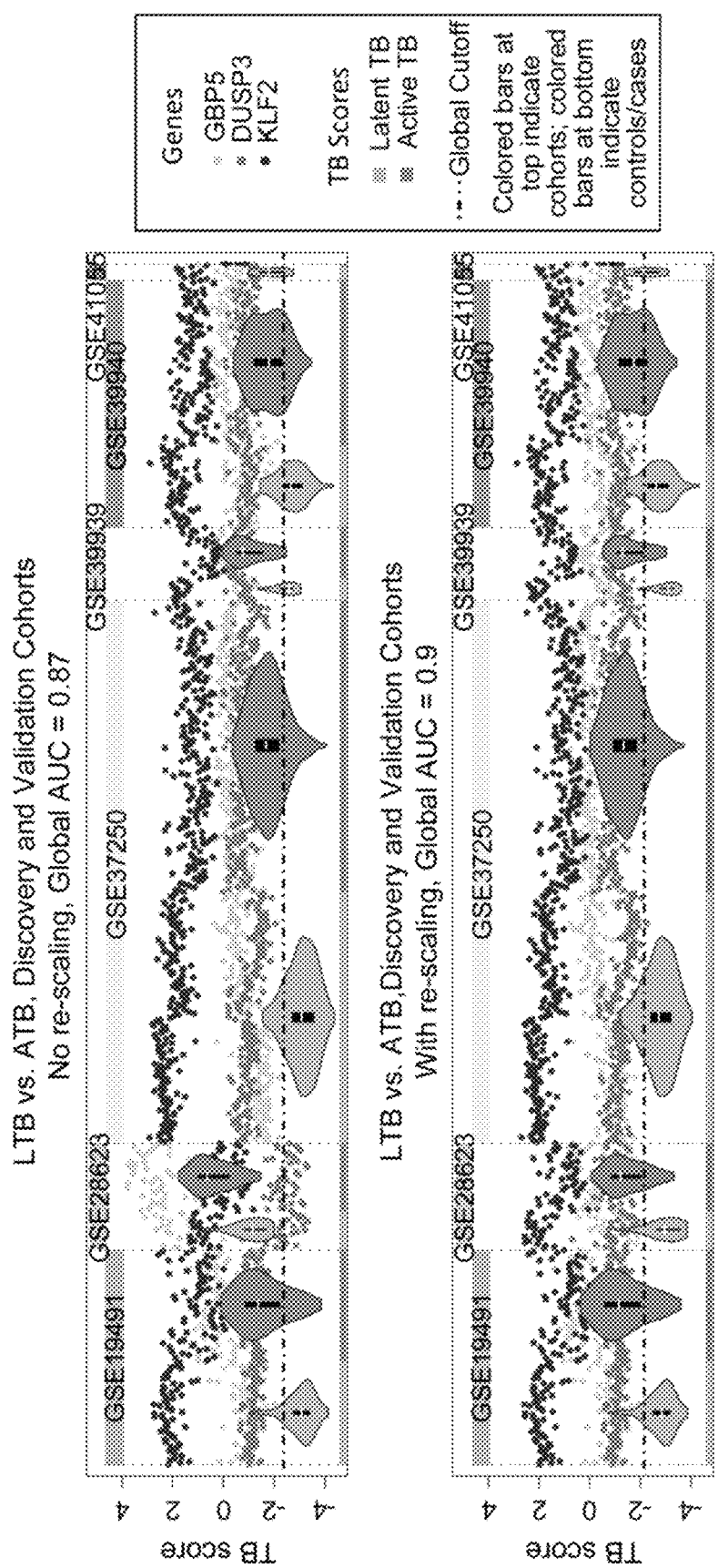
FIG. 11 shows the establishment of a single global test cutoff in the joint discovery and validation datasets for LTB versus ATB. Shown are sample-level normalized gene scores, along with group TB score distributions.
Figure 12:
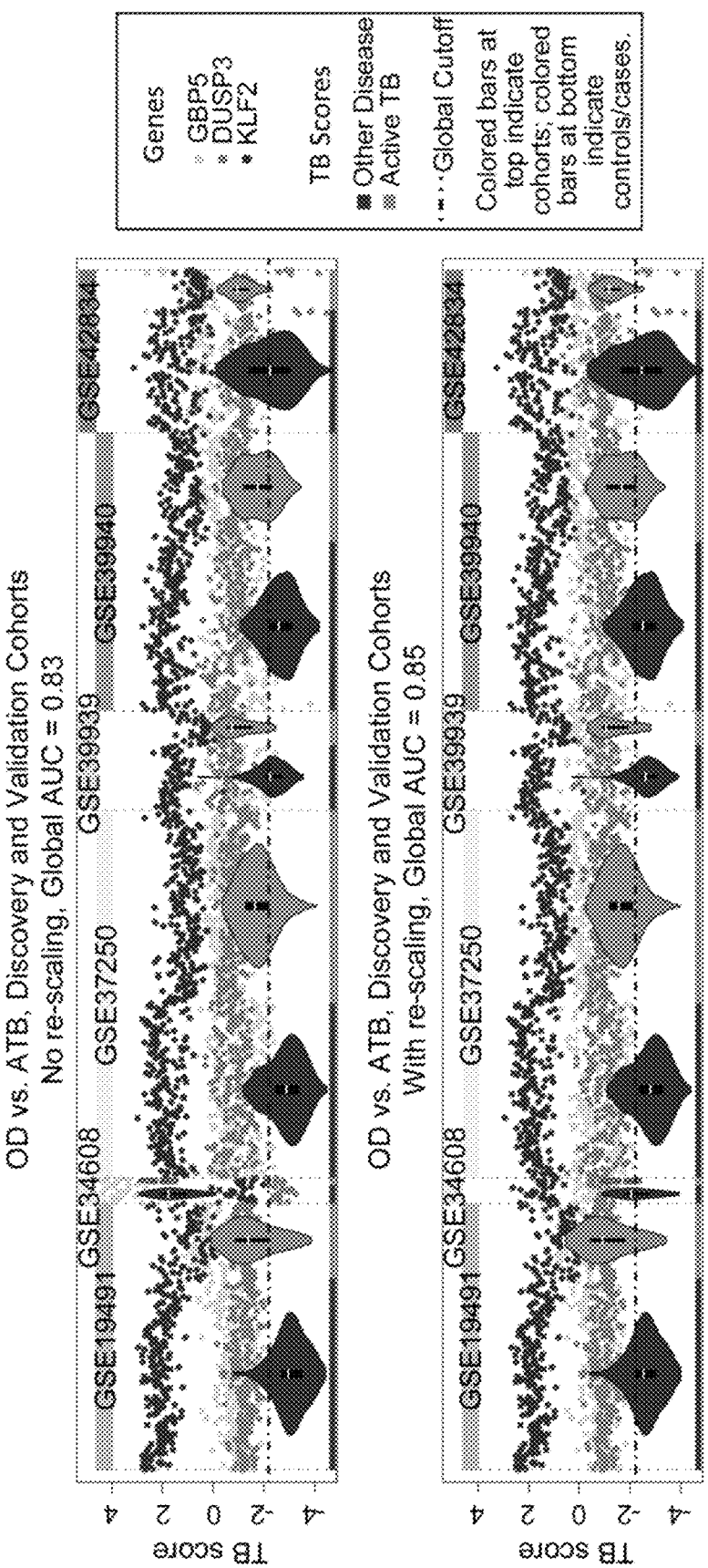
FIG. 12 shows the establishment of a single global test cutoff in the joint discovery and validation datasets for OD vs ATB. Shown are sample-level normalized gene scores, along with group TB score distributions.

The test characteristics reported for each of the comparisons above used different TB score thresholds for each dataset to maximize joint specificity and sensitivity within a given dataset. However, a 'real-world' clinical application would require a single threshold that can be applied universally across all patients (instead of using different thresholds for different cohorts). A real-world application would also use a single technology for all patients across all cohorts. In contrast, in our study, cohorts were profiled on a variety of microarray technologies with different processing methods. Hence, the background levels of gene expression between the cohorts varied significantly. Therefore, to evaluate the performance of the TB score in a more 'real-world' manner, we constructed global expression matrices, where all datasets for each type of comparison were merged into a single matrix, and then tested the TB score for a single global cutoff across all datasets. Because the various microarray technologies measure the baseline expression values of each gene differently, we corrected the mean expression level for each gene in a dataset to match the global mean such that the within-dataset distribution for a given gene is preserved. We were thus able to evaluate a single global ROC AUC for each comparison, and estimate test characteristics from optimal cutoffs. The AUCs using a global cutoff across all datasets were: HC vs. ATB, AUC 0.90 (sensitivity 0.85, specificity 0.93), LTB vs. ATB, AUC 0.88 (sensitivity 0.80, specificity 0.86), and OD vs. ATB, AUC 0.84 (sensitivity 0.81, specificity 0.74) across all validation datasets (FIG. 3). The effects of the mean scaling, and the effects of including the discovery datasets into the global expression matrices, are shown in FIGS. 10-12. These results show that even when we enforce a global threshold, our gene signature is able to maintain accurate partitioning of ATB patient from the HC, LTB, and OD cohorts.

Figure 4A:
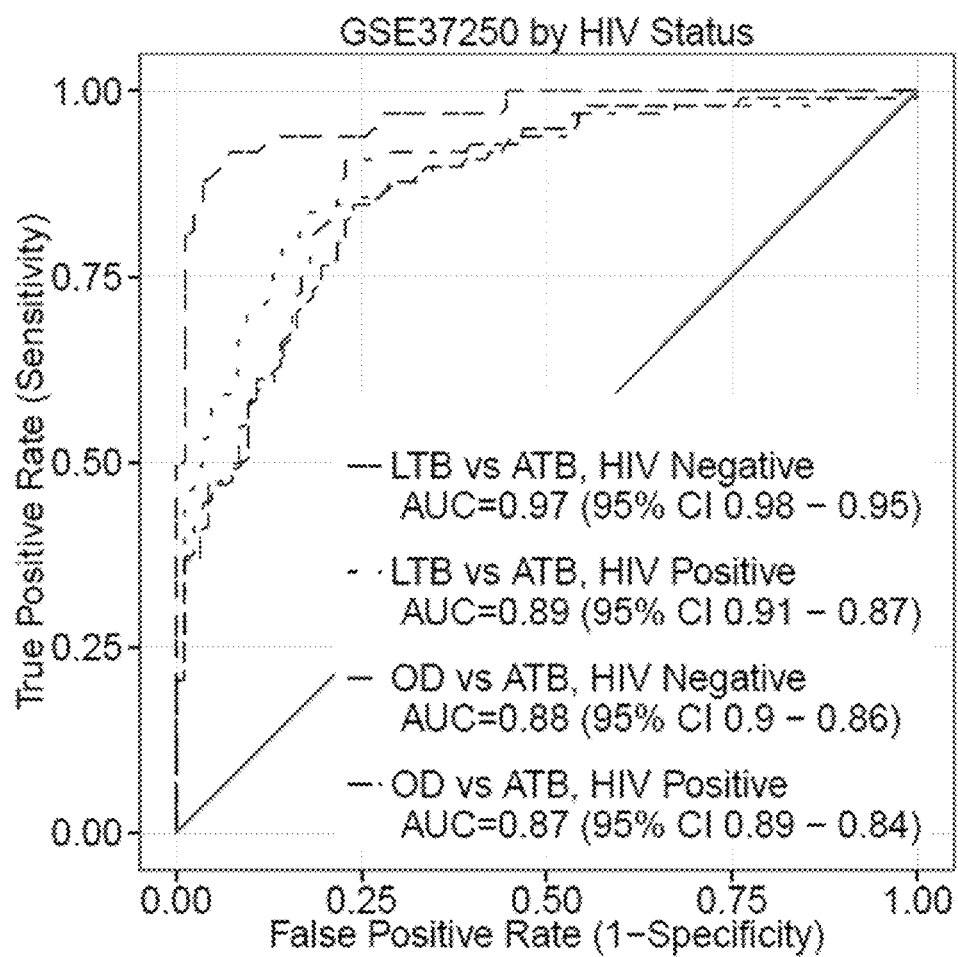
FIGS. 4A-4C show that in GSE37250 (FIG. 4A), GSE39939 (FIG. 4B), and GSE39940 (FIG. 4C), there was no significant difference in diagnostic power for OD versus ATB based on HIV status. In GSE37250, there was a decrease in ROC AUC from 0.96 to 0.89 in LTB vs ATB in HIV positive patients.
Figure 4B:
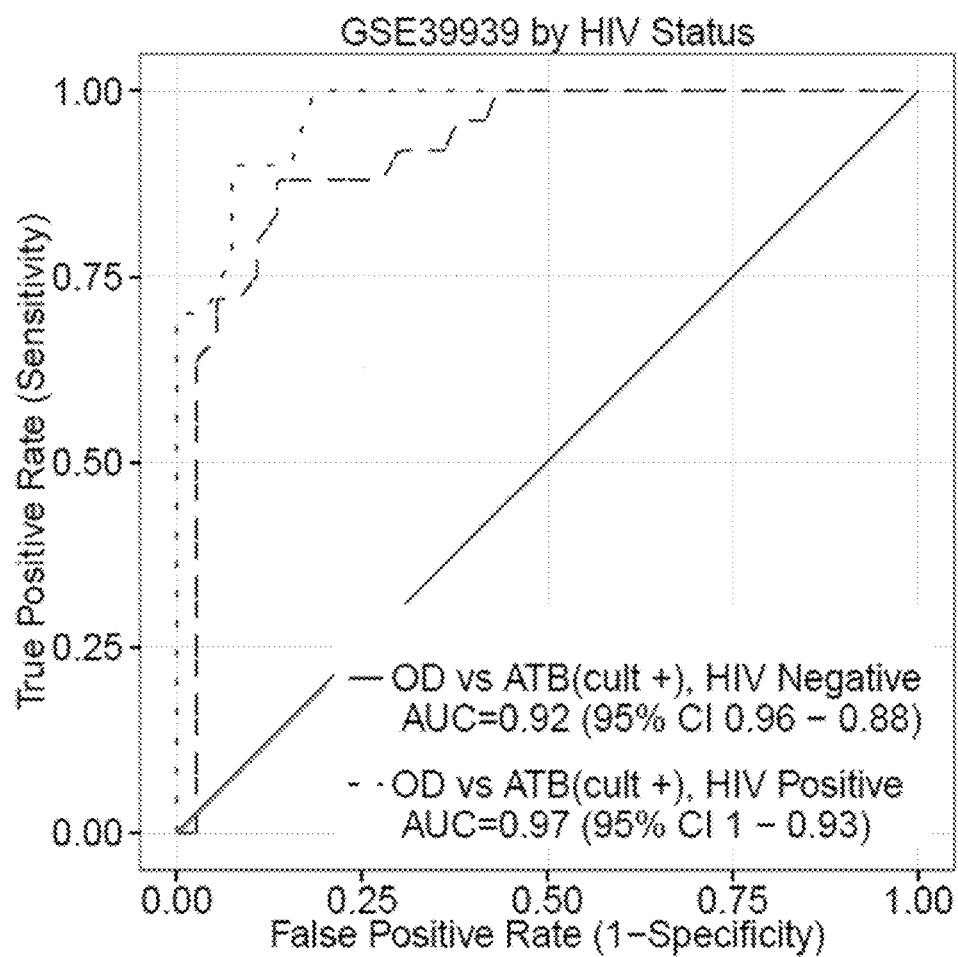
Figure 4C:
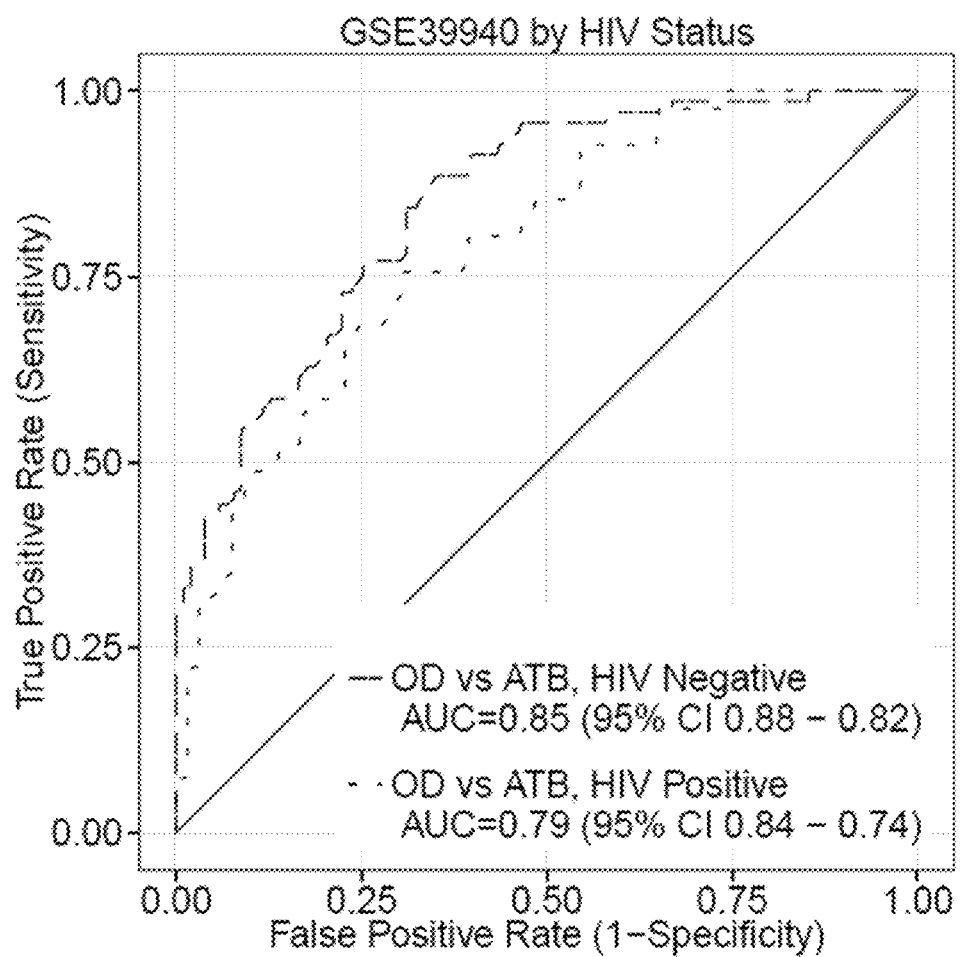
Figure 5A:
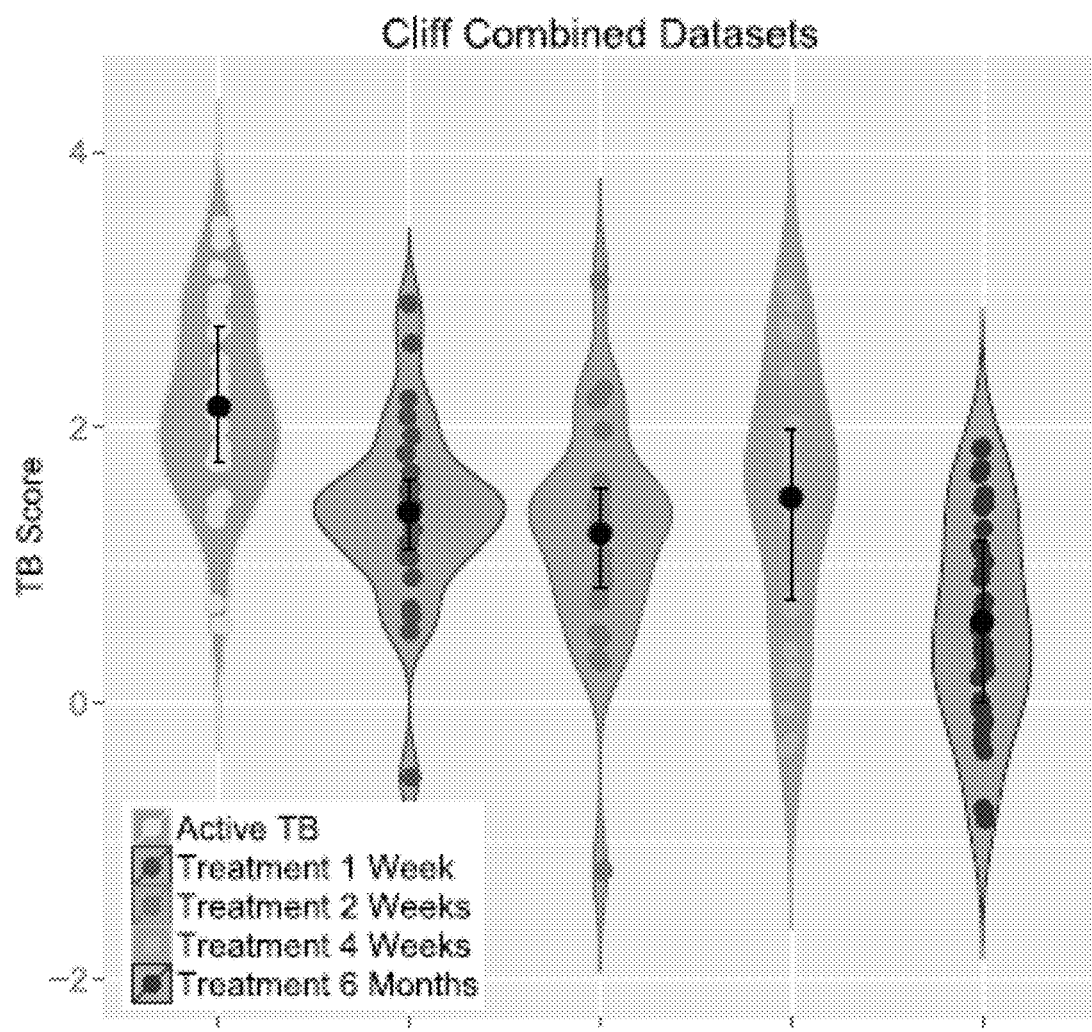
FIGS. 5A-5D show the performance of the three-gene set in longitudinal validation datasets. The four validation datasets, including Cliff combined (FIG. 5A), GSE40553 (FIG. 5B), GSE56153 (FIG. 5C), and GSE62147 (FIG. 5D) examined active TB patients during treatment and recovery. All four show recovery of the three-gene set with treatment.
Figure 5B:
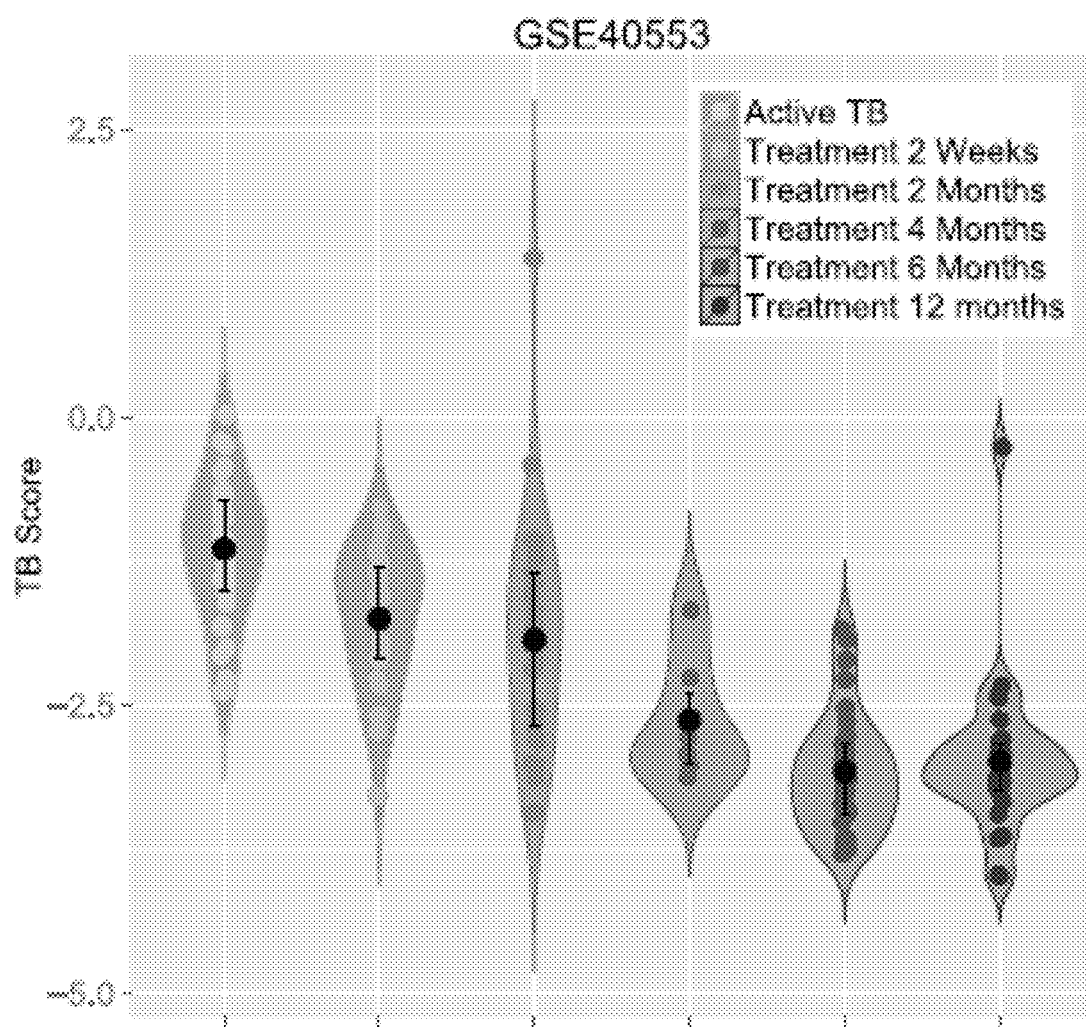
Figure 5C:
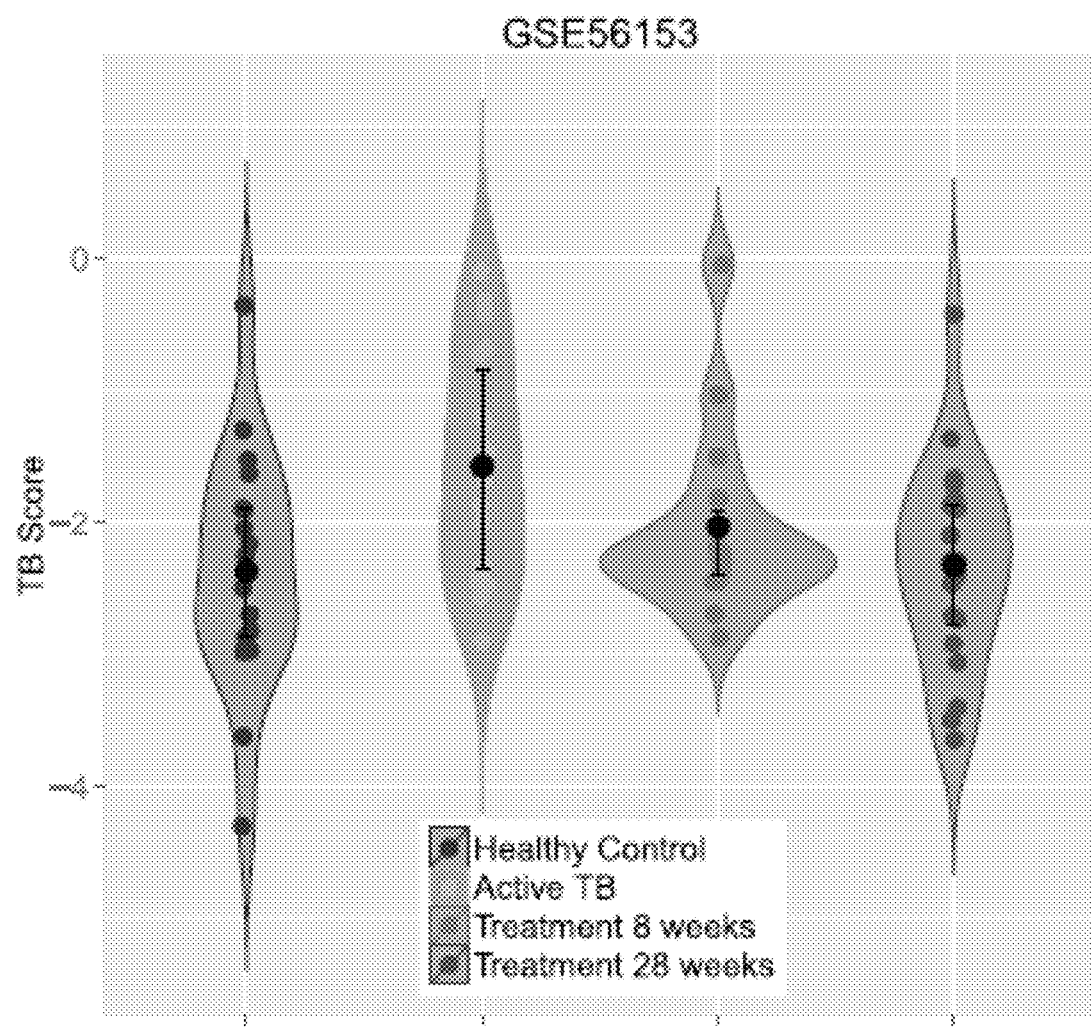
Figure 5D:
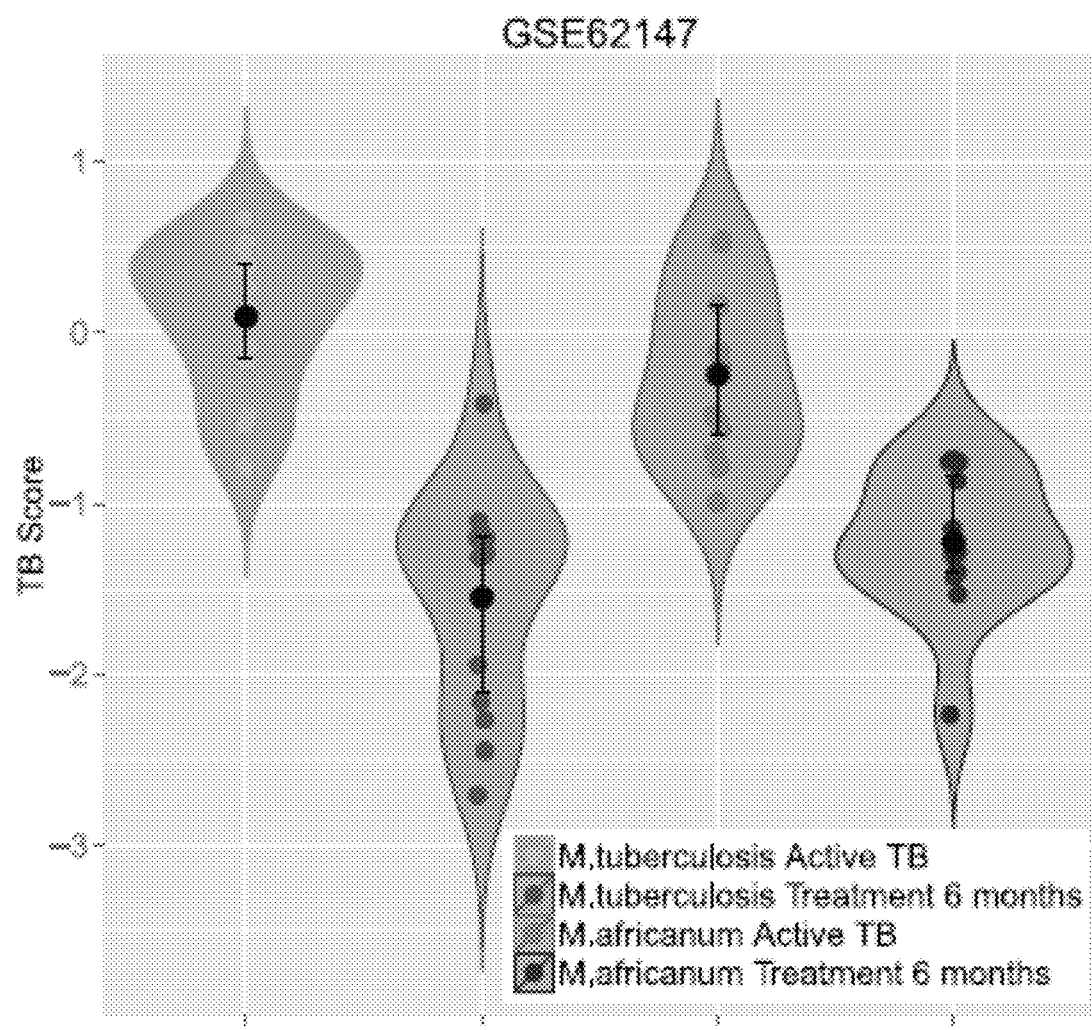
Figure 13A:
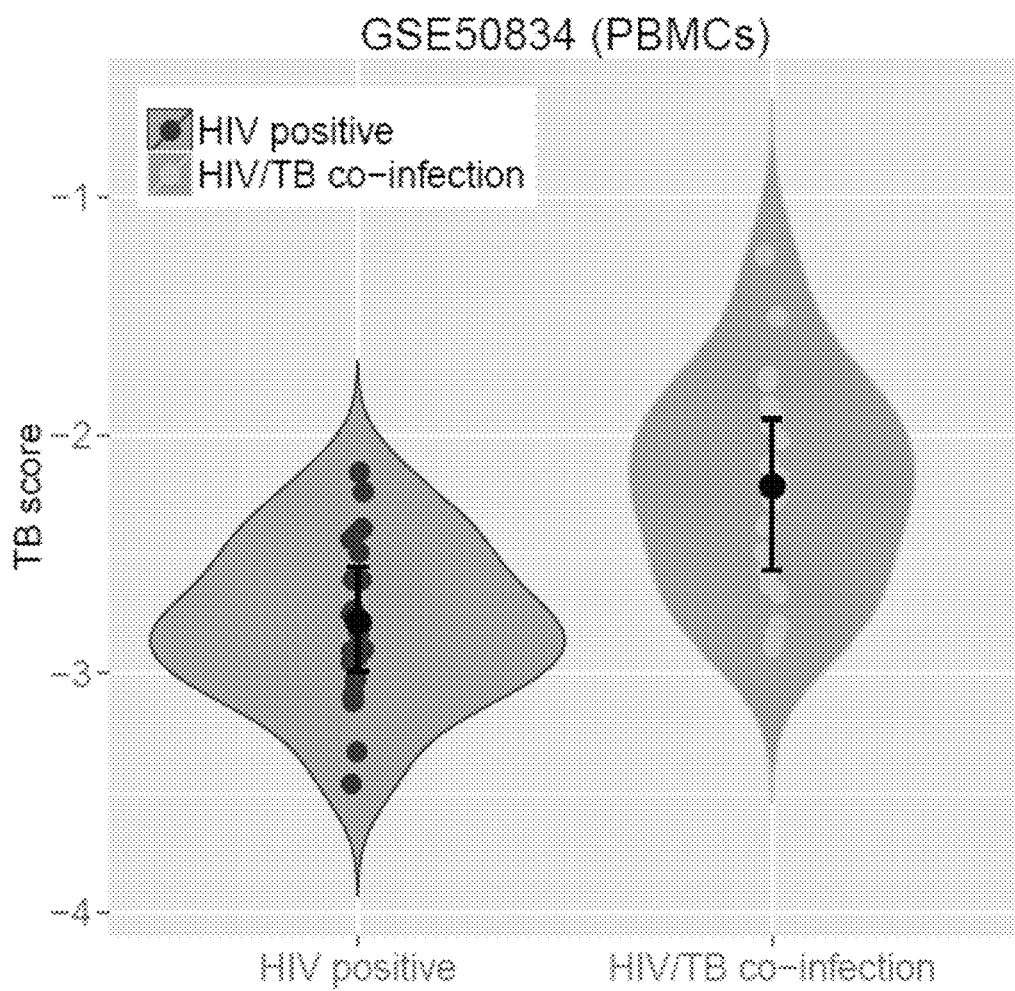
FIGS. 13A and 13B show the results for GSE50834, which compared PBMCs in HIV-positive patients to those with HIV/TB co-infection.
Figure 13B:
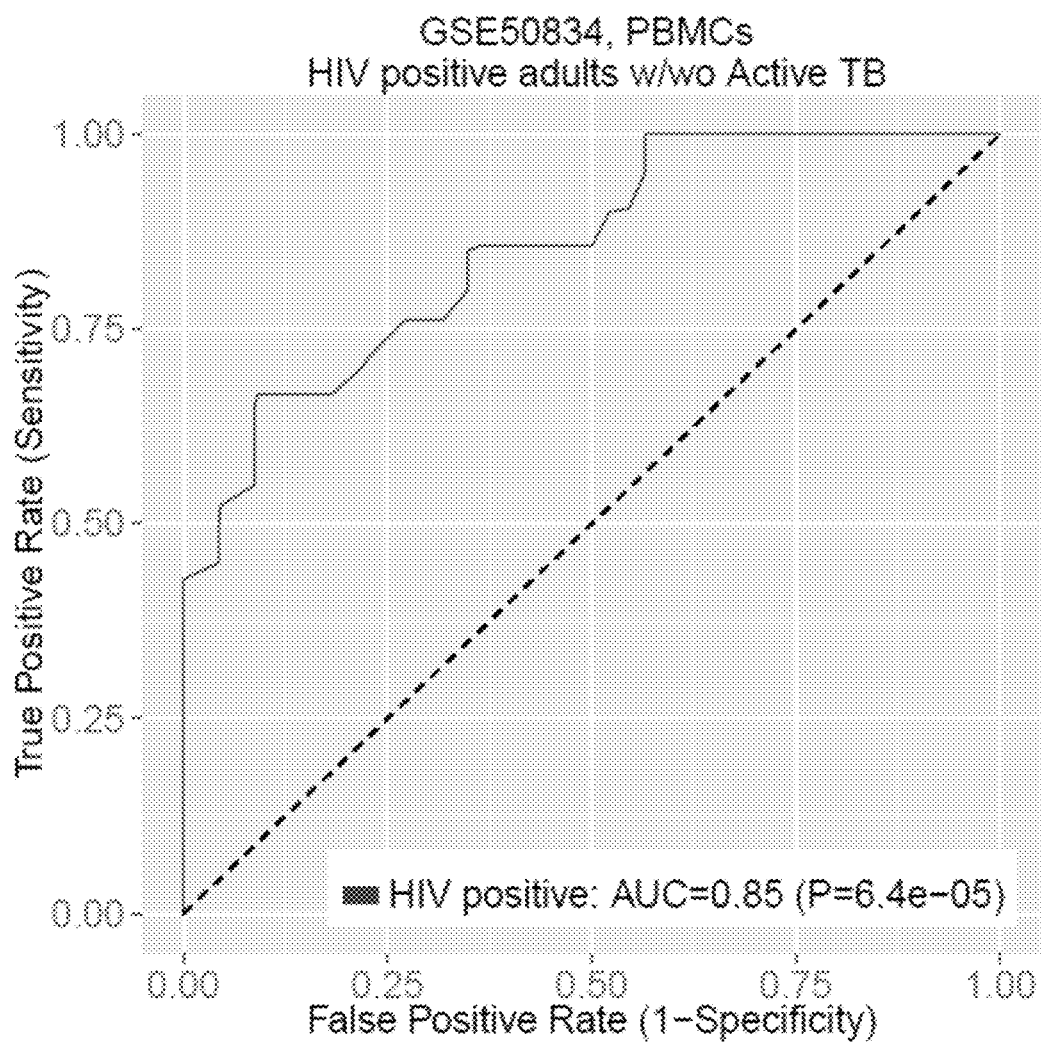

We next investigated the effect of several confounding factors (HIV co-infection, TB drug resistance and culture status, disease severity, and BCG vaccination) on the three-gene set. In three datasets (GSE37250, GSE39939, and GSE39940) that included ATB patients with or without HIV co-infection, there was no difference in the TB score AUCs for OD vs. ATB with or without HIV co-infection (FIGS. 4A-4C). In GSE37250, there was a decrease in TB score AUC for LTB versus ATB with HIV co-infection, though the AUC remained high for both groups (HIV negative AUC 0.97; HIV positive AUC 0.89). In addition, one dataset, GSE50834, examined PBMCs from HIV-positive patients with and without TB co-infection; here, the TB score had an AUC of 0.85, though there is no non-HIV infected cohort included (FIG. 13).

Figure 14A:
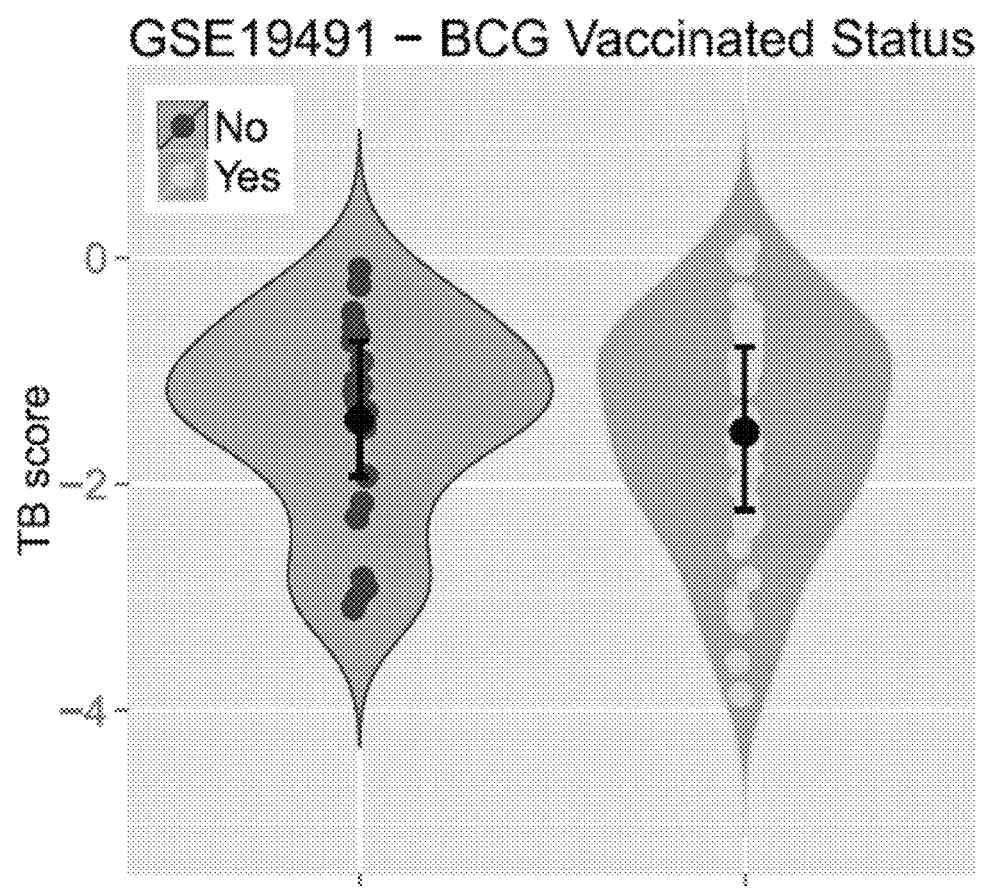
FIGS. 14A-14C show that in the GSE19491 dataset, the TB score was not affected by either (FIG. 14A) BCG vaccination status or (FIG. 14B) TB drug resistance status (both Wilcoxon p=NS), but (FIG. 14C) increased with X-ray disease severity (JT-test p<0.01).
Figure 14B:
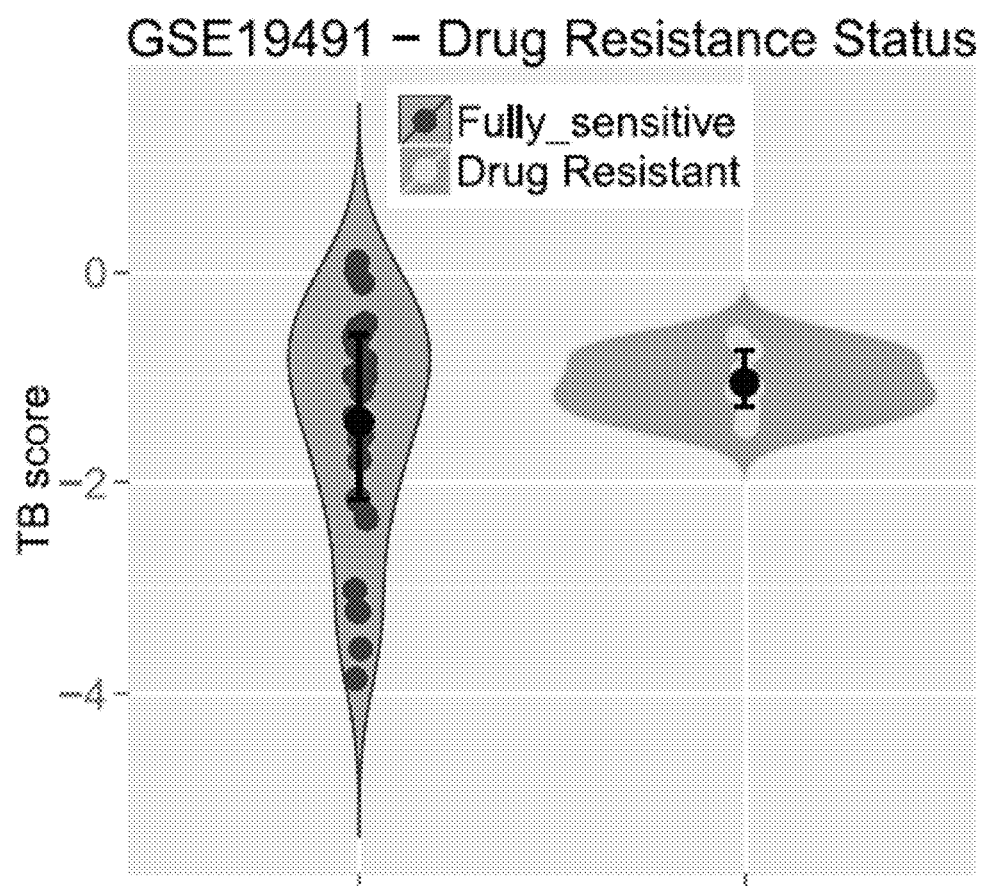
Figure 14C:
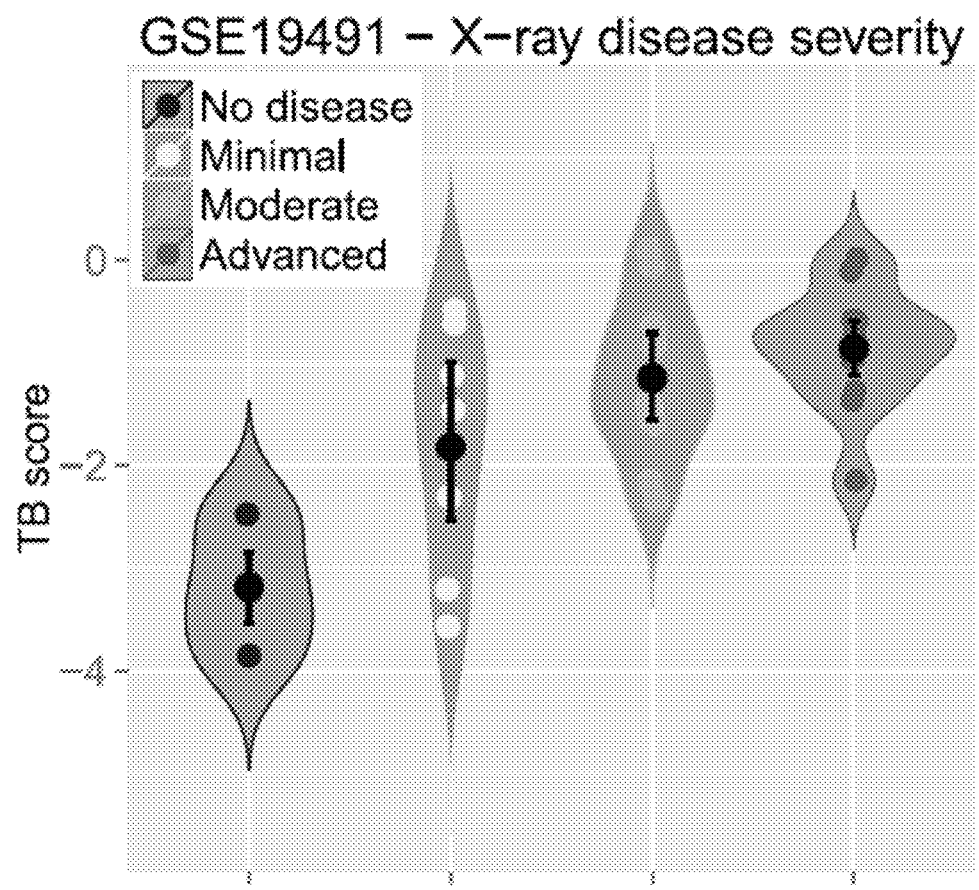
Figure 15A:
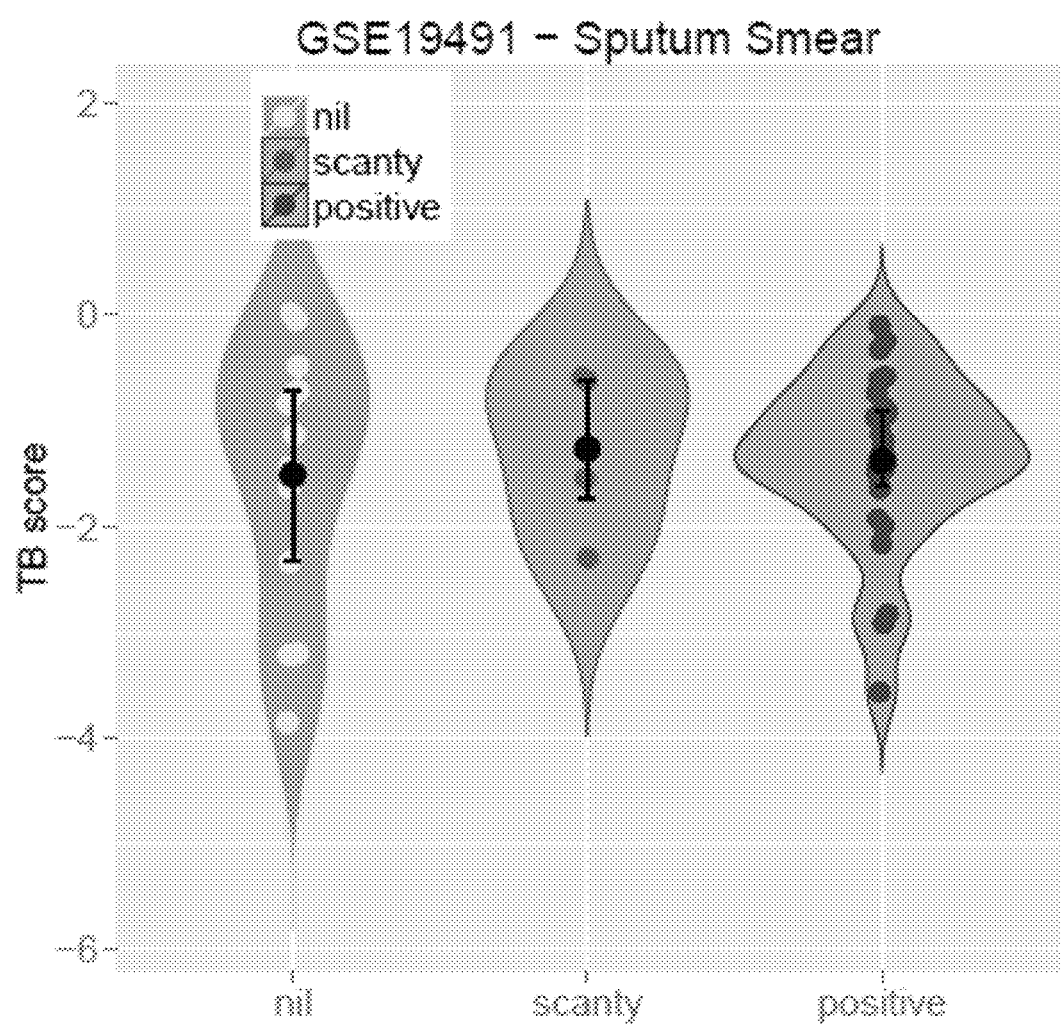
FIGS. 15A-15D show the TB score in ATB patients in GSE19491 according to (FIGS. 15A and 15B) sputum and (FIGS. 15C and 15D) BAL smear and culture results. There are many patients overlapping between the different figures; no ATB patients had both negative sputum culture and negative BAL culture. There is no significant effect of smear or culture positivity between in any group (Wilcoxon p=NS).
Figure 15B:
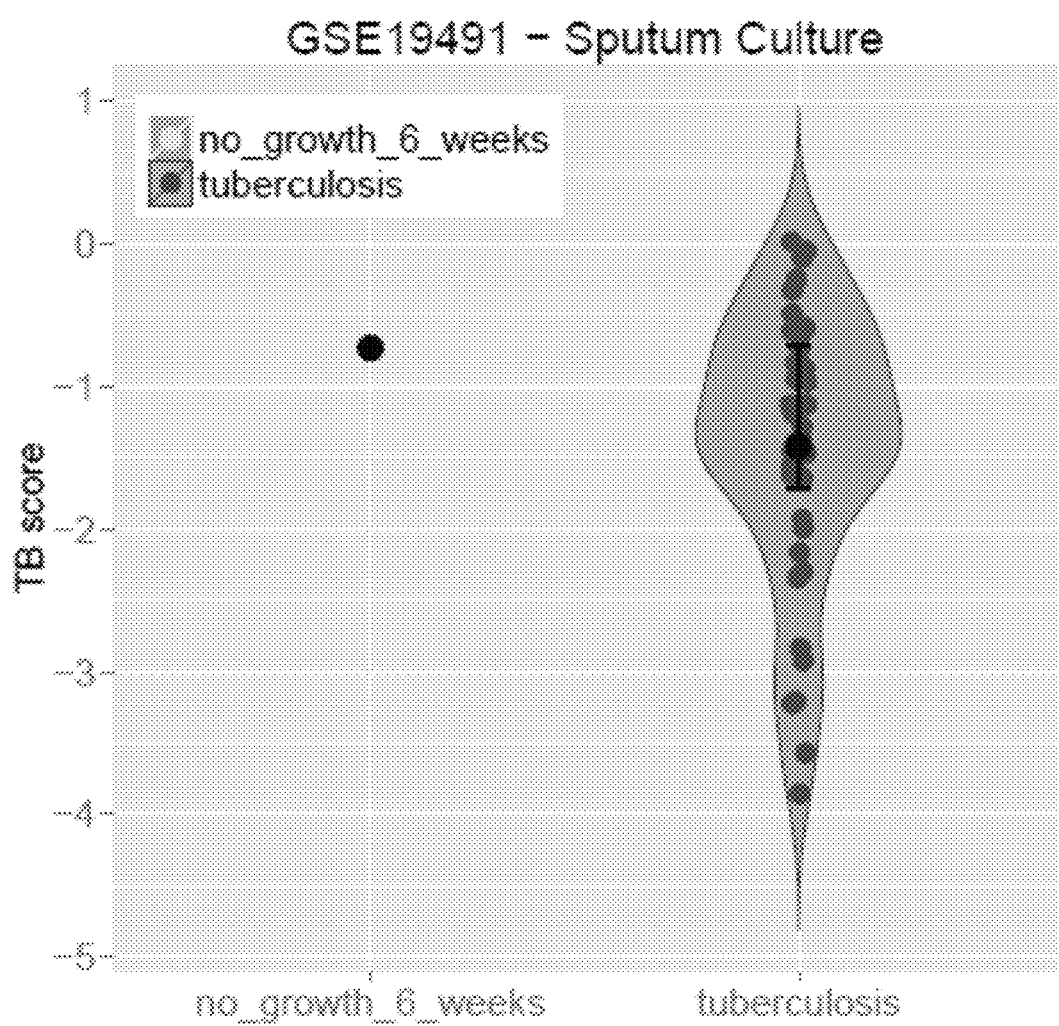
Figure 15C:
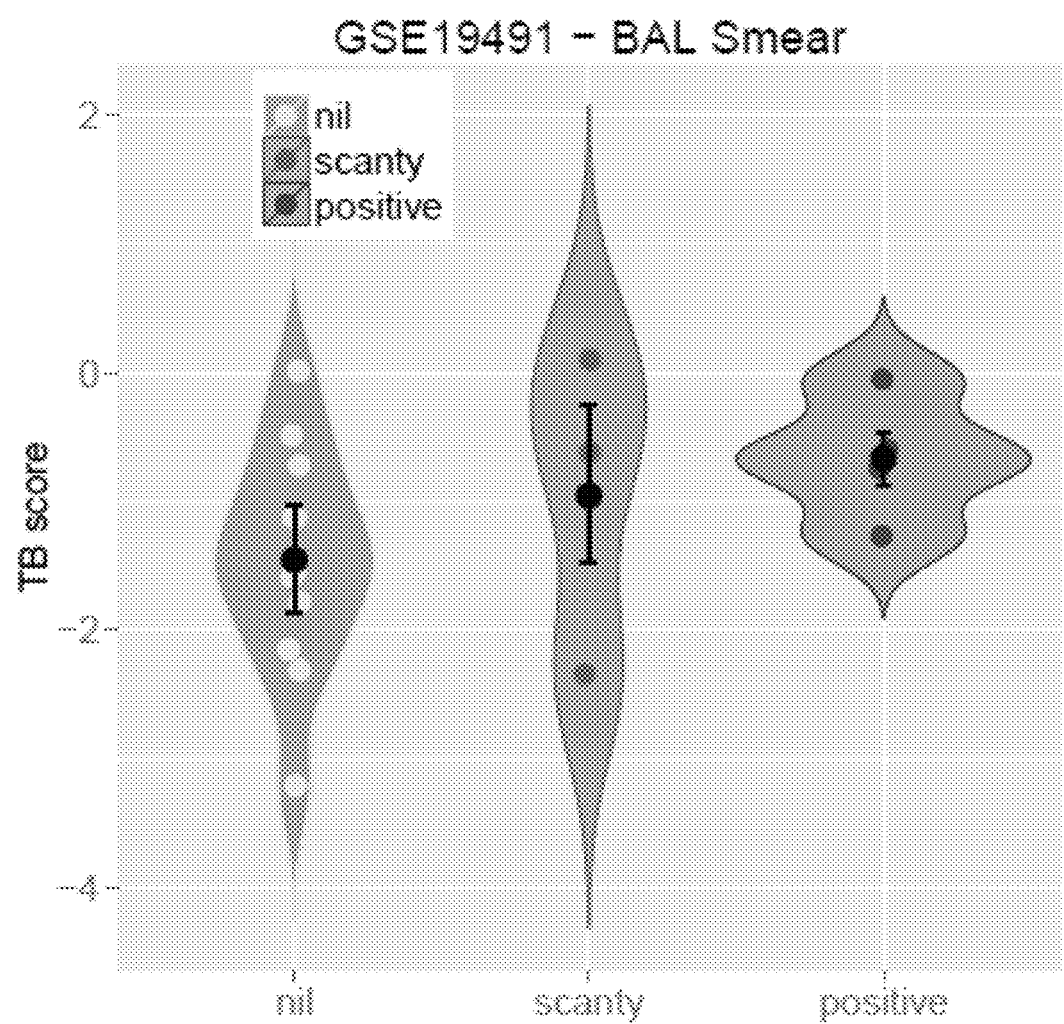
Figure 15D:
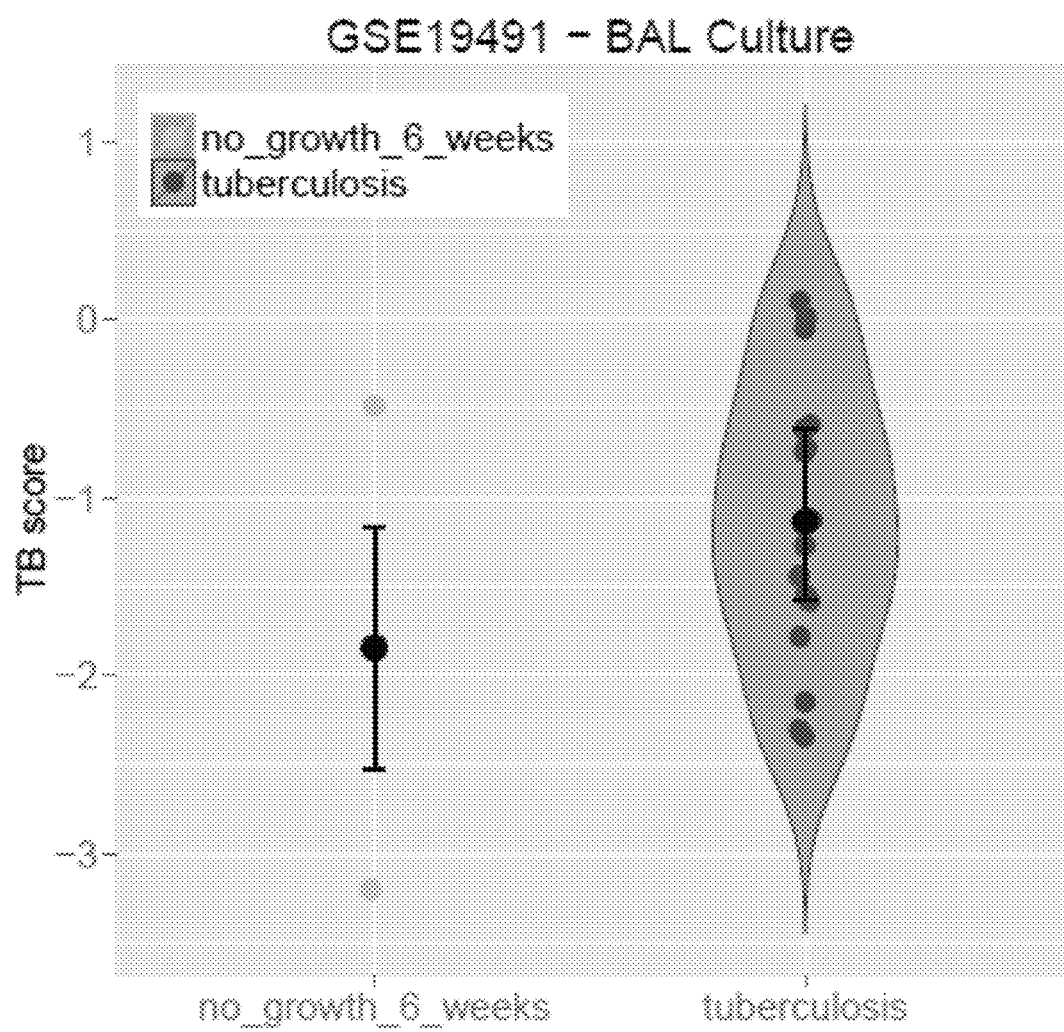

Examining confounders other than HIV, in GSE19491, there was no difference in the TB score due to BCG vaccination status or Mtb drug resistance. In addition, the TB score was positively correlated with disease severity (J-T test p<0.001) as defined by chest radiography (FIG. 14). The effects of culture status were pronounced in children. Two pediatric datasets, GSE39939 and GSE41055, included cohorts of culture-negative active TB patients. In these datasets, the TB scores in culture-negative ATB were significantly lower than in culture-positive ATB (P<0.05; FIG. 8). However, in GSE19491, in adults with culture-positive ATB, the degree of smear positivity, or a negative culture from either sputa or BAL when the other is positive, did not affect TB score (FIG. 15). These results suggest that a positive ATB classification via TB score in children would be highly specific for ATB, though may not be sensitive to culture-negative ATB children.

Next, we examined the four datasets that profiled A TB patients longitudinally during treatment (the Cliff Combined dataset (Cliff et al. (2013) J. Infect. Dis. 207:18-29), GSE40553 (Bloom et al. (2012) PLoS One 7, e46191), GSE56153 (Ottenhoff et al. (2012) PLoS One 7:e45839), and GSE62147 (Tientcheu et al. (2015) Genes Immun. 16(5):347-355); Table 1). Each of the four datasets followed ATB patients for up to 6 or 12 months. In each dataset, the TB score showed a significant decreasing trend as treatment progressed (FIG. 5, regression models in Table 5). Furthermore, most patients showed individual trends of decrease over time. In GSE56153, the TB scores of patients at recovery were not different from those of HCs (Wilcoxon P>0.05). In GSE62147, patients with ATB due to *M. africanum* were also examined; here, too, the TB score fell with treatment. These results suggest that the TB score may be a useful biomarker for clinical response to treatment, and could potentially identify treatment non-responders, though no non-responders were available for study here.

Figure 16A:
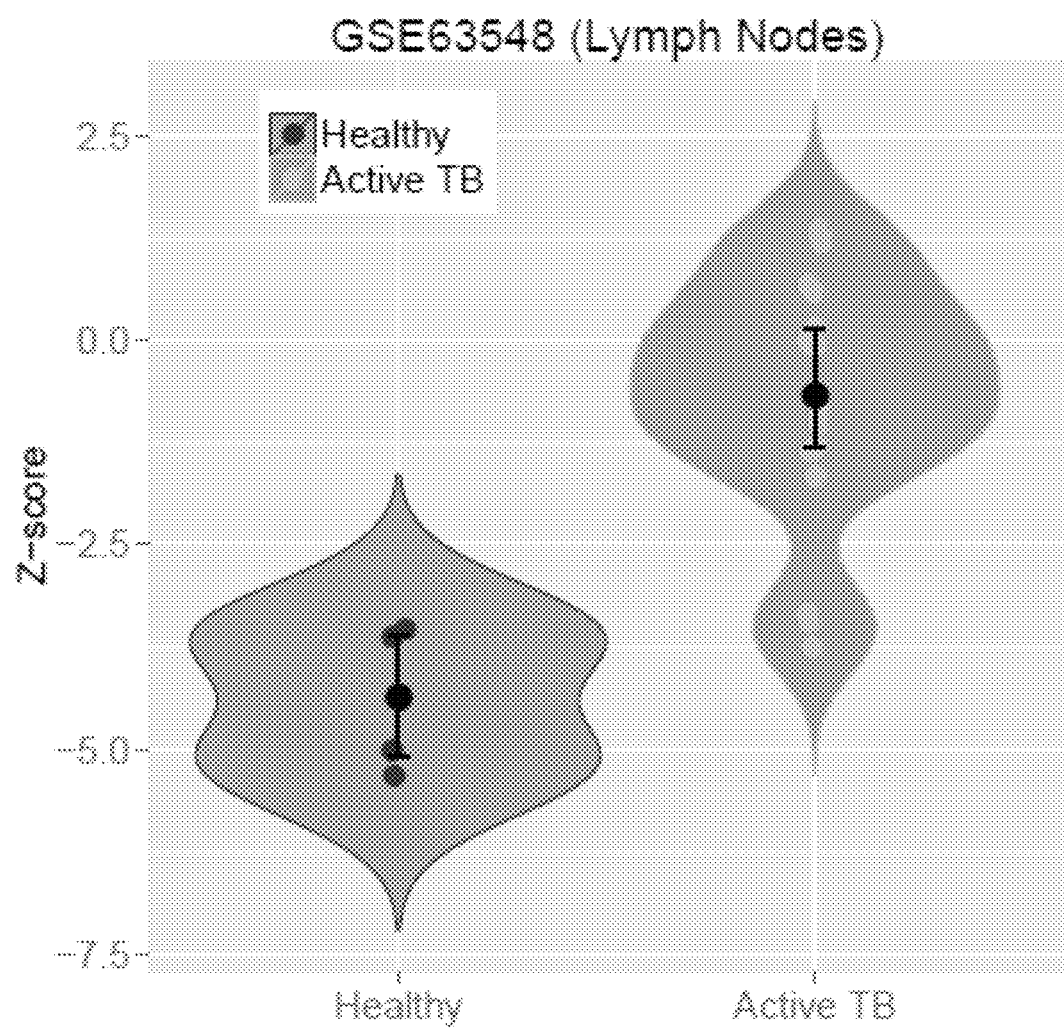
FIGS. 16A and 16B show results for GSE63548, which compared lymph node tissue between healthy controls and patients with extrapulmonary lymph node TB infections. The three gene set showed (FIG. 16A) a significant difference between the two groups, with (FIG. 16B) an ROC AUC of 0.98.
Figure 16B:
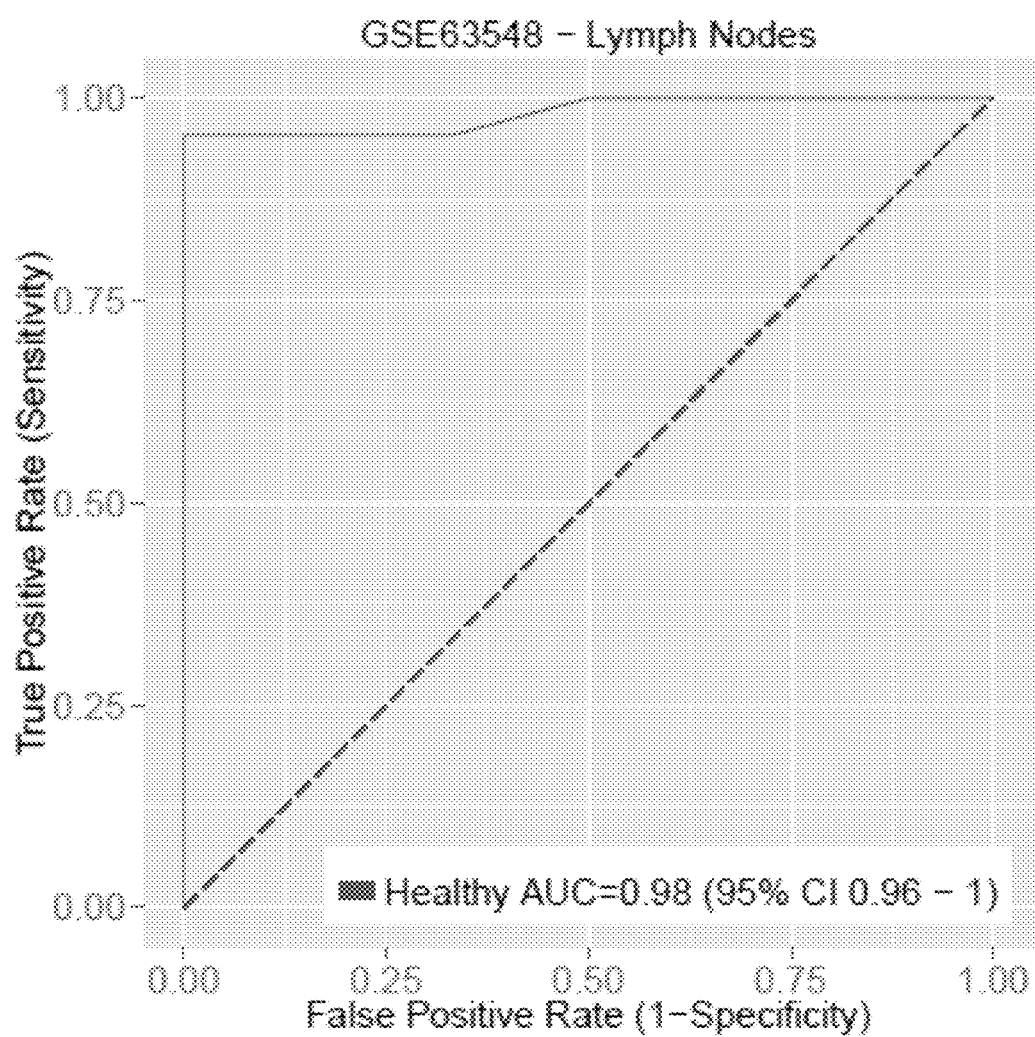
Figure 17A:
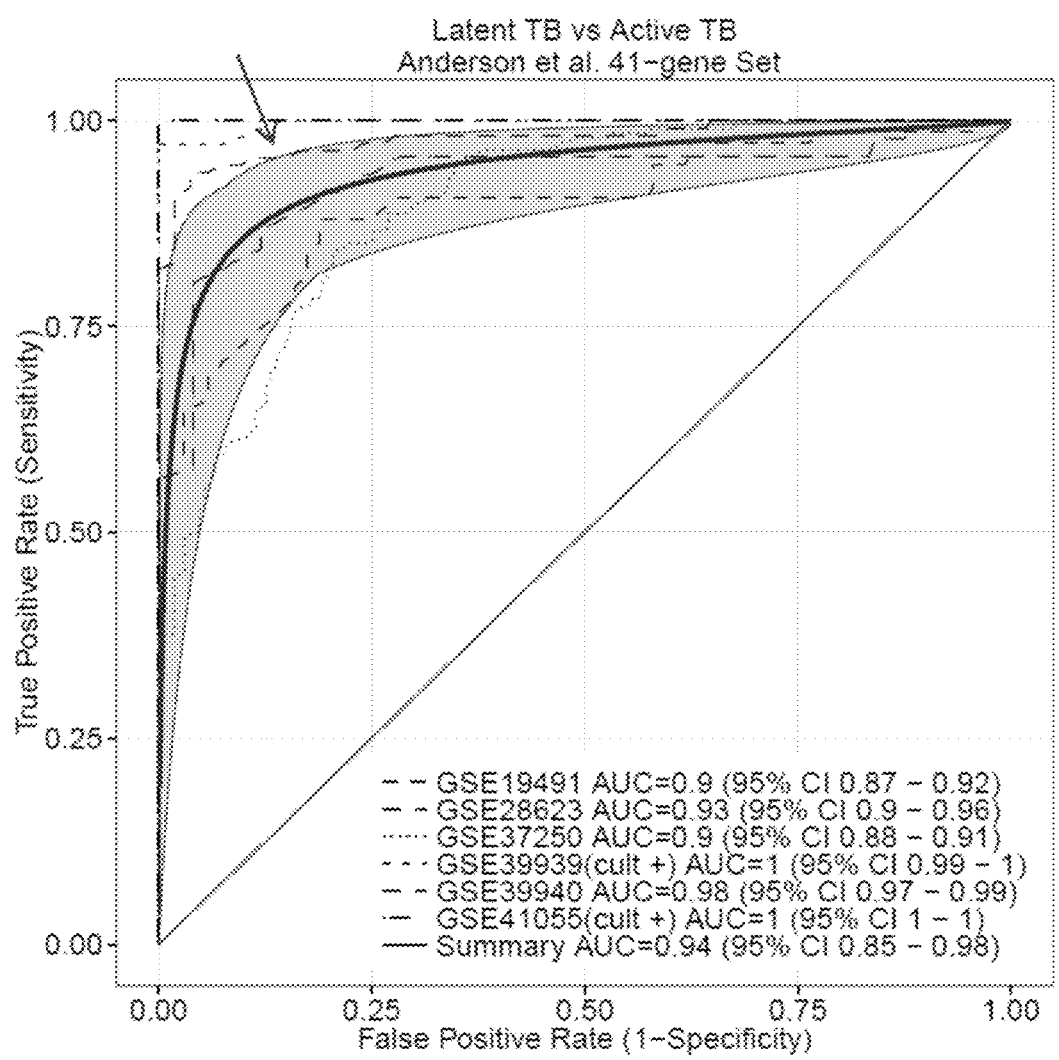
FIGS. 17A and 17B show summary ROC plots for the Anderson et al. (N. Engl. (2014) J. Med. 370:1712-1723) diagnostic gene sets in all publically available TB gene expression datasets. The arrows mark the discovery dataset (GSE39940).
Figure 17B:
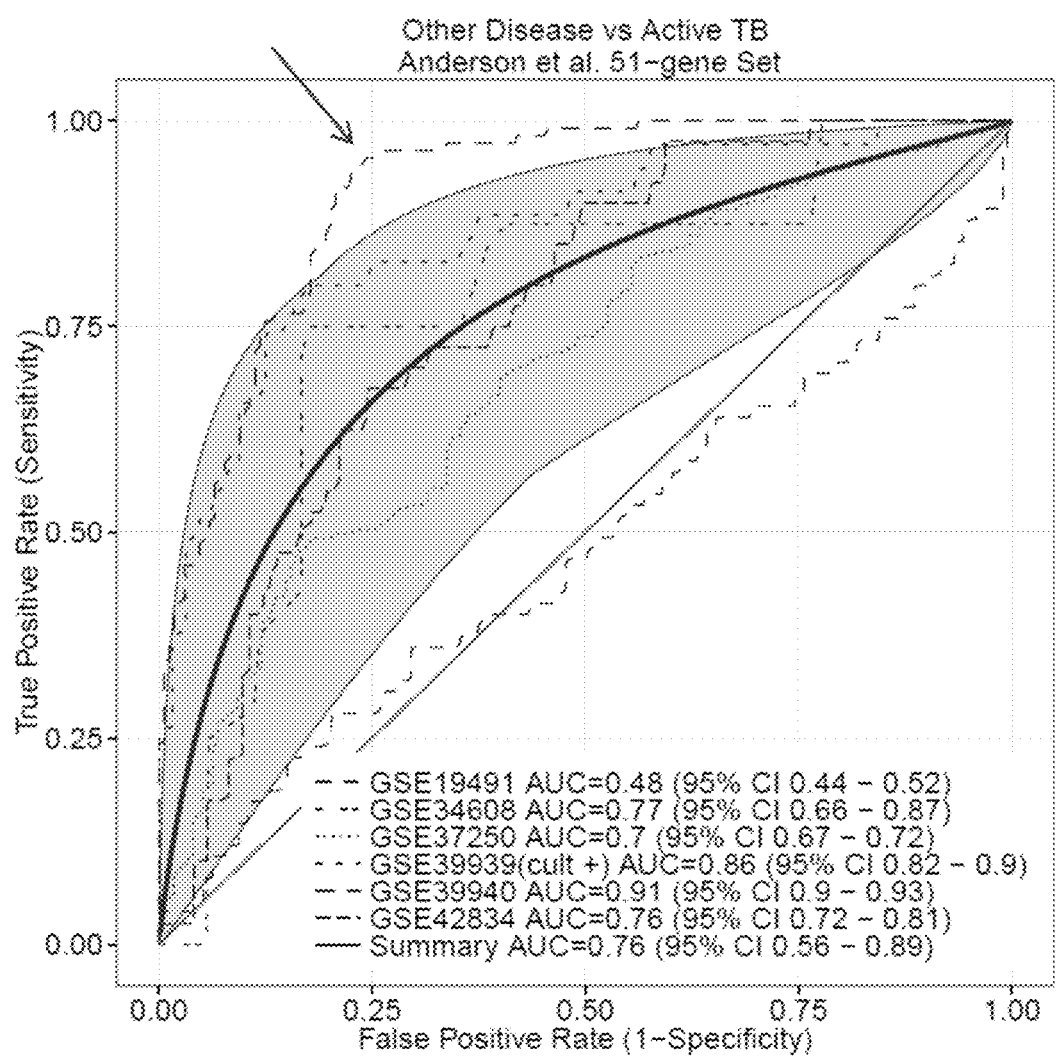
Figure 18A:
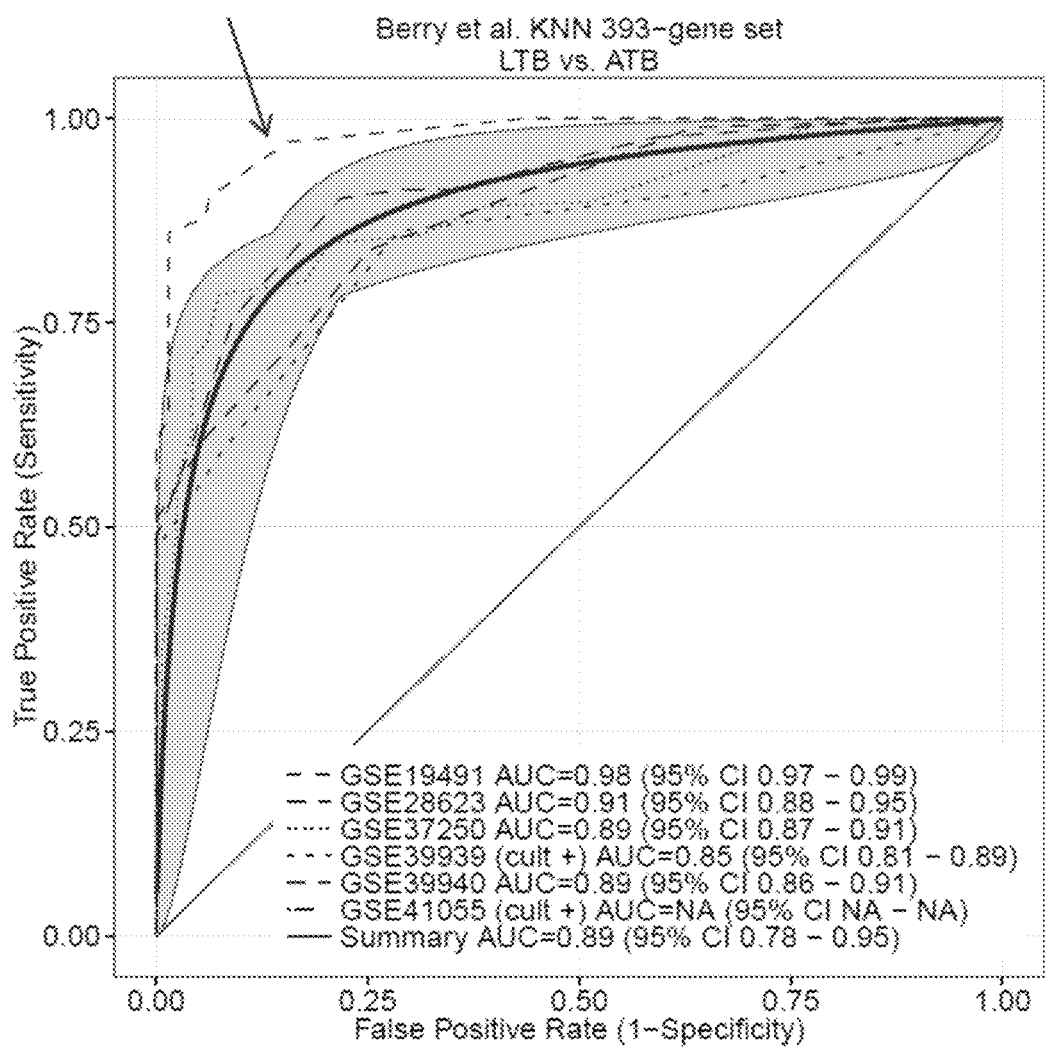
FIGS. 18A and 18B show summary ROC plots for the Berry et al. (Nature (2010) 466:973-977) diagnostic gene set in all publically available TB gene expression datasets. The arrow marks the discovery dataset (GSE19491 (FIG. 18A) Latent TB versus active TB.
Figure 18B:
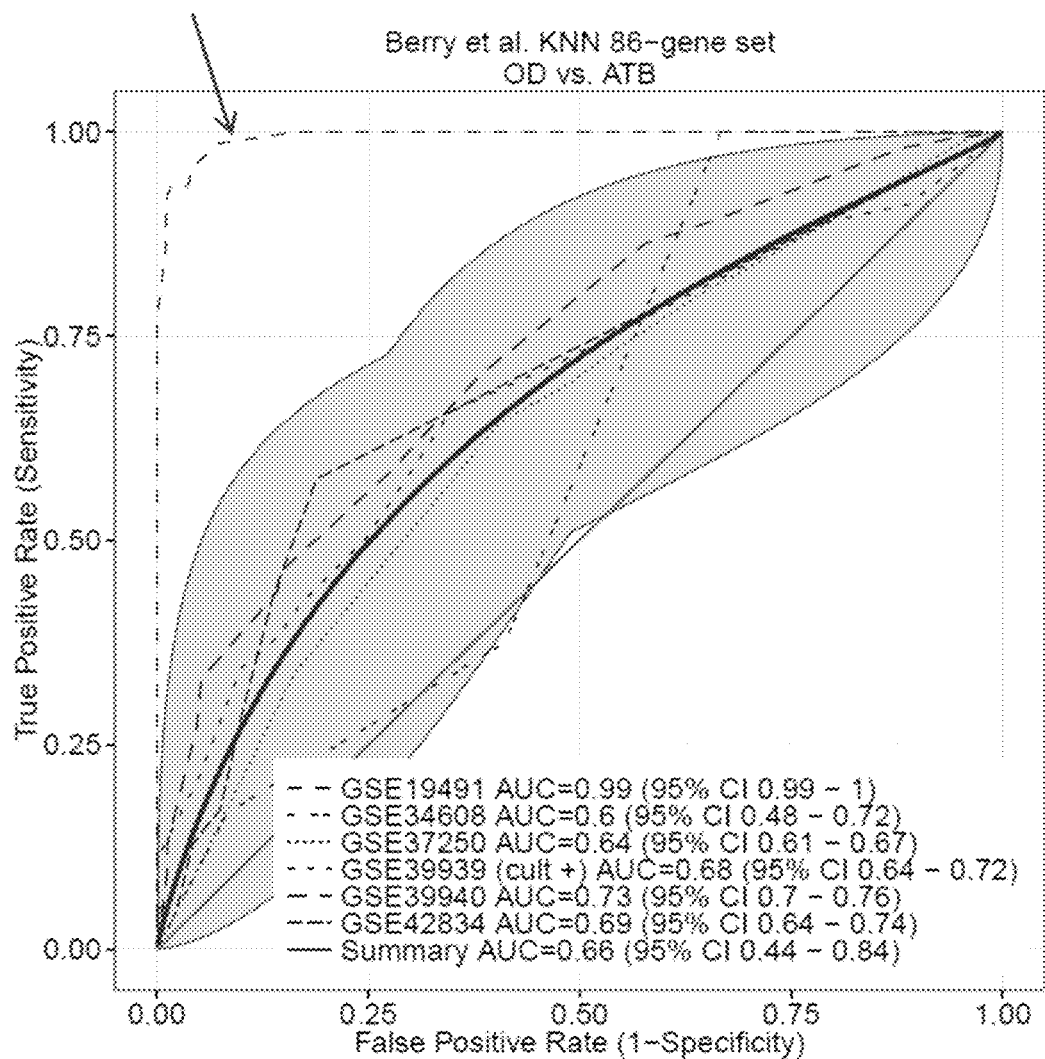
Figure 19A:
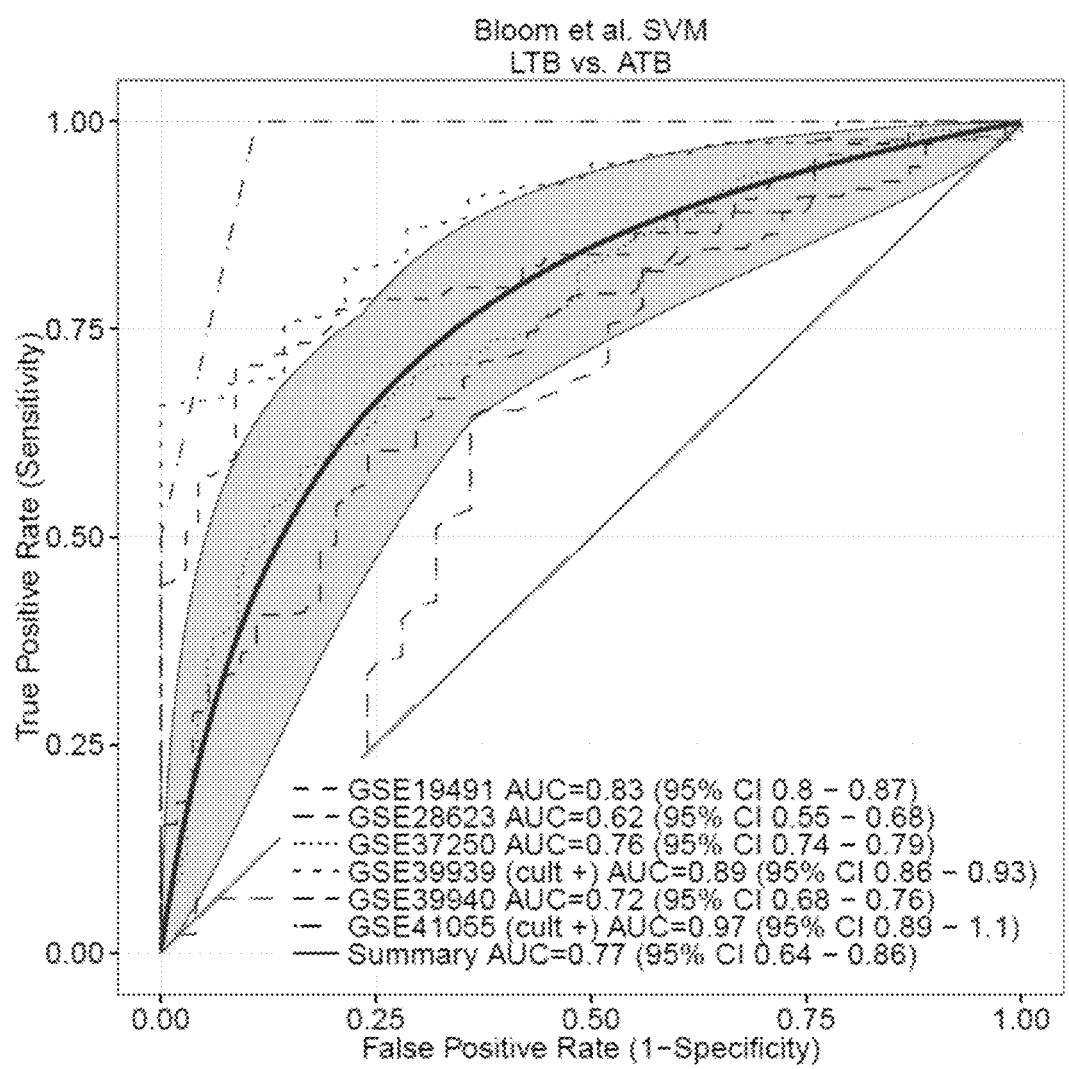
FIGS. 19A and 19B show summary ROC plots for the Bloom et al. (PLoS One (2013) 8:e70630) diagnostic gene set in all publically available TB gene expression datasets. The arrow marks the discovery dataset (GSE42834).
Figure 19B:
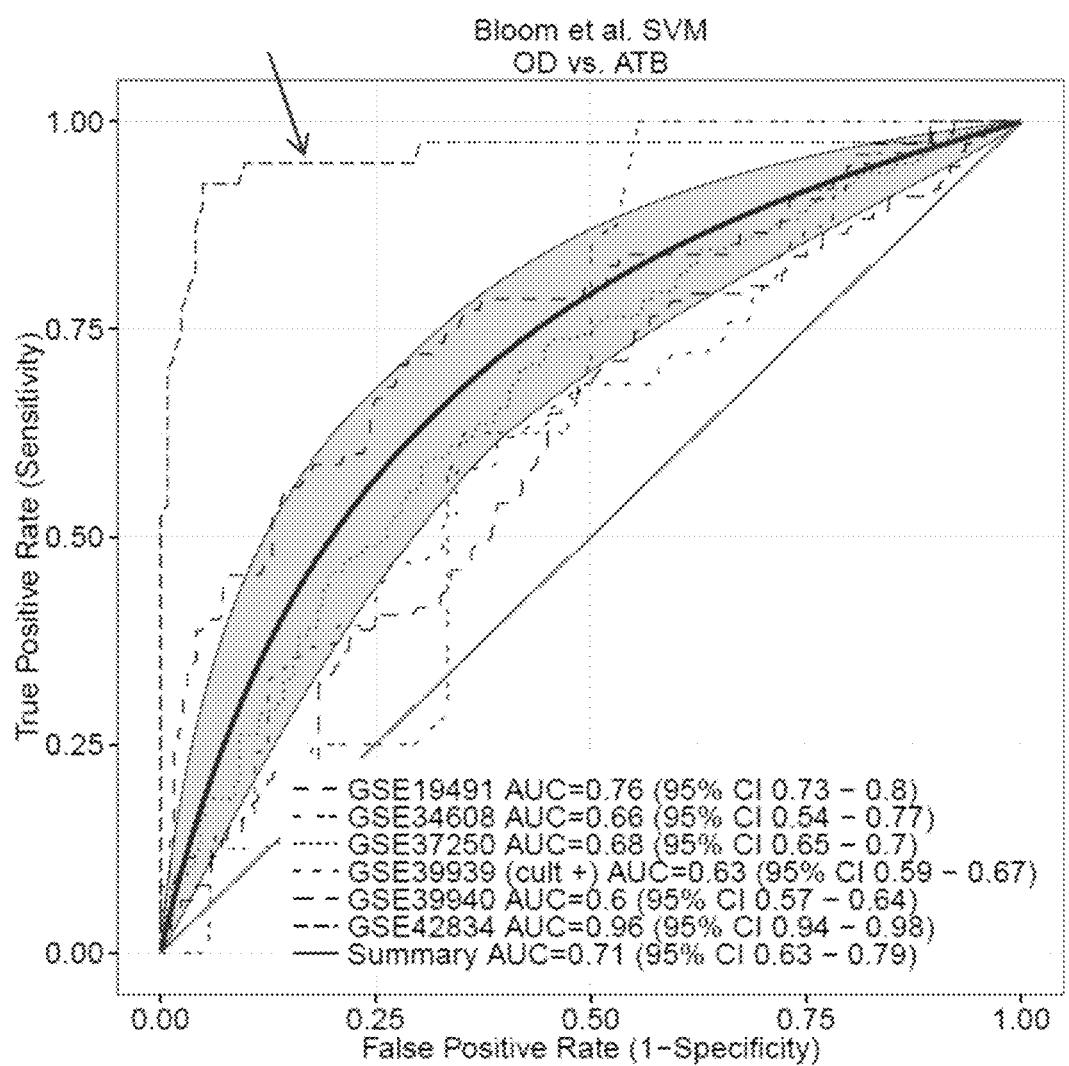
Figure 20A:
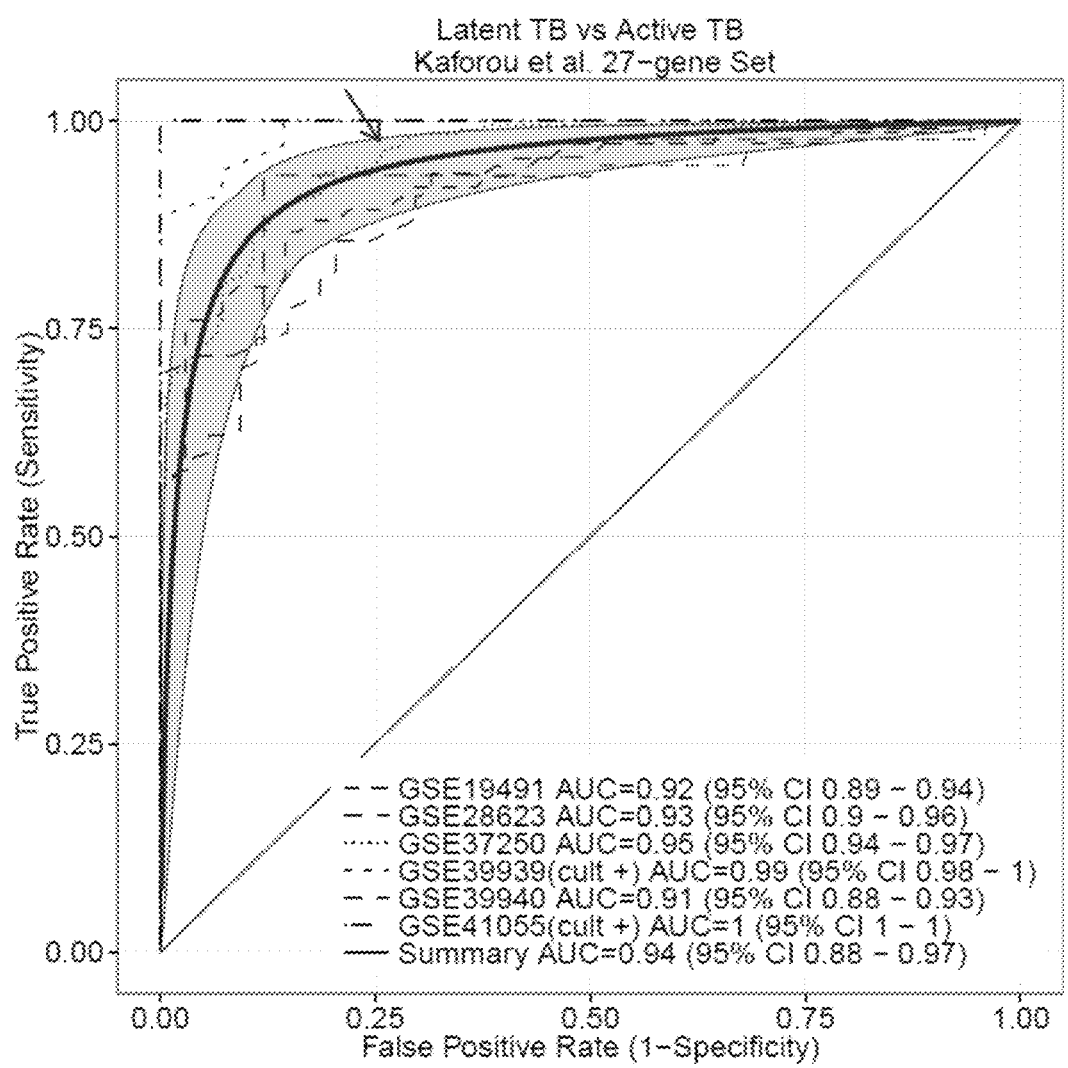
FIGS. 20A and 20B show summary ROC plots for the Kaforou et al. (J. Infect (2014) 69 Suppl. 1:S28-31) diagnostic gene set in all publically available TB gene expression datasets. The arrow marks the discovery dataset (GSE37250).
Figure 20B:
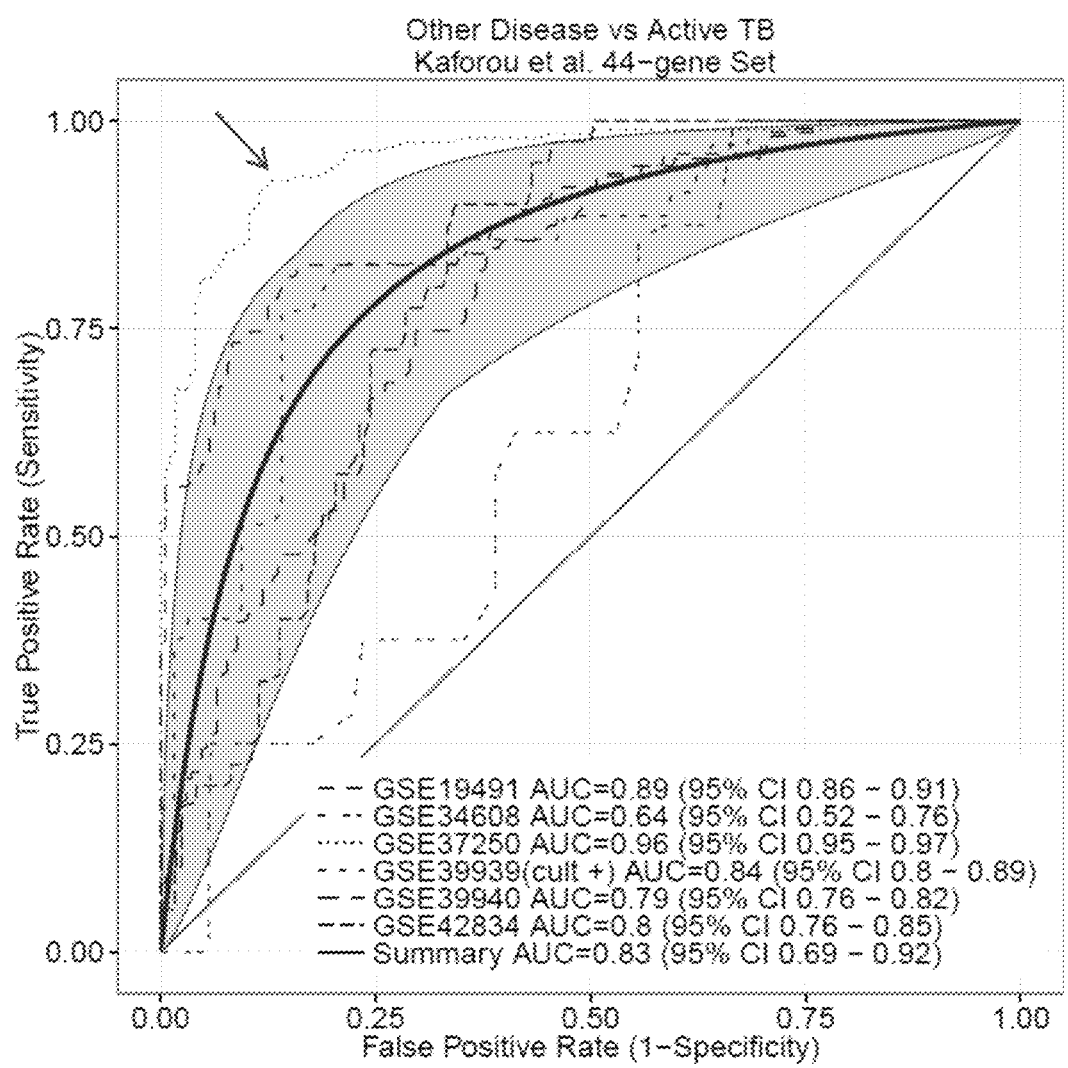
Figure 21A:
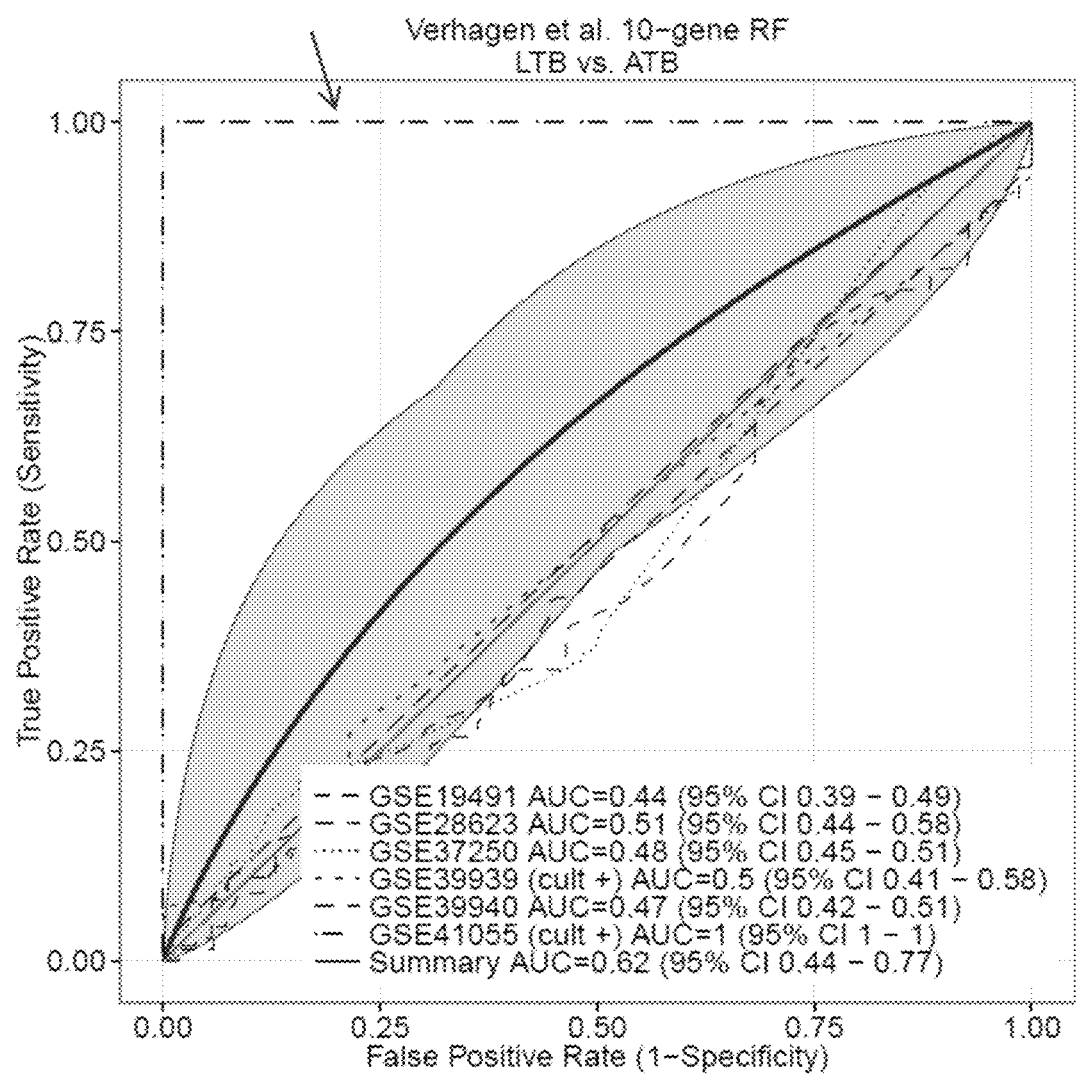
FIGS. 21A and 21B show summary ROC plots for the Verhagen et al. (BMC (2013) Genomics 14:74) diagnostic gene set in all publically available TB gene expression datasets. The arrow marks the discovery dataset (GSE41055).
Figure 21B:
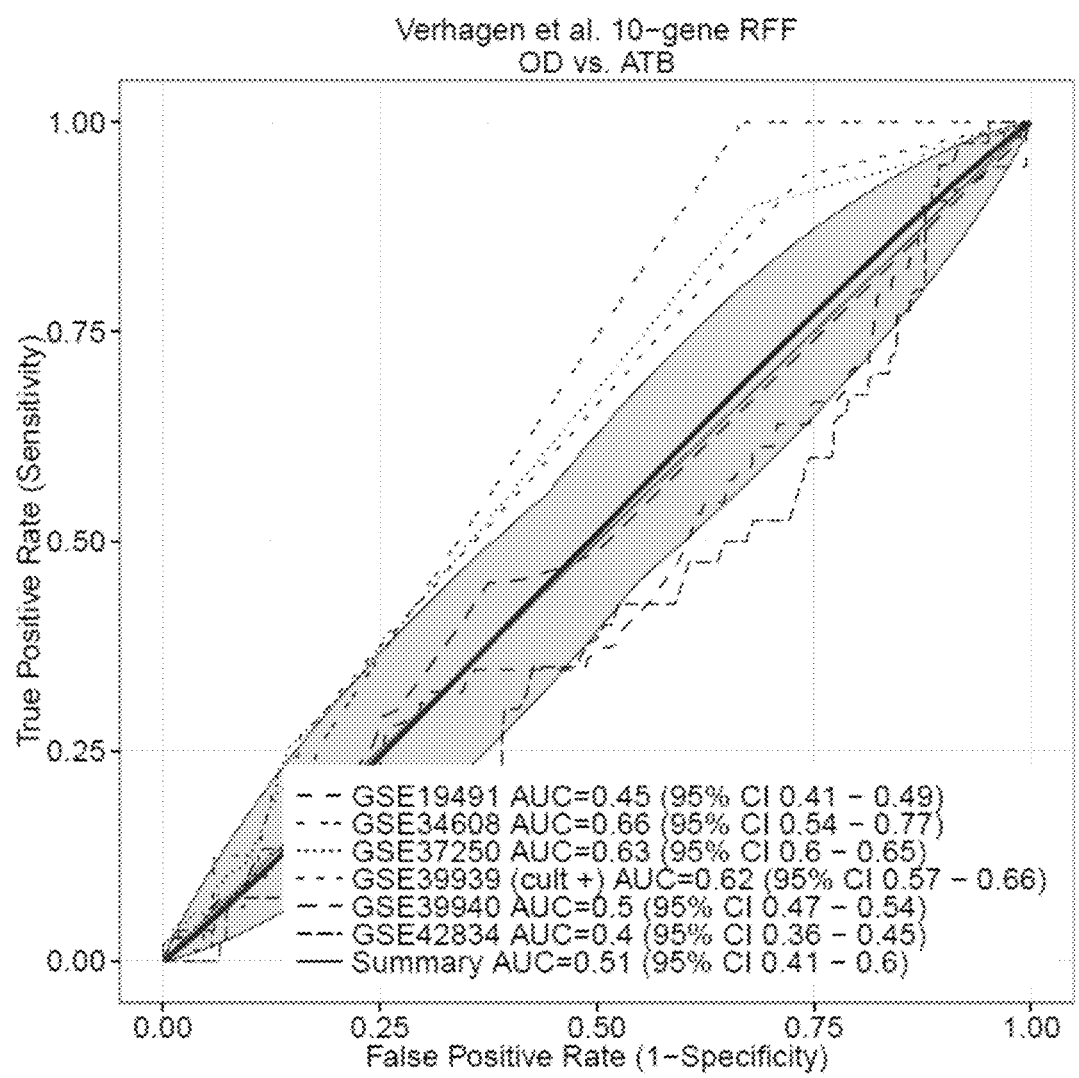
Figure 22A:
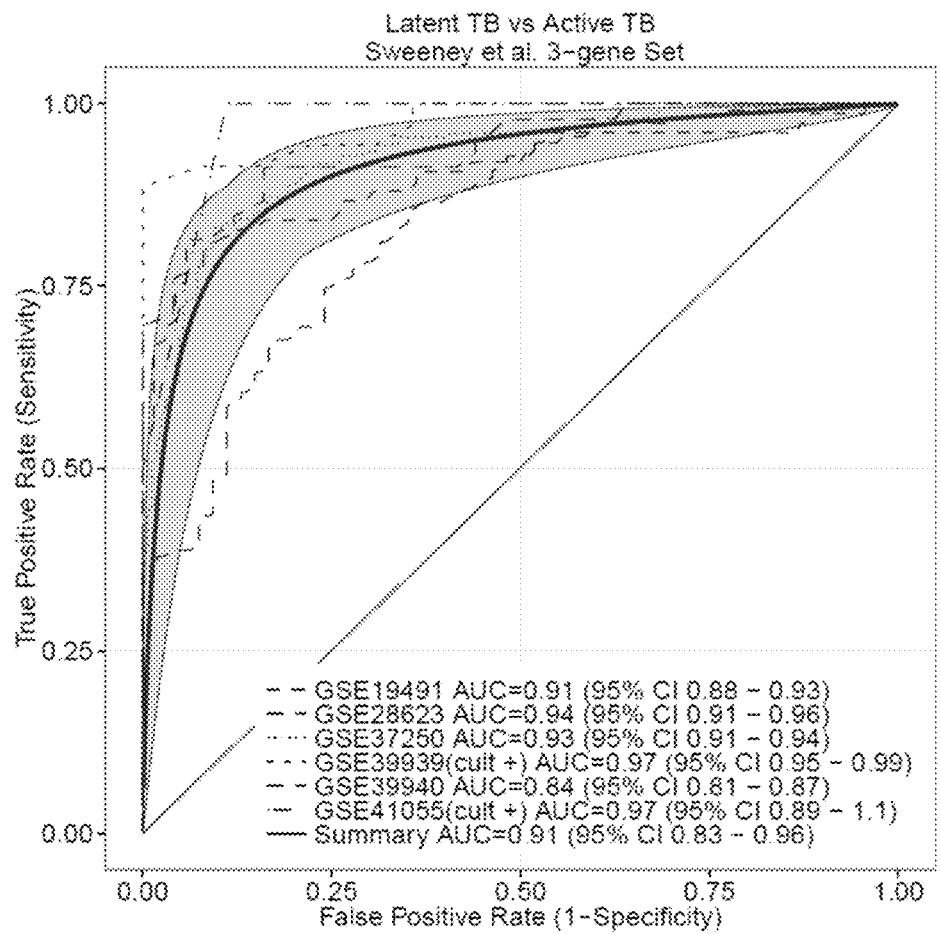
FIGS. 22A and 22B show the three-gene set is shown using the per-sample normalization score (as described in the text).
Figure 22B:
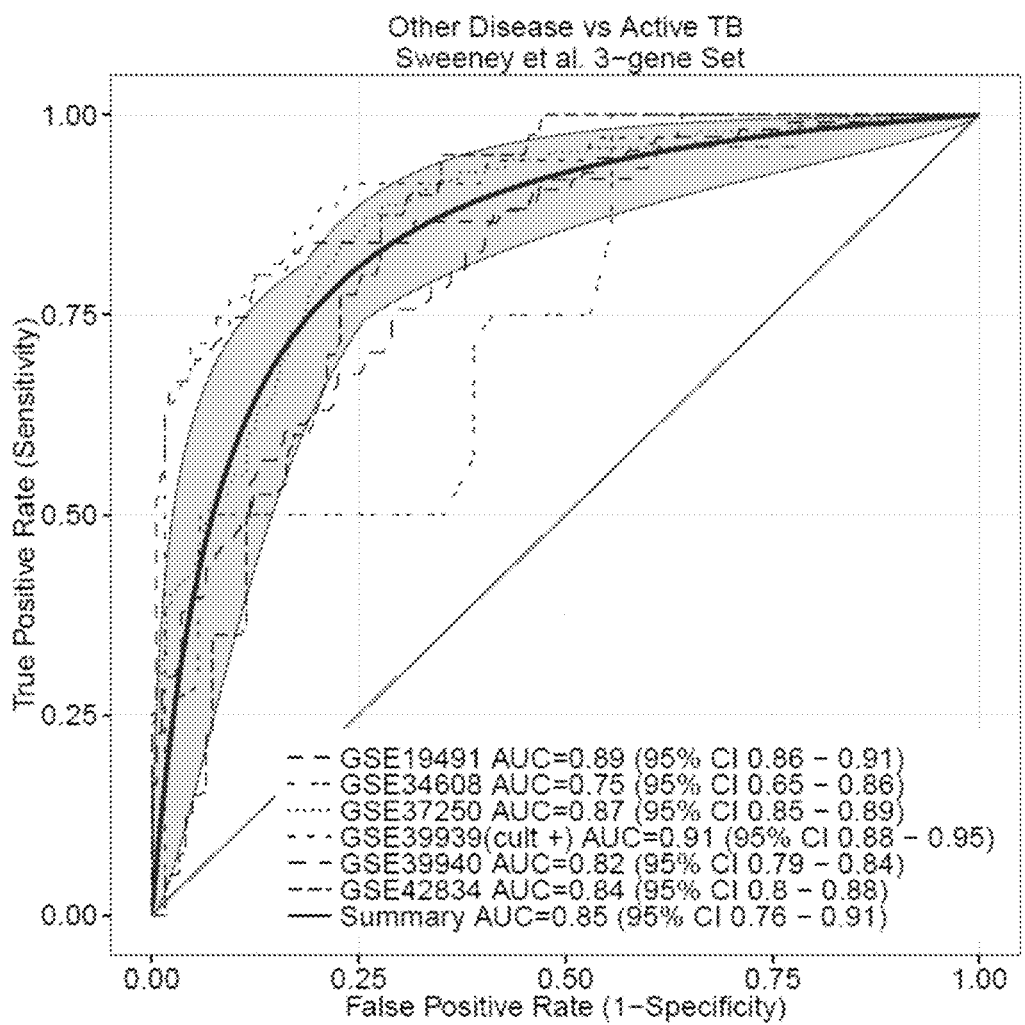

All datasets mentioned above examined pulmonary active TB; one question is whether the three-gene set might also be useful for diagnosis of extrapulmonary TB. One dataset, GSE63548, compared TB-infected lymph node tissue to lymph nodes from healthy controls (D-2087, Transcriptomic and Proteomic profiling of lymph node tissue infected with *Mycobacterium tuberculosis*. American Society for Microbiology 114th Meeting (2014)); here, the TB score had an ROC AUC of 0.98 (FIG. 16). However, since this study was conducted in actual lymph node tissue, not peripheral blood, further work will be necessary to assess the utility of the TB score in extrapulmonary TB.

Several of the studies used in our analysis have previously identified transcript or gene sets for diagnosing ATB patients (Anderson et al. (2014) N. Engl. J. Med. 370:1712-1723, Kaforou et al. (2014) J. Infect. 69 Suppl 1:S28-31, Berry et al. (2010) Nature 466:973-977, Bloom et al. (2013) PLoS One 8:e70630, Verhagen et al. (2013) BMC Genomics 14:74). However, these gene sets either contain large number of genes or are not generalizable, or both. We tested eight previously published diagnostic gene sets from five studies for their ability to discriminate OD and LTB from ATB in all datasets examined here (FIGS. 17-22). Each gene set was tested across all datasets using the method described in its original paper; for methods that require models, such as k-nearest neighbors (Berry et al., supra) or support vector machines (Bloom et al., supra), the model was constructed using the entire original discovery cohort, and then tested in the other independent cohorts. Most gene sets have a significant drop in discriminatory power in independent validation datasets. Only the two gene sets from Kaforou et al. ((J. Infect (2014) 69 Suppl. 1:S28-31) performed as well as our three-gene set when comparing basic diagnostic power. However, the two Kaforou et al. gene sets contain 71 genes (including just one of our genes, DUSP3), precluding their clinical application in resource-limited environments; in contrast, our three-gene set could be optimized to a low-cost platform.

Finally, we investigated the expression of both the entire set of 266 significant genes and the diagnostic three-gene set in publicly available whole genome expression profiles from 25 different types of immune cells. Both gene sets showed a statistically significant enrichment in M1 macrophages (P<0.05) (FIG. 23). Since macrophages polarize to M1 after interferon gamma (IFN gamma) treatment, these findings confirm the role of IFN gamma in the host response to ATB. The three-gene set may thus give insight into the host response to active pulmonary TB.

Discussion

A critical requirement in reducing the global burden of tuberculosis disease is better tools for diagnosis and for monitoring treatment response. Here, we used a multi-cohort analysis of three public TB gene expression datasets composed of 1,023 whole blood patient samples across a wide range of ages, enrolling countries and inclusion criteria to find statistically differentially expressed genes in ATB compared to LTB and OD. We identified a three-gene set, and validated in 10 additional independent whole blood datasets composed of 1,461 samples to demonstrate that it is robustly diagnostic for ATB versus healthy controls, latent TB, and other diseases that is invariant to HIV status and BCG vaccination, and is significantly correlated with ATB severity.

Several TB diagnostic gene sets have been proposed by others; five of the datasets used here were published with one or more sets of diagnostic gene sets. When comparing these published gene signatures, there is minimal overlap among them. In addition, larger gene sets do not have better generalizability or diagnostic power. Single-study discovery analyses that rely on machine learning models are prone to overfitting, and thus suffer from a lack of generalizability (Table 6 and FIGS. 17-22). Each gene set was tested using its original described model using all data from its original dataset. These comparisons of AUCs are thus a reasonable estimate of the real-world validation of the various gene sets and models. Overall, in comparison to all other published TB gene sets, ours is parsimonious (only three genes), can distinguish both OD and LTB from ATB with a single test in multiple clinical groups, and performs well in independent, external datasets.

We provide strong evidence that our three-gene set addresses a number of significant challenges in ATB diagnosis. First, it is based on peripheral blood, and as such its clinical application does not require complex procedures or patient production of adequate sputa. Second, our three-gene set performed well in diagnosing culture-positive ATB in children, a target population in need of more efficient and accurate diagnosis. We note that the three-gene set was not able to diagnose the culture-negative pediatric ATB patients (though the PPV of the test could still be of significant clinical benefit). Finally, HIV status did not change the diagnostic power of the three-gene set for OD versus ATB comparisons, and while HIV+ patients had a lower AUC for LTB vs. ATB, it was still high (0.97 HIV−, 0.89 HIV+). By addressing these clinical challenges of the existing TB diagnostics, the three-gene set would be a useful clinical adjunct to current TB diagnostic methods.

Another critical and unmet need is the ability to perform quantitative monitoring of TB treatment response. The current standard in clinical trials for new drugs for TB treatment requires waiting for two years after treatment to observe relapse rates. Improved monitoring techniques might allow non-responders to be identified earlier. The three-gene set increases with disease severity and decreases with time of treatment (returning to the same level as healthy controls at the end of treatment) with remarkably similar coefficients across datasets (the TB score fell by 0.02 to 0.05 per week). This consistency across multiple datasets suggests the potential for detecting deviations from the 'standard' treatment response using our three-gene set, and identifying treatment non-responders significantly earlier. The correlation of the TB score with disease severity also suggests that it might be possible to leverage the test for a predictive enrichment strategy for new drug trials (Temple (2010) Clin. Pharmacol. Ther. 88:774-778). Leveraging the three-gene set to improve TB drug trials is thus a tantalizing possibility that requires further study.

The small size of the three-gene set will be important in its ultimate clinical application, reducing costs and complexity relative to larger gene sets. Multiplex PCR can become exponentially more difficult with additional targets, but a small set can be run in parallel. For instance, Cepheid's GeneXpert MTB/RIF assay measures the expression of five loci, and costs between $10-$20 per cartridge[25]. Using this assay as an approximate benchmark, an assay to measure the three-gene set could likely be provided at similar cost after commercial optimization.

Finally, the importance of the innate immune response and lung resident macrophages in the establishment of TB infection is well known (Dorhoi et al. (2014) Semin. Immunol. 26:533-542). However, there is still a lack of understanding of the specific cellular mechanisms enlisted during a host response to mycobacteria. We have here identified host response genes to ATB that are strongly associated with innate immune cells, in particular M1 macrophages. The three genes are known to have roles in immune regulation and infection response. GBP5 promotes assembly of both the AIM2 and NLRP3 inflammasomes assembly in response to pathogenic bacteria (Shenoy et al. (2012) Science 336: 481-485, Meunier et al. (2015) Nat. Immunol. 16:476-484). DUSP3 is a known regulator of both JNK and ERK signaling (Ishibashi et al. (1992) Proc. Natl. Acad. Sci. USA 89:12170-12174, Alonso et al. (2001) J. Biol. Chem. 276: 4766-4771). KLF2 has been shown to be downregulated in macrophages in response to bacterial stimulation; further, knockdown/knockout studies have shown that decreased KLF2 leads to a pro-inflammatory phenotype (Mahabeleshwar et al. (2012) J. Biol. Chem. 287:1448-1457, Das et al. (2012) Curr. Mol. Med. 12:113-125, Lingrel et al. (2012) Circ Res 110:1294-1302). Further hypothesis-driven studies of these three genes will provide better insight into both the global and the local immune response during TB infection and may help design more effective therapeutics and vaccines.

Arguably, one weakness in our study is that the global ROCs required a re-centering of means to accommodate for changes in baseline gene expression measurement by different technologies. However, such a centering is justified because in a real-world application of the three-gene set, the same technology with a global mean will be used across all cohorts. Furthermore, when the three-gene set is reduced to a targeted assay, the present public data can be mapped to the background gene expression levels of the final clinical platform in order to leverage the public data to set optimal cutoffs for future diagnosis. Thus, although the optimal cutoffs could change in the final commercial form, our results show that the three-gene set could be developed as a clinical test with a single cutoff for diagnosis of ATB.

Overall, the data presented here show that our three-gene set is robustly diagnostic for ATB. The three-gene set may improve clinical diagnosis and treatment response monitoring. It is based on whole blood and is robust to multiple clinical confounders. The parsimony of the three-gene set should ease translation to clinical practice and may prove cost effective in the austere environments in which TB is often diagnosed.

Methods

The purpose of this study was to analyze multiple gene expression datasets to identify a set of genes that can robustly separate patients with ATB from those with LTB or OD using a previously described integrated multi-cohort analysis framework (Khatri et al. (2013) J. Exp. Med. 210:2205-2221, Sweeney et al. (2015) Sci. Transl. Med. 7:287ra271, Chen et al. (2014) Cancer Res 74:2892-2902).

We searched two public gene expression microarray repositories (NIH GEO and ArrayExpress) for all human gene expression datasets that matched any of the following search terms: tuberculosis, TB, and mycobact[wildcard]. We retained datasets that examined clinical cohorts of active pulmonary tuberculosis infection in whole blood for further study, and excluded datasets that examined only vaccine response, were performed only in cell culture, used on-chip two-sample arrays, or were done in tissues other than whole blood. The remaining 13 datasets contained 2,396 samples from 10 countries from both adult and pediatric patients (Table 1).

Two gene expression datasets in the GEO (GSE19491 and GSE 42834) contained multiple sub-cohorts. For these datasets, we removed the non-whole-blood samples, normalized the remaining samples as below, and then treated as single cohorts. One pair of datasets (GSE31348 and GSE36238) is a single clinical cohort from Cliff et al. (J. Infect. Dis. (2013) 207:18-29); the raw CEL files were downloaded and gcRMA normalized together to make a single cohort we refer to as 'Cliff Combined' in the manuscript. All affymetrix datasets were gcRMA renormalized from raw data. All non-affymetrix arrays were downloaded in non-normalized form, background corrected using the normal-exponential method, and then quantile normalized (R package limma, Smyth, G. in Bioinformatics and Computational Biology Solutions Using R and Bioconductor (ed Carey V Gentleman R, Dudoit S, Irizarry R and Huber W (eds.)) pp. 397-420 (Springer, New York, 2005)). All data were log 2-transformed prior to use. We downloaded all probe-to-gene mappings from the GEO from the most current SOFT files on Jan. 9, 2015.

We performed a multi-cohort analysis comparing gene expression in patients with either LTB or OD versus patients with ATB. We used three datasets (GSE19491, GSE37250, and GSE42834) as the discovery datasets, and applied two meta-analysis methods: (1) combining effect sizes (Hedges' g) and (2) combining p-values using Fisher's sum of logs method (FIG. 1A); both were then corrected to FDR via Benjamini-Hochberg method. We set significance thresholds for differential expression at FDR <1% and effect size >1.5 fold (in non-log space).

For any given gene set, we defined a TB score as follows: for a sample within a dataset, the expression values of the target genes were mean-centered (to reduce scaling factors between datasets). The mean expression of the downregulated genes was then subtracted from the mean expression of the upregulated genes to yield a single 'TB score' for each sample. This TB score was then directly tested for diagnostic power using ROC curves.

A forward search was conducted as previously described (Sweeney et al. (2015) Sci. Transl. Med. 7:287ra271), with the slight modification of the way the TB score is calculated, as explained above. Briefly, the single gene with the best discriminatory power is taken as the starting point, and then at each subsequent step the gene with the best possible increase in weighted AUC (the sum of the AUC for each dataset times the number of samples in that dataset) is added to the set of genes, until no further additions can increase the weighted AUC more than some threshold amount (here 0.005*N). The forward search always optimizes only the discovery datasets, so that the validation datasets are truly independent tests.

For validation, violin plots show TB score for a given dataset across all subsets of patient samples. Violin plot error bars show inter-quartile range, since they cannot be assumed to have normal distributions within groups. All ROC curves show comparison to ATB patients within a given dataset.

Global ROCs were constructed by binding the expression levels of the three-gene set into a single matrix for all tested datasets (either validation only, FIG. 3, or discovery and validation, FIGS. 10-12). In the re-scaled case, the global mean for each gene was obtained across all samples, and then subtracted from the mean within each dataset, such that the each gene within each dataset had the same mean as all other datasets. This method still preserves the relative differences of a gene between samples within a dataset, as shown in FIGS. 10-12. Note that there are no major pre-scaling differences between datasets run on the same microarray type (e.g. GSE37250, GSE39939, GSE39940, and GSE42834, all run on GPL10558 (Illumina HumanHT-12 V4)). The optimal global cutoff was calculated to maximize sensitivity and specificity (Youden method).

In testing diagnostic gene or transcript sets of other groups, transcripts were always summarized to genes. Genes missing in a given dataset were set at zero for all samples. In every case, the gene set was tested according to its original described model, reconstructed by us using the entire discovery dataset. In manuscripts which provided multiple gene sets, the gene sets with the best original diagnostic power were tested (for instance, Kaforou et al., supra) provide five gene sets for testing ATB against OD, LTB, or both; we only used the best signatures for OD and LTB). Summary ROCs (described below) for the previous gene sets were calculated including both discovery and validation datasets.

Summary ROC curves are constructed according to Kester & Buntinx (Kester et al. (2000) Med. Decis. Making 20:430-439), which incorporates information from the entirety of an ROC curve, rather than relying on a single summary point (Q*). Briefly, each ROC curve is modeled as a logistic function of its sensitivity and specificity at each cutoff point; the parameters for the ROC curve (alpha and beta) are estimated using weighted linear regression, with errors estimated with a bootstrap of 10,000 repetitions with replacement. The summary alpha and beta parameters are combined using a random-effects model, with errors carried through from the bootstrap. The summary alpha and beta are then re-transformed to construct a summary ROC curve (FIG. 24). Upper and lower summary ROC confidence intervals are each constructed with the upper and lower bounds on beta, reflecting uncertainty for curve skewness. AUCs of the summary curves are calculated using the trapezoidal method with 1000 points.

Briefly, to test gene signatures in gene expression patterns from known sorted cells, we aggregated public gene expression data from several immune cell types and then calculated the relevant TB-score in each cell type genome, as described previously (Sweeney et al. (2015) Sci. Transl. Med. 7:287ra271).

Between-groups TB score comparisons were done using the Wilcoxon rank sum test. Significance levels were set at two-tailed $P<0.05$, unless specified otherwise. All computation and calculations were carried out in the R language for statistical computing (version 3.0.2). The core multi-cohort analysis code is available as an R package called 'MetaIntegrator'.

TABLE 1

Summary table of all datasets that matched inclusion criteria (whole blood, clinically active pulmonary TB).

| ID | Year | First Author | Platform | Use Here | Country | Age | HIV Status | ATB Culture or Smear |
|---|---|---|---|---|---|---|---|---|
| GSE19491 | 2010 | Berry | GPL6947 | Discovery | South Africa, UK, USA | Adults | Neg | Pos |
| GSE25534 | 2010 | Maertzdorf | GPL1708 | Validation | South Africa | Adults | Neg | Pos |
| GSE28623 | 2011 | Maertzdorf | GPL4133/ GPL6480 | Validation | The Gambia | Adults | Neg | Pos |
| Cliff Combined Dataset | 2013 | Cliff | GPL570 | Validation | South Africa | Adults | Neg | Pos |
| GSE34608 | 2012 | Maertzdorf | GPL4133/ GPL6480 | Validation | Germany | Adults | Neg | Pos |
| GSE37250 | 2014 | Kaforou | GPL10558 | Discovery | Malawi, South Africa | Adults | Pos & Neg | Pos |
| GSE39939 | 2014 | Anderson | GPL10558 | Validation | Kenya | Children | Pos & Neg | Pos & Neg |
| GSE39940 | | | | Validation | Malawi, South Africa | Children | Pos & Neg | Pos |

TABLE 1-continued

Summary table of all datasets that matched inclusion criteria
(whole blood, clinically active pulmonary TB).

| GSE40553 | 2012 | Bloom | GPL10558 | Validation | South Africa, UK | Adults | Neg | Pos |
| GSE41055 | 2013 | Verhagen | GPL5175 | Validation | Venezuela | Children | Neg | Pos & Neg |
| GSE42834 | 2014 | Bloom | GPL10558 | Discovery | UK & France | Adults | Neg | Pos |
| GSE56153 | 2012 | Ottenhoff | GPL6883 | Validation | Indonesia | Adults | Neg | Pos |
| GSE62147 | 2015 | Tientcheu | GPL6480 | Validation | The Gambia | Adults | Neg | Pos |

| ID | HC | LTB | OD | ATB | Treatment | Total | Miscellaneous |
|---|---|---|---|---|---|---|---|
| GSE19491 | 86 | 69 | 212 | 73 | | 440 | OD breakdown: 28 ASLE, 94 PSLE, 31 Still's, 59 Strep and/or Staph infection. Post-treatment samples not used. |
| GSE25534 | 6 | 19 | | 19 | | 44 | Two-color array (on-chip comparisons between HC, LTB, and ATB) |
| GSE28623 | 37 | 25 | | 46 | | 108 | |
| Cliff Combined Dataset | | | | 36 | 117 | 153 | Treatment measured at 1, 2, 4 and 26 weeks |
| GSE34608 | 18 | | 18 | 8 | | 26 | OD all sarcoid |
| GSE37250 | | 167 | 175 | 195 | | 537 | See ref for OD distributions; 194 OD pts reported but only 175 available with microarrays. |
| GSE39939 | | 14 | 64 | 44 neg 35 pos | | 157 | OD breakdown: 33 pneumonia, 5 sepsis, 7 malnutrition, 19 other |
| GSE39940 | | 54 | 169 | 111 | | 334 | OD breakdown: 86 pneumonia, 8 CLD, 11 URI, 34 other infections, 12 malignancy, 18 other |
| GSE40553 | | | | 36 | 130 | 166 | Treatment measured at 0.5, 2, 4, 6 and 12 months. Two cohorts followed. LTB not used; overlaps with GSE19491 |
| GSE41055 | 9 | 9 | | 7 neg 2 pos | | 27 | |
| GSE42834 | 118 | | 123 | 40 | | 281 | OD breakdown: 83 sarcoid, 24 pneumonia, 16 cancer |
| GSE56153 | 18 | | 18 | 35 | | 71 | Treatment measured at 8 and 28 weeks |
| GSE62147 | | | 26 | 26 | | 52 | *M. africanum* and *M. tuberculosis* |

TABLE 2

List of all genes found to be significant (q < 0.01, ES > 1.5-fold) in multi-cohort analysis, sorted according to absolute summary effect size.

| | Number of studies | Summary effect size | Summary std. error | p-value | q-value (FDR) | tau squared | Q | df | resid. hetero p-value |
|---|---|---|---|---|---|---|---|---|---|
| GBP5 | 3 | 1.574 | 0.368 | 1.90E-05 | 0.000277 | 0.382 | 35.899 | 2 | 1.60E-08 |
| ANKRD22 | 3 | 1.443 | 0.233 | 6.27E-10 | 2.65E-08 | 0.152 | 30.041 | 2 | 3.00E-07 |
| GBP2 | 3 | 1.367 | 0.349 | 8.93E-05 | 0.00106 | 0.341 | 33.813 | 2 | 4.55E-08 |
| BATF2 | 3 | 1.355 | 0.223 | 1.24E-09 | 4.97E-08 | 0.126 | 13.94 | 2 | 0.000939 |
| WDFY1 | 3 | 1.284 | 0.248 | 2.11E-07 | 5.24E-06 | 0.161 | 17.384 | 2 | 0.000168 |
| GBP6 | 3 | 1.284 | 0.302 | 2.14E-05 | 0.000308 | 0.262 | 51.137 | 2 | 7.87E-12 |
| CD274 | 3 | 1.271 | 0.325 | 9.14E-05 | 0.00108 | 0.293 | 29.955 | 2 | 3.13E-07 |
| DUSP3 | 3 | 1.27 | 0.393 | 0.001223 | 0.009737 | 0.44 | 43.46 | 2 | 3.65E-10 |
| VAMP5 | 3 | 1.228 | 0.231 | 1.03E-07 | 2.76E-06 | 0.138 | 15.345 | 2 | 0.000465 |
| C1QB | 3 | 1.184 | 0.141 | 4.83E-17 | 7.15E-15 | 0.039 | 5.805 | 2 | 0.054891 |
| CASP5 | 3 | 1.169 | 0.252 | 3.41E-06 | 6.09E-05 | 0.167 | 18.393 | 2 | 0.000101 |
| FLVCR2 | 3 | 1.161 | 0.282 | 3.75E-05 | 0.000499 | 0.215 | 23.056 | 2 | 9.85E-06 |
| GBP1 | 3 | 1.1 | 0.1 | 5.58E-28 | 3.73E-25 | 0.02 | 5.984 | 2 | 0.050189 |
| FAM26F | 3 | 1.098 | 0.201 | 4.70E-08 | 1.38E-06 | 0.099 | 11.905 | 2 | 0.002599 |
| ETV7 | 3 | 1.084 | 0.207 | 1.76E-07 | 4.42E-06 | 0.107 | 12.709 | 2 | 0.001739 |
| BRSK1 | 3 | 1.076 | 0.322 | 0.000839 | 0.007183 | 0.289 | 30.567 | 2 | 2.30E-07 |
| LAP3 | 3 | 1.06 | 0.097 | 7.36E-28 | 4.53E-25 | 0.01 | 2.976 | 2 | 0.225874 |
| PSME2 | 3 | 1.06 | 0.121 | 1.67E-18 | 3.34E-16 | 0.024 | 4.395 | 2 | 0.111098 |
| TAP1 | 3 | 1.054 | 0.122 | 7.20E-18 | 1.27E-15 | 0.025 | 4.515 | 2 | 0.104586 |
| PSMB9 | 3 | 1.046 | 0.204 | 2.81E-07 | 6.76E-06 | 0.113 | 24.752 | 2 | 4.22E-06 |
| C1QC | 3 | 1.044 | 0.091 | 1.16E-30 | 1.05E-27 | 0.007 | 2.676 | 2 | 0.262414 |
| GBP4 | 3 | 1.027 | 0.101 | 3.89E-24 | 1.50E-21 | 0.012 | 3.231 | 2 | 0.198778 |
| SCO2 | 3 | 1.026 | 0.13 | 2.34E-15 | 2.59E-13 | 0.03 | 5.083 | 2 | 0.078764 |
| SOCS1 | 3 | 1.017 | 0.19 | 8.49E-08 | 2.31E-06 | 0.087 | 10.795 | 2 | 0.004527 |
| PSTPIP2 | 3 | 1.017 | 0.216 | 2.49E-06 | 4.62E-05 | 0.119 | 13.952 | 2 | 0.000934 |
| CACNA1E | 3 | 1.006 | 0.174 | 7.67E-09 | 2.59E-07 | 0.07 | 9.096 | 2 | 0.01059 |
| GK | 3 | 0.994 | 0.125 | 1.52E-15 | 1.75E-13 | 0.036 | 9.349 | 2 | 0.009329 |
| LHFPL2 | 3 | 0.993 | 0.216 | 4.16E-06 | 7.27E-05 | 0.118 | 14.068 | 2 | 0.000882 |
| C2 | 3 | 0.992 | 0.157 | 2.57E-10 | 1.18E-08 | 0.053 | 7.456 | 2 | 0.024037 |
| GADD45B | 3 | 0.984 | 0.116 | 2.38E-17 | 3.77E-15 | 0.021 | 4.133 | 2 | 0.12664 |
| PDCD1LG2 | 3 | 0.981 | 0.073 | 9.46E-41 | 2.42E-37 | 0 | 1.909 | 2 | 0.385056 |
| STAT1 | 3 | 0.974 | 0.122 | 1.27E-15 | 1.48E-13 | 0.037 | 13.425 | 2 | 0.001215 |
| KCNJ2 | 3 | 0.974 | 0.221 | 1.09E-05 | 0.000172 | 0.126 | 14.752 | 2 | 0.000626 |
| AIM2 | 3 | 0.97 | 0.052 | 1.17E-77 | 1.80E-73 | 0 | 1.544 | 2 | 0.462093 |
| SLC6A12 | 3 | 0.969 | 0.196 | 7.67E-07 | 1.62E-05 | 0.094 | 11.591 | 2 | 0.003042 |
| P2RY14 | 3 | 0.931 | 0.121 | 1.77E-14 | 1.69E-12 | 0.037 | 13.394 | 2 | 0.001234 |
| FRMD3 | 3 | 0.924 | 0.073 | 1.11E-36 | 2.43E-33 | 0 | 0.737 | 2 | 0.691755 |
| C5 | 3 | 0.924 | 0.17 | 5.78E-08 | 1.65E-06 | 0.066 | 8.835 | 2 | 0.012062 |
| TIFA | 3 | 0.921 | 0.134 | 6.91E-12 | 4.15E-10 | 0.034 | 5.498 | 2 | 0.064002 |
| TAP2 | 3 | 0.918 | 0.166 | 3.40E-08 | 1.03E-06 | 0.072 | 16.864 | 2 | 0.000218 |
| TRAFD1 | 3 | 0.917 | 0.127 | 4.86E-13 | 3.61E-11 | 0.028 | 4.925 | 2 | 0.085235 |
| SESTD1 | 3 | 0.913 | 0.093 | 1.66E-22 | 5.32E-20 | 0.008 | 2.871 | 2 | 0.238033 |
| IFI30 | 3 | 0.91 | 0.073 | 1.14E-35 | 2.19E-32 | 0 | 0.547 | 2 | 0.760598 |
| PARP14 | 3 | 0.9 | 0.073 | 5.60E-35 | 9.56E-32 | 0 | 0.681 | 2 | 0.71129 |
| MOV10 | 3 | 0.897 | 0.106 | 2.05E-17 | 3.36E-15 | 0.015 | 3.516 | 2 | 0.172398 |
| TRIM21 | 3 | 0.892 | 0.195 | 4.75E-06 | 8.18E-05 | 0.093 | 11.592 | 2 | 0.00304 |
| TIMM10 | 3 | 0.889 | 0.094 | 2.89E-21 | 7.40E-19 | 0.009 | 2.899 | 2 | 0.234702 |
| HIST2H2AC | 3 | 0.888 | 0.131 | 1.16E-11 | 6.70E-10 | 0.032 | 5.281 | 2 | 0.07132 |
| CFB | 3 | 0.888 | 0.166 | 8.72E-08 | 2.37E-06 | 0.062 | 8.425 | 2 | 0.014808 |
| FBXO6 | 3 | 0.873 | 0.143 | 8.94E-10 | 3.69E-08 | 0.041 | 6.269 | 2 | 0.043511 |
| EPSTI1 | 3 | 0.868 | 0.117 | 1.17E-13 | 9.78E-12 | 0.022 | 4.256 | 2 | 0.119075 |
| TAPBPL | 3 | 0.86 | 0.244 | 0.000431 | 0.004086 | 0.158 | 18.254 | 2 | 0.000109 |
| KREMEN1 | 3 | 0.859 | 0.167 | 2.89E-07 | 6.89E-06 | 0.077 | 25.914 | 2 | 2.36E-06 |
| MICB | 3 | 0.857 | 0.083 | 5.55E-25 | 2.37E-22 | 0.004 | 2.389 | 2 | 0.302917 |
| RTP4 | 3 | 0.853 | 0.073 | 7.57E-32 | 8.95E-29 | 0 | 0.903 | 2 | 0.636725 |
| SLAMF8 | 3 | 0.84 | 0.073 | 5.04E-31 | 4.85E-28 | 0 | 0.012 | 2 | 0.993886 |
| KCNJ15 | 3 | 0.839 | 0.089 | 6.65E-21 | 1.62E-18 | 0.017 | 7.388 | 2 | 0.024869 |
| LMNB1 | 3 | 0.828 | 0.208 | 6.71E-05 | 0.00083 | 0.108 | 13.273 | 2 | 0.001312 |
| ZNF438 | 3 | 0.824 | 0.19 | 1.47E-05 | 0.000223 | 0.088 | 11.153 | 2 | 0.003786 |
| APOL6 | 3 | 0.823 | 0.073 | 1.70E-29 | 1.38E-26 | 0 | 2.016 | 2 | 0.364927 |
| SP140 | 3 | 0.815 | 0.105 | 7.51E-15 | 7.65E-13 | 0.026 | 10.16 | 2 | 0.006221 |
| EIF4G3 | 3 | 0.814 | 0.077 | 4.79E-26 | 2.37E-23 | 0.002 | 2.169 | 2 | 0.338072 |
| IFITM3 | 3 | 0.806 | 0.072 | 7.72E-29 | 5.65E-26 | 0 | 1.039 | 2 | 0.594727 |
| TRIM56 | 3 | 0.803 | 0.229 | 0.000446 | 0.004207 | 0.136 | 16.167 | 2 | 0.000309 |
| DYNLT1 | 3 | 0.801 | 0.126 | 2.00E-10 | 9.40E-09 | 0.028 | 4.962 | 2 | 0.083652 |
| ADM | 3 | 0.786 | 0.102 | 1.43E-14 | 1.38E-12 | 0.013 | 3.381 | 2 | 0.184428 |
| IFI35 | 3 | 0.784 | 0.072 | 1.82E-27 | 1.04E-24 | 0 | 1.264 | 2 | 0.531439 |
| STAT2 | 3 | 0.776 | 0.072 | 5.59E-27 | 3.07E-24 | 0 | 0.275 | 2 | 0.871616 |
| RARRES3 | 3 | 0.775 | 0.101 | 1.95E-14 | 1.84E-12 | 0.013 | 3.33 | 2 | 0.189186 |

TABLE 2-continued

List of all genes found to be significant (q < 0.01, ES > 1.5-fold) in multi-cohort analysis, sorted according to absolute summary effect size.

| | Number of studies | Summary effect size | Summary std. error | p-value | q-value (FDR) | tau squared | Q | df | resid. hetero p-value |
|---|---|---|---|---|---|---|---|---|---|
| FGL2 | 3 | 0.775 | 0.089 | 2.79E−18 | 5.36E−16 | 0.006 | 2.688 | 2 | 0.26086 |
| TNFSF10 | 3 | 0.775 | 0.072 | 6.90E−27 | 3.66E−24 | 0 | 0.489 | 2 | 0.783211 |
| CEACAM1 | 3 | 0.773 | 0.047 | 1.12E−60 | 8.63E−57 | 0.001 | 2.348 | 2 | 0.309098 |
| PARP9 | 3 | 0.761 | 0.068 | 2.63E−29 | 2.02E−26 | 0.005 | 3.029 | 2 | 0.219966 |
| IGF2BP3 | 3 | 0.76 | 0.127 | 2.08E−09 | 7.99E−08 | 0.029 | 5.066 | 2 | 0.07941 |
| HIST1H3D | 3 | 0.759 | 0.106 | 8.91E−13 | 6.40E−11 | 0.015 | 3.624 | 2 | 0.163338 |
| FAM111A | 3 | 0.755 | 0.225 | 0.000801 | 0.006928 | 0.142 | 31.654 | 2 | 1.34E−07 |
| C1QA | 3 | 0.755 | 0.152 | 6.64E−07 | 1.43E−05 | 0.049 | 7.245 | 2 | 0.026718 |
| APOL1 | 3 | 0.753 | 0.131 | 8.64E−09 | 2.88E−07 | 0.041 | 10.731 | 2 | 0.004676 |
| BST2 | 3 | 0.752 | 0.121 | 5.31E−10 | 2.31E−08 | 0.025 | 4.618 | 2 | 0.099337 |
| EPB41L3 | 3 | 0.751 | 0.231 | 0.001114 | 0.009063 | 0.139 | 16.529 | 2 | 0.000258 |
| ATF5 | 3 | 0.751 | 0.072 | 1.92E−25 | 8.94E−23 | 0 | 1.899 | 2 | 0.387008 |
| PLAUR | 3 | 0.75 | 0.218 | 0.000588 | 0.00532 | 0.136 | 44.678 | 2 | 1.99E−10 |
| SAMD9L | 3 | 0.736 | 0.072 | 1.78E−24 | 7.21E−22 | 0 | 1.527 | 2 | 0.466101 |
| IFIT3 | 3 | 0.734 | 0.119 | 6.45E−10 | 2.70E−08 | 0.035 | 13.251 | 2 | 0.001326 |
| MR1 | 3 | 0.731 | 0.12 | 1.19E−09 | 4.80E−08 | 0.024 | 4.604 | 2 | 0.100069 |
| XAF1 | 3 | 0.731 | 0.151 | 1.27E−06 | 2.56E−05 | 0.058 | 14.216 | 2 | 0.000819 |
| USF1 | 3 | 0.73 | 0.126 | 6.36E−09 | 2.19E−07 | 0.037 | 9.876 | 2 | 0.007168 |
| DHRS12 | 3 | 0.727 | 0.18 | 5.62E−05 | 0.000711 | 0.091 | 30.464 | 2 | 2.43E−07 |
| IGSF6 | 3 | 0.722 | 0.193 | 0.000176 | 0.001898 | 0.091 | 11.586 | 2 | 0.003048 |
| SLC26A8 | 3 | 0.721 | 0.087 | 1.73E−16 | 2.37E−14 | 0.018 | 9.623 | 2 | 0.008136 |
| CYBB | 3 | 0.719 | 0.072 | 1.60E−23 | 6.01E−21 | 0 | 0.598 | 2 | 0.741435 |
| TRIM22 | 3 | 0.711 | 0.178 | 6.32E−05 | 0.000788 | 0.074 | 9.846 | 2 | 0.007277 |
| IL27 | 3 | 0.71 | 0.18 | 8.26E−05 | 0.00099 | 0.077 | 10.214 | 2 | 0.006053 |
| RAB24 | 3 | 0.71 | 0.204 | 0.000498 | 0.004628 | 0.12 | 65.274 | 2 | 6.66E−15 |
| PSME1 | 3 | 0.709 | 0.133 | 1.06E−07 | 2.83E−06 | 0.043 | 11.163 | 2 | 0.003768 |
| TMEM140 | 3 | 0.706 | 0.087 | 6.91E−16 | 8.51E−14 | 0.006 | 2.64 | 2 | 0.267162 |
| SECTM1 | 3 | 0.704 | 0.122 | 8.03E−09 | 2.69E−07 | 0.026 | 4.756 | 2 | 0.092729 |
| ATG3 | 3 | 0.699 | 0.08 | 1.89E−18 | 3.73E−16 | 0.01 | 4.029 | 2 | 0.133397 |
| KARS | 3 | 0.695 | 0.072 | 3.22E−22 | 9.90E−20 | 0 | 0.887 | 2 | 0.641684 |
| TNFAIP2 | 3 | 0.695 | 0.107 | 7.09E−11 | 3.58E−09 | 0.016 | 3.684 | 2 | 0.158466 |
| KIF1B | 3 | 0.692 | 0.208 | 0.000906 | 0.007648 | 0.123 | 41.082 | 2 | 1.20E−09 |
| JAK2 | 3 | 0.688 | 0.072 | 7.94E−22 | 2.22E−19 | 0 | 1.952 | 2 | 0.376858 |
| CNDP2 | 3 | 0.687 | 0.072 | 8.91E−22 | 2.45E−19 | 0 | 1.008 | 2 | 0.604132 |
| CNIH4 | 3 | 0.687 | 0.21 | 0.001099 | 0.008972 | 0.112 | 13.877 | 2 | 0.00097 |
| IFITM1 | 3 | 0.686 | 0.144 | 1.86E−06 | 3.57E−05 | 0.043 | 6.542 | 2 | 0.037978 |
| LACTB | 3 | 0.68 | 0.105 | 9.33E−11 | 4.63E−09 | 0.026 | 10.365 | 2 | 0.005613 |
| TCN2 | 3 | 0.677 | 0.091 | 7.97E−14 | 6.92E−12 | 0.007 | 2.797 | 2 | 0.246936 |
| ADCY3 | 3 | 0.677 | 0.175 | 0.000107 | 0.001227 | 0.071 | 9.617 | 2 | 0.008161 |
| ACOT9 | 3 | 0.675 | 0.177 | 0.000132 | 0.001475 | 0.083 | 19.629 | 2 | 5.47E−05 |
| UBE2L6 | 3 | 0.675 | 0.087 | 8.32E−15 | 8.36E−13 | 0.016 | 7.077 | 2 | 0.029064 |
| HPSE | 3 | 0.675 | 0.062 | 1.52E−27 | 8.98E−25 | 0.003 | 2.658 | 2 | 0.264722 |
| ALDH1A1 | 3 | 0.675 | 0.075 | 2.54E−19 | 5.43E−17 | 0.008 | 3.669 | 2 | 0.159682 |
| SQRDL | 3 | 0.67 | 0.082 | 3.39E−16 | 4.41E−14 | 0.004 | 2.404 | 2 | 0.300647 |
| RHBDF2 | 3 | 0.669 | 0.19 | 0.00042 | 0.004013 | 0.103 | 44.707 | 2 | 1.96E−10 |
| LIMK2 | 3 | 0.666 | 0.149 | 7.78E−06 | 0.000127 | 0.061 | 28.033 | 2 | 8.18E−07 |
| PRPS2 | 3 | 0.663 | 0.112 | 3.52E−09 | 1.30E−07 | 0.028 | 7.97 | 2 | 0.018591 |
| IL15 | 3 | 0.66 | 0.128 | 2.26E−07 | 5.57E−06 | 0.044 | 20.476 | 2 | 3.58E−05 |
| HIST1H2BG | 3 | 0.659 | 0.072 | 3.56E−20 | 8.43E−18 | 0 | 1.389 | 2 | 0.499284 |
| GPR65 | 3 | 0.659 | 0.177 | 0.000192 | 0.002052 | 0.083 | 19.71 | 2 | 5.25E−05 |
| DTX3L | 3 | 0.658 | 0.132 | 6.43E−07 | 1.39E−05 | 0.033 | 5.578 | 2 | 0.061489 |
| CASP1 | 3 | 0.657 | 0.08 | 3.12E−16 | 4.11E−14 | 0.013 | 6.025 | 2 | 0.049159 |
| SORT1 | 3 | 0.651 | 0.197 | 0.000971 | 0.008094 | 0.097 | 12.296 | 2 | 0.002138 |
| SAT1 | 3 | 0.648 | 0.072 | 1.29E−19 | 2.84E−17 | 0 | 0.475 | 2 | 0.788444 |
| GPBAR1 | 3 | 0.646 | 0.173 | 0.000188 | 0.002009 | 0.079 | 18.919 | 2 | 7.79E−05 |
| KLHDC8B | 3 | 0.645 | 0.121 | 1.03E−07 | 2.76E−06 | 0.025 | 4.729 | 2 | 0.093987 |
| TNFSF13B | 3 | 0.642 | 0.128 | 5.41E−07 | 1.20E−05 | 0.039 | 10.39 | 2 | 0.005544 |
| TLR7 | 3 | 0.637 | 0.102 | 3.83E−10 | 1.70E−08 | 0.013 | 3.421 | 2 | 0.180732 |
| OBFC2A | 3 | 0.634 | 0.123 | 2.80E−07 | 6.75E−06 | 0.027 | 4.854 | 2 | 0.088302 |
| ZCCHC6 | 3 | 0.632 | 0.071 | 9.68E−19 | 1.99E−16 | 0 | 0.435 | 2 | 0.804552 |
| ZBP1 | 3 | 0.631 | 0.158 | 6.26E−05 | 0.000783 | 0.055 | 7.864 | 2 | 0.019606 |
| XRN1 | 3 | 0.63 | 0.091 | 4.43E−12 | 2.77E−10 | 0.015 | 5.237 | 2 | 0.072901 |
| IFI6 | 3 | 0.628 | 0.149 | 2.57E−05 | 0.000361 | 0.057 | 14.106 | 2 | 0.000865 |
| MFSD7 | 3 | 0.627 | 0.136 | 3.78E−06 | 6.66E−05 | 0.036 | 5.868 | 2 | 0.053173 |
| KYNU | 3 | 0.624 | 0.166 | 0.000171 | 0.001847 | 0.072 | 17.507 | 2 | 0.000158 |
| CTSL1 | 3 | 0.624 | 0.127 | 8.53E−07 | 1.78E−05 | 0.041 | 15.148 | 2 | 0.000514 |
| FAS | 3 | 0.623 | 0.051 | 6.81E−35 | 1.05E−31 | 0 | 1.118 | 2 | 0.571681 |
| SRBD1 | 3 | 0.62 | 0.097 | 1.47E−10 | 7.08E−09 | 0.011 | 3.135 | 2 | 0.208523 |
| BTN3A1 | 3 | 0.617 | 0.079 | 5.70E−15 | 5.96E−13 | 0.009 | 4.028 | 2 | 0.133439 |
| PLSCR1 | 3 | 0.616 | 0.144 | 1.81E−05 | 0.000266 | 0.042 | 6.532 | 2 | 0.038165 |

TABLE 2-continued

List of all genes found to be significant (q < 0.01, ES > 1.5-fold) in multi-cohort analysis, sorted according to absolute summary effect size.

| | Number of studies | Summary effect size | Summary std. error | p-value | q-value (FDR) | tau squared | Q | df | resid. hetero p-value |
|---|---|---|---|---|---|---|---|---|---|
| SCARF1 | 3 | 0.613 | 0.051 | 1.50E−33 | 1.92E−30 | 0 | 1.262 | 2 | 0.532076 |
| HLA-DMA | 3 | 0.612 | 0.171 | 0.000335 | 0.003307 | 0.067 | 9.235 | 2 | 0.00988 |
| FAM20A | 3 | 0.611 | 0.12 | 3.48E−07 | 8.12E−06 | 0.024 | 4.626 | 2 | 0.098954 |
| SLITRK4 | 3 | 0.611 | 0.141 | 1.53E−05 | 0.000232 | 0.04 | 6.35 | 2 | 0.041801 |
| C5orf15 | 3 | 0.61 | 0.109 | 1.94E−08 | 6.09E−07 | 0.017 | 3.85 | 2 | 0.145871 |
| ASGR1 | 3 | 0.609 | 0.175 | 0.000517 | 0.004764 | 0.072 | 9.74 | 2 | 0.007672 |
| LMO2 | 3 | 0.607 | 0.141 | 1.66E−05 | 0.000246 | 0.04 | 6.302 | 2 | 0.042814 |
| CDS2 | 3 | 0.607 | 0.072 | 3.41E−17 | 5.19E−15 | 0 | 2.022 | 2 | 0.36378 |
| SIPA1L1 | 3 | 0.606 | 0.071 | 1.94E−17 | 3.21E−15 | 0 | 1.113 | 2 | 0.573209 |
| CXCL10 | 3 | 0.605 | 0.071 | 2.32E−17 | 3.71E−15 | 0 | 0.847 | 2 | 0.654779 |
| TMEM180 | 3 | 0.601 | 0.177 | 0.000681 | 0.00603 | 0.074 | 9.911 | 2 | 0.007045 |
| LMTK2 | 3 | 0.596 | 0.097 | 6.55E−10 | 2.74E−08 | 0.01 | 3.132 | 2 | 0.20883 |
| BAZ1A | 3 | 0.595 | 0.095 | 4.49E−10 | 1.98E−08 | 0.018 | 5.788 | 2 | 0.055351 |
| HIST2H2AB | 3 | 0.593 | 0.071 | 8.74E−17 | 1.24E−14 | 0 | 0.131 | 2 | 0.936483 |
| MTHFD2 | 3 | 0.593 | 0.042 | 3.68E−46 | 1.42E−42 | 0 | 1.716 | 2 | 0.423925 |
| FCER1G | 3 | 0.593 | 0.13 | 5.28E−06 | 8.96E−05 | 0.032 | 5.428 | 2 | 0.066283 |
| IFNAR1 | 3 | 0.587 | 0.138 | 2.06E−05 | 0.000298 | 0.038 | 6.072 | 2 | 0.048016 |
| TMEM51 | 3 | 0.587 | 0.13 | 5.93E−06 | 9.88E−05 | 0.031 | 5.388 | 2 | 0.067607 |
| CUL1 | 3 | 0.586 | 0.071 | 2.16E−16 | 2.94E−14 | 0 | 0.727 | 2 | 0.6951 |
| ZNF671 | 3 | −0.586 | 0.16 | 0.000256 | 0.002631 | 0.057 | 8.177 | 2 | 0.016763 |
| CARD11 | 3 | −0.587 | 0.179 | 0.001012 | 0.008388 | 0.076 | 10.127 | 2 | 0.006323 |
| WDR6 | 3 | −0.59 | 0.071 | 1.23E−16 | 1.71E−14 | 0 | 0.121 | 2 | 0.941134 |
| TLE1 | 3 | −0.592 | 0.183 | 0.001199 | 0.009587 | 0.08 | 10.587 | 2 | 0.005025 |
| HPCAL4 | 3 | −0.592 | 0.128 | 3.77E−06 | 6.66E−05 | 0.03 | 5.262 | 2 | 0.071999 |
| ORAI1 | 3 | −0.592 | 0.13 | 5.35E−06 | 9.07E−05 | 0.032 | 5.425 | 2 | 0.066378 |
| OXSR1 | 3 | −0.595 | 0.139 | 1.90E−05 | 0.000278 | 0.039 | 6.173 | 2 | 0.045659 |
| CYBASC3 | 3 | −0.596 | 0.1 | 2.20E−09 | 8.42E−08 | 0.012 | 3.305 | 2 | 0.191616 |
| PPM1H | 3 | −0.596 | 0.071 | 6.20E−17 | 8.99E−15 | 0 | 1.749 | 2 | 0.417043 |
| CD28 | 3 | −0.597 | 0.177 | 0.000726 | 0.006373 | 0.074 | 9.895 | 2 | 0.007101 |
| EHBP1 | 3 | −0.599 | 0.18 | 0.000856 | 0.007309 | 0.077 | 10.242 | 2 | 0.005971 |
| TRRAP | 3 | −0.599 | 0.071 | 4.46E−17 | 6.65E−15 | 0 | 1.715 | 2 | 0.424321 |
| GOT2 | 3 | −0.6 | 0.147 | 4.78E−05 | 0.000617 | 0.046 | 6.92 | 2 | 0.031431 |
| PAFAH1B1 | 3 | −0.6 | 0.137 | 1.17E−05 | 0.000182 | 0.037 | 5.975 | 2 | 0.050418 |
| RPS4X | 3 | −0.6 | 0.156 | 0.000117 | 0.001335 | 0.063 | 15.471 | 2 | 0.000437 |
| SWAP70 | 3 | −0.601 | 0.121 | 7.51E−07 | 1.59E−05 | 0.025 | 4.738 | 2 | 0.093565 |
| ABHD14A | 3 | −0.602 | 0.163 | 0.000213 | 0.002243 | 0.059 | 8.385 | 2 | 0.015106 |
| CD5 | 3 | −0.603 | 0.186 | 0.001194 | 0.009567 | 0.084 | 10.979 | 2 | 0.004129 |
| ERP27 | 3 | −0.603 | 0.071 | 3.05E−17 | 4.69E−15 | 0 | 1.882 | 2 | 0.390277 |
| HLA-DOB | 3 | −0.604 | 0.155 | 0.000102 | 0.001181 | 0.053 | 7.688 | 2 | 0.021411 |
| FAM84B | 3 | −0.604 | 0.137 | 9.91E−06 | 0.000158 | 0.037 | 5.963 | 2 | 0.050711 |
| AGMAT | 3 | −0.606 | 0.14 | 1.55E−05 | 0.000234 | 0.04 | 6.258 | 2 | 0.043753 |
| ALDH9A1 | 3 | −0.607 | 0.174 | 0.000495 | 0.004605 | 0.071 | 9.623 | 2 | 0.008137 |
| CD19 | 3 | −0.609 | 0.093 | 4.97E−11 | 2.54E−09 | 0.009 | 2.915 | 2 | 0.232808 |
| SIN3A | 3 | −0.61 | 0.071 | 1.24E−17 | 2.15E−15 | 0 | 0.011 | 2 | 0.994328 |
| CD27 | 3 | −0.611 | 0.132 | 3.56E−06 | 6.32E−05 | 0.033 | 5.549 | 2 | 0.062389 |
| EP400 | 3 | −0.612 | 0.071 | 1.06E−17 | 1.84E−15 | 0 | 0.772 | 2 | 0.679885 |
| FNBP1 | 3 | −0.613 | 0.072 | 2.22E−17 | 3.60E−15 | 0 | 2.029 | 2 | 0.362558 |
| TPK1 | 3 | −0.618 | 0.072 | 5.76E−18 | 1.04E−15 | 0.006 | 3.388 | 2 | 0.183738 |
| ASF1B | 3 | −0.621 | 0.071 | 3.50E−18 | 6.48E−16 | 0 | 1.831 | 2 | 0.400262 |
| IMPDH2 | 3 | −0.622 | 0.071 | 3.26E−18 | 6.19E−16 | 0 | 1.562 | 2 | 0.45789 |
| CD79A | 3 | −0.623 | 0.155 | 5.82E−05 | 0.000735 | 0.065 | 22.797 | 2 | 1.12E−05 |
| SMYD3 | 3 | −0.624 | 0.085 | 2.44E−13 | 1.93E−11 | 0.005 | 2.551 | 2 | 0.279345 |
| PLCG1 | 3 | −0.629 | 0.193 | 0.001105 | 0.009014 | 0.101 | 23.614 | 2 | 7.45E−06 |
| TXK | 3 | −0.631 | 0.17 | 0.000211 | 0.002227 | 0.067 | 9.179 | 2 | 0.010159 |
| SUSD3 | 3 | −0.632 | 0.138 | 4.91E−06 | 8.40E−05 | 0.038 | 6.087 | 2 | 0.047656 |
| GZMK | 3 | −0.633 | 0.165 | 0.000127 | 0.001429 | 0.062 | 8.624 | 2 | 0.013406 |
| TOMM20 | 3 | −0.633 | 0.194 | 0.001109 | 0.009044 | 0.099 | 18.054 | 2 | 0.00012 |
| GTF3A | 3 | −0.637 | 0.162 | 8.07E−05 | 0.000969 | 0.058 | 8.257 | 2 | 0.016109 |
| FAM129C | 3 | −0.639 | 0.132 | 1.34E−06 | 2.69E−05 | 0.033 | 5.584 | 2 | 0.061313 |
| SH2D3A | 3 | −0.639 | 0.161 | 7.01E−05 | 0.000859 | 0.058 | 8.168 | 2 | 0.016842 |
| KIAA1737 | 3 | −0.64 | 0.186 | 0.000592 | 0.005353 | 0.094 | 22.007 | 2 | 1.66E−05 |
| PEX5 | 3 | −0.641 | 0.088 | 3.47E−13 | 2.65E−11 | 0.006 | 2.682 | 2 | 0.261557 |
| AP1M1 | 3 | −0.642 | 0.076 | 1.94E−17 | 3.21E−15 | 0.001 | 2.147 | 2 | 0.341771 |
| OLIG1 | 3 | −0.645 | 0.132 | 1.06E−06 | 2.16E−05 | 0.033 | 5.521 | 2 | 0.063262 |
| BIN1 | 3 | −0.647 | 0.145 | 8.58E−06 | 0.000138 | 0.053 | 13.388 | 2 | 0.001238 |
| VPREB3 | 3 | −0.649 | 0.165 | 8.37E−05 | 0.001001 | 0.062 | 8.634 | 2 | 0.013341 |
| CALM1 | 3 | −0.653 | 0.075 | 4.79E−18 | 8.77E−16 | 0.001 | 2.138 | 2 | 0.343394 |
| NOV | 3 | −0.66 | 0.099 | 2.46E−11 | 1.34E−09 | 0.012 | 3.238 | 2 | 0.198069 |
| SPTAN1 | 3 | −0.662 | 0.072 | 3.96E−20 | 9.09E−18 | 0 | 2.012 | 2 | 0.365716 |

TABLE 2-continued

List of all genes found to be significant (q < 0.01, ES > 1.5-fold) in multi-cohort analysis, sorted according to absolute summary effect size.

| | Number of studies | Summary effect size | Summary std. error | p-value | q-value (FDR) | tau squared | Q | df | resid. hetero p-value |
|---|---|---|---|---|---|---|---|---|---|
| USP11 | 3 | −0.662 | 0.148 | 7.50E−06 | 0.000123 | 0.046 | 6.901 | 2 | 0.03173 |
| MCM5 | 3 | −0.663 | 0.145 | 5.13E−06 | 8.74E−05 | 0.044 | 6.69 | 2 | 0.035265 |
| RBBP7 | 3 | −0.665 | 0.111 | 2.28E−09 | 8.67E−08 | 0.019 | 4 | 2 | 0.135364 |
| HRK | 3 | −0.665 | 0.078 | 1.66E−17 | 2.81E−15 | 0.002 | 2.236 | 2 | 0.326998 |
| IL27RA | 3 | −0.668 | 0.139 | 1.57E−06 | 3.09E−05 | 0.039 | 6.133 | 2 | 0.046584 |
| SMARCC1 | 3 | −0.67 | 0.184 | 0.000277 | 0.002811 | 0.082 | 10.682 | 2 | 0.004792 |
| DKC1 | 3 | −0.671 | 0.167 | 5.84E−05 | 0.000736 | 0.063 | 8.764 | 2 | 0.012502 |
| PPIA | 3 | −0.672 | 0.195 | 0.000562 | 0.005115 | 0.093 | 11.924 | 2 | 0.002575 |
| SLC9A3R1 | 3 | −0.674 | 0.186 | 0.000296 | 0.002977 | 0.084 | 10.895 | 2 | 0.004307 |
| CXCR5 | 3 | −0.675 | 0.096 | 1.62E−12 | 1.12E−10 | 0.018 | 5.797 | 2 | 0.055103 |
| EBF1 | 3 | −0.675 | 0.178 | 0.000149 | 0.00164 | 0.075 | 9.977 | 2 | 0.006815 |
| SLAMF1 | 3 | −0.676 | 0.174 | 9.98E−05 | 0.001157 | 0.07 | 9.483 | 2 | 0.008724 |
| ACTR1B | 3 | −0.691 | 0.131 | 1.30E−07 | 3.37E−06 | 0.032 | 5.418 | 2 | 0.066599 |
| ZNF329 | 3 | −0.692 | 0.072 | 5.42E−22 | 1.57E−19 | 0 | 0.328 | 2 | 0.848939 |
| MOAP1 | 3 | −0.692 | 0.072 | 5.23E−22 | 1.55E−19 | 0 | 0.643 | 2 | 0.725024 |
| KLF13 | 3 | −0.697 | 0.198 | 0.000434 | 0.004109 | 0.097 | 12.236 | 2 | 0.002203 |
| STK38 | 3 | −0.697 | 0.119 | 4.16E−09 | 1.51E−07 | 0.023 | 4.51 | 2 | 0.104878 |
| RBL2 | 3 | −0.7 | 0.135 | 2.17E−07 | 5.36E−06 | 0.035 | 5.752 | 2 | 0.056346 |
| FCRLA | 3 | −0.704 | 0.204 | 0.000543 | 0.004972 | 0.104 | 12.992 | 2 | 0.00151 |
| TRIM28 | 3 | −0.705 | 0.176 | 5.97E−05 | 0.00075 | 0.072 | 9.67 | 2 | 0.007945 |
| MFGE8 | 3 | −0.712 | 0.078 | 9.27E−20 | 2.07E−17 | 0.002 | 2.233 | 2 | 0.327363 |
| CD79B | 3 | −0.713 | 0.12 | 3.10E−09 | 1.16E−07 | 0.037 | 13.645 | 2 | 0.001089 |
| MARCKSL1 | 3 | −0.713 | 0.072 | 3.75E−23 | 1.28E−20 | 0 | 1.878 | 2 | 0.391031 |
| COL9A2 | 3 | −0.716 | 0.072 | 2.15E−23 | 7.70E−21 | 0 | 0.307 | 2 | 0.857815 |
| PRPF8 | 3 | −0.718 | 0.108 | 2.57E−11 | 1.38E−09 | 0.016 | 3.746 | 2 | 0.153695 |
| PNOC | 3 | −0.72 | 0.207 | 0.000516 | 0.004762 | 0.108 | 13.429 | 2 | 0.001213 |
| RNF44 | 3 | −0.727 | 0.09 | 9.40E−16 | 1.13E−13 | 0.007 | 2.771 | 2 | 0.250252 |
| SERTAD2 | 3 | −0.731 | 0.072 | 2.93E−24 | 1.16E−21 | 0 | 1.48 | 2 | 0.477176 |
| CABIN1 | 3 | −0.734 | 0.142 | 2.45E−07 | 5.98E−06 | 0.041 | 6.344 | 2 | 0.04193 |
| P2RY10 | 3 | −0.734 | 0.148 | 7.38E−07 | 1.57E−05 | 0.056 | 13.759 | 2 | 0.001029 |
| NELL2 | 3 | −0.736 | 0.2 | 0.000225 | 0.002349 | 0.099 | 12.42 | 2 | 0.00201 |
| EML4 | 3 | −0.736 | 0.228 | 0.001219 | 0.009716 | 0.135 | 16.167 | 2 | 0.000309 |
| SYTL1 | 3 | −0.739 | 0.111 | 2.37E−11 | 1.30E−09 | 0.018 | 3.934 | 2 | 0.139848 |
| PFAS | 3 | −0.739 | 0.147 | 4.80E−07 | 1.08E−05 | 0.045 | 6.759 | 2 | 0.034066 |
| KIAA0355 | 3 | −0.74 | 0.072 | 9.44E−25 | 3.92E−22 | 0 | 0.644 | 2 | 0.724665 |
| BANK1 | 3 | −0.742 | 0.213 | 0.000501 | 0.004653 | 0.115 | 14.155 | 2 | 0.000844 |
| TBC1D10C | 3 | −0.742 | 0.074 | 1.83E−23 | 6.69E−21 | 0.001 | 2.082 | 2 | 0.35317 |
| CACNA2D3 | 3 | −0.748 | 0.123 | 1.18E−09 | 4.78E−08 | 0.026 | 4.794 | 2 | 0.090969 |
| PITPNC1 | 3 | −0.752 | 0.198 | 0.000152 | 0.001664 | 0.108 | 24.529 | 2 | 4.72E−06 |
| CA5B | 3 | −0.753 | 0.126 | 2.48E−09 | 9.35E−08 | 0.029 | 5.042 | 2 | 0.080392 |
| FLNB | 3 | −0.757 | 0.163 | 3.51E−06 | 6.25E−05 | 0.06 | 8.295 | 2 | 0.015801 |
| ID3 | 3 | −0.768 | 0.134 | 1.14E−08 | 3.71E−07 | 0.035 | 5.679 | 2 | 0.058454 |
| EPHA4 | 3 | −0.772 | 0.072 | 1.04E−26 | 5.36E−24 | 0 | 1.335 | 2 | 0.513033 |
| TATDN2 | 3 | −0.781 | 0.226 | 0.000552 | 0.005044 | 0.133 | 15.848 | 2 | 0.000362 |
| ZNF518B | 3 | −0.789 | 0.222 | 0.000379 | 0.003687 | 0.127 | 15.276 | 2 | 0.000482 |
| GPX7 | 3 | −0.797 | 0.221 | 0.000311 | 0.003103 | 0.126 | 15.104 | 2 | 0.000525 |
| MAP7 | 3 | −0.799 | 0.127 | 3.57E−10 | 1.62E−08 | 0.038 | 10.078 | 2 | 0.006482 |
| BLK | 3 | −0.804 | 0.159 | 4.27E−07 | 9.73E−06 | 0.056 | 7.829 | 2 | 0.019953 |
| DBP | 3 | −0.815 | 0.197 | 3.37E−05 | 0.000454 | 0.095 | 11.928 | 2 | 0.00257 |
| OSBPL10 | 3 | −0.817 | 0.165 | 7.45E−07 | 1.58E−05 | 0.061 | 8.418 | 2 | 0.014865 |
| FAIM3 | 3 | −0.818 | 0.19 | 1.58E−05 | 0.000237 | 0.087 | 11.088 | 2 | 0.003911 |
| SESN1 | 3 | −0.851 | 0.236 | 0.000311 | 0.0031 | 0.146 | 17.1 | 2 | 0.000194 |
| MEF2D | 3 | −0.861 | 0.162 | 1.15E−07 | 3.01E−06 | 0.058 | 8.051 | 2 | 0.017852 |
| KLF2 | 3 | −0.881 | 0.073 | 1.05E−33 | 1.47E−30 | 0 | 1.369 | 2 | 0.504445 |
| ITPKB | 3 | −0.884 | 0.112 | 2.93E−15 | 3.20E−13 | 0.019 | 3.945 | 2 | 0.139101 |
| GNG7 | 3 | −0.907 | 0.108 | 5.38E−17 | 7.88E−15 | 0.016 | 3.697 | 2 | 0.157441 |
| FOXO1 | 3 | −0.951 | 0.214 | 9.19E−06 | 0.000147 | 0.117 | 13.894 | 2 | 0.000961 |
| ARHGEF18 | 3 | −1.027 | 0.235 | 1.23E−05 | 0.00019 | 0.144 | 16.444 | 2 | 0.000269 |

TABLE 3

Test parameters at an automated threshold (maximum sensitivity + specificity) in the discovery datasets. The threshold for each dataset was calculated separately, and then test statistics were generated from the resulting patient classifications. PPV, positive predictive value, NPV, negative predictive value.

| Dataset | sensitivity | specificity | PPV | NPV | accuracy |
|---|---|---|---|---|---|
| Discovery - HC vs. ATB | | | | | |
| GSE19491 | 0.885 | 0.966 | 0.931 | 0.942 | 0.938 |
| GSE42834 | 0.975 | 0.983 | 0.951 | 0.991 | 0.981 |
| Discovery - LTB vs. ATB | | | | | |
| GSE19491 | 0.885 | 0.87 | 0.857 | 0.896 | 0.877 |
| GSE37250 | 0.872 | 0.832 | 0.859 | 0.848 | 0.854 |
| Discovery - OD vs. ATB | | | | | |
| GSE19491 | 0.869 | 0.855 | 0.654 | 0.954 | 0.858 |
| GSE37250 | 0.805 | 0.789 | 0.809 | 0.784 | 0.797 |
| GSE42834 | 0.8 | 0.732 | 0.492 | 0.918 | 0.748 |

TABLE 4

Test parameters at an automated threshold (maximum sensitivity + specificity) in the validation datasets. The threshold for each dataset was calculated separately, and then test statistics were generated from the resulting patient classifications. PPV, positive predictive value, NPV, negative predictive value.

| Dataset | sensitivity | specificity | PPV | NPV | accuracy |
|---|---|---|---|---|---|
| Validation - HC vs. ATB | | | | | |
| GSE28623 | 0.848 | 0.811 | 0.848 | 0.811 | 0.831 |
| GSE34608 | 1 | 1 | 1 | 1 | 1 |
| GSE41055 | 1 | 0.778 | 0.5 | 1 | 0.818 |
| GSE56153 | 0.611 | 0.667 | 0.647 | 0.632 | 0.639 |
| Validation - LTB vs. ATB | | | | | |
| GSE28623 | 0.87 | 0.84 | 0.909 | 0.778 | 0.859 |
| GSE39939 | 0.886 | 0.929 | 0.969 | 0.765 | 0.898 |
| GSE39940 | 0.712 | 0.759 | 0.859 | 0.562 | 0.727 |
| GSE41055 | 1 | 0.889 | 0.667 | 1 | 0.909 |
| Validation - OD vs. ATB | | | | | |
| GSE34608 | 0.5 | 0.611 | 0.364 | 0.733 | 0.577 |
| GSE39939 | 0.771 | 0.875 | 0.771 | 0.875 | 0.838 |
| GSE39940 | 0.685 | 0.74 | 0.633 | 0.781 | 0.718 |

TABLE 5

Linear regressions of TB score on treatment time in weeks. All four datasets show significant decreases over time.

| | Estimate | Std. Error | t value | p value |
|---|---|---|---|---|
| Cliff Combined | | | | |
| (Intercept) | 1.691 | 0.082 | 20.698 | <2e−16 |
| time · weeks | −0.044 | 0.006 | −6.812 | 2.14E−10 |
| Residual standard error: 0.826 on 151 degrees of freedom | | | Multiple R-squared: 0.2351 | |
| GSE40553 | | | | |
| (Intercept) | −1.569 | 0.082 | −19.11 | <2e−16 |
| time · weeks | −0.035 | 0.003 | −10.68 | <2e−16 |
| Residual standard error: 0.7834 on 164 degrees of freedom | | | Multiple R-squared: 0.4101 | |
| GSE56153 | | | | |
| (Intercept) | −1.668 | 0.158 | −10.569 | 1.89E−14 |
| time · weeks | −0.025 | 0.009 | −2.785 | 7.49E−03 |
| Residual standard error: 0.7923 on 51 degrees of freedom | | | Multiple R-squared: 0.132 | |
| GSE62147 | | | | |
| (Intercept) | −0.065 | 0.105 | −0.621 | 5.37E−01 |
| time · weeks | −0.052 | 0.006 | −9.058 | 4.03E−12 |
| Residual standard error: 0.5333 on 50 degrees of freedom | | | Multiple R-squared: 0.6213 | |

Example 2

Derivation of Additional Diagnostic Gene Sets for Pulmonary Tuberculosis

In order to identify additional diagnostic gene sets, we implemented a recursive greedy forward search whereby, at the algorithm's conclusion, the resulting diagnostic gene set was removed from the possible set of significant genes, and the algorithm was run again. The first gene set was taken for further validation, but the other gene sets were noted to perform similarly in the discovery cohorts (Table 6).

TABLE 6

Diagnostic gene sets identified by using a recursive greedy forward search algorithm.

| Order in recursive forward search | positive genes in ATB | negative genes in ATB | GSE19491 AUC | GSE37250 AUC | GSE42834 AUC | mean discovery AUC |
|---|---|---|---|---|---|---|
| 1 | GBP5, DUSP3 | KLF2 | 0.922 | 0.89 | 0.805 | 0.872 |
| 2 | GBP6, HLA-DMA, TAPBPL | TPK1, CD79B, AP1M1 | 0.939 | 0.899 | 0.83 | 0.889 |
| 3 | ANKRD22, ASGR1, C5 | OXSR1 | 0.913 | 0.849 | 0.839 | 0.867 |
| 4 | BATF2, RARRES3, ALDH1A1 | ORAI1, RBBP7, HLA-DOB | 0.944 | 0.888 | 0.828 | 0.887 |
| 5 | VAMP5, PSME2, USF1 | TATDN2, CD79A, COL9A2 | 0.942 | 0.857 | 0.859 | 0.886 |
| 6 | GBP2, FAM111A, BRSK1 | FNBP1, MAP7, IL27RA | 0.924 | 0.857 | 0.843 | 0.875 |
| 7 | WDFY1 | EML4, BANK1, PITPNC1 | 0.906 | 0.817 | 0.812 | 0.845 |
| 8 | GBP1, GPBAR1 | OSBPL10, NOV, MCM5 | 0.902 | 0.831 | 0.838 | 0.857 |
| 9 | CD274, SCO2, KCNJ2 | GNG7, PPM1H | 0.897 | 0.816 | 0.864 | 0.859 |
| 10 | AIM2, GBP4, PRPS2 | PNOC, RNF44 | 0.884 | 0.859 | 0.856 | 0.866 |
| 11 | PSMB9, CNDP2, TAP2, FAM26F | ARHGEF18, SWAP70, SYTL1 | 0.919 | 0.842 | 0.835 | 0.865 |
| 12 | LHFPL2, MOV10, C1QB, P2RY14 | TRIM28, BLK, PPIA | 0.9 | 0.843 | 0.87 | 0.871 |

What is claimed is:

1. A method of treating a patient for tuberculosis, comprising:
   (a) identifying the patient as having tuberculosis based on the expression levels of GBP5, DUSP3 and KLF2 biomarkers in a biological sample from the patient; and
   (b) administering an effective amount of at least one antibiotic to the patient.

2. The method of claim 1, wherein said at least one antibiotic is selected from the group consisting of rifampicin, isoniazid, pyrazinamide, and ethambutol.

3. The method of claim 1, further comprising administering an effective amount of a corticosteroid to the patient.

4. The method of claim 1, further comprising monitoring the patient's response to treatment.

5. The method of claim 1, further comprising calculating a TB score for the patient based on the levels of expression of the biomarkers, wherein a higher TB score for the patient compared to the reference value ranges for the control subject indicates that the patient has active tuberculosis.

6. The method of claim 5, further comprising evaluating disease severity in the patient, wherein an increasing TB score indicates worsening tuberculosis infection and a decreasing TB score indicates recovery from active tuberculosis.

7. The method of claim 1, further comprising distinguishing a diagnosis of active tuberculosis from latent tuberculosis and other pulmonary conditions or infectious diseases.

8. The method of claim 1, wherein the biomarkers are protein biomarkers.

9. The method of claim 1, wherein the biological sample comprises blood, sputum, monocytes, or macrophages.

10. The method of claim 1, wherein the biomarkers are RNA biomarkers.

11. The method of claim 1, wherein the patient has decreased levels of expression of the GBP5 and DUSP3 biomarkers and an increased level of expression of the KLF2 biomarker relative to reference values.

12. The method of claim 1, wherein the at least one antibiotic is selected from the group consisting of rifampicin, isoniazid, pyrazinamide, and ethambutol.

13. A kit comprising reagents for measuring the levels of expression of up to 30 biomarkers, wherein the up to 30 biomarkers comprises GBP5, DUSP3, and KLF2 biomarkers.

14. The kit of claim 13, wherein the reagents are antibodies.

15. The kit of claim 13, wherein the reagents are oligonucleotide probes.

* * * * *